United States Patent
Marcin et al.

(10) Patent No.: US 10,112,944 B2
(45) Date of Patent: Oct. 30, 2018

(54) HETEROCYCLIC COMPOUNDS USEFUL AS INHIBITORS OF TNF

(71) Applicant: BRISTOL-MYERS SQUIBB COMPANY, Princeton, NJ (US)

(72) Inventors: Lawrence R. Marcin, Bethany, CT (US); Stephen T. Wrobleski, Flemington, NJ (US); T.G. Murali Dhar, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/558,724

(22) PCT Filed: Mar. 17, 2016

(86) PCT No.: PCT/US2016/022742
§ 371 (c)(1),
(2) Date: Sep. 15, 2017

(87) PCT Pub. No.: WO2016/149439
PCT Pub. Date: Sep. 22, 2016

(65) Prior Publication Data
US 2018/0072728 A1 Mar. 15, 2018

Related U.S. Application Data

(60) Provisional application No. 62/134,800, filed on Mar. 18, 2015.

(51) Int. Cl.
C07D 471/14 (2006.01)
(52) U.S. Cl.
CPC .................. C07D 471/14 (2013.01)
(58) Field of Classification Search
CPC .................. C07D 471/14
USPC ..................................... 514/233.2
See application file for complete search history.

(56) References Cited

U.S. PATENT DOCUMENTS

| | | | |
|---|---|---|---|
| 6,894,068 B2 | 5/2005 | Michejda et al. | |
| 9,512,124 B2 | 12/2016 | Alexander et al. | |
| 2005/0113397 A1 | 5/2005 | Takemura et al. | |
| 2005/0124638 A1 | 6/2005 | Swayze et al. | |

FOREIGN PATENT DOCUMENTS

| | | |
|---|---|---|
| CN | 101717397 | 11/2012 |
| CN | 101717397 B | 11/2012 |
| JP | 2009-227599 | 10/2009 |
| WO | WO 2004/050035 A2 | 6/2004 |
| WO | WO 2009/045174 A1 | 4/2009 |
| WO | WO 2011/119565 A1 | 9/2011 |
| WO | WO 2012/148550 A1 | 11/2012 |
| WO | WO 2012/160030 A1 | 11/2012 |
| WO | WO 2013/186229 A1 | 12/2013 |
| WO | WO 2014/009295 A1 | 1/2014 |
| WO | WO 2014/009296 A1 | 1/2014 |
| WO | WO 2015/08611 A1 | 6/2015 |
| WO | WO 2015/086496 A1 | 6/2015 |
| WO | WO 2015/086498 A1 | 6/2015 |
| WO | WO 2015/086500 A1 | 6/2015 |
| WO | WO 2015/086505 A1 | 6/2015 |
| WO | WO 2015/086506 A1 | 6/2015 |
| WO | WO 2015/086507 A1 | 6/2015 |
| WO | WO 2015/086509 A1 | 6/2015 |
| WO | WO 2015/086512 A1 | 6/2015 |
| WO | WO 2015/086513 A1 | 6/2015 |
| WO | WO 2015/086519 A1 | 6/2015 |
| WO | WO 2015/086523 A1 | 6/2015 |
| WO | WO 2016/149436 A1 | 9/2016 |
| WO | WO 2016/149437 A1 | 9/2016 |

OTHER PUBLICATIONS

Maes et al., Synthesis of C8[n. 63743]N9 Annulated Purines by Iron-Catalyzed C[n. 63743]H Amination, 2013, Chemistry—A European Journal, 19(28), 9137-9141 (Year: 2013).*
Veljkovic et al., A flexible three-component synthesis of novel alpha-amino acids incorporating an imidazo[1,2-a]pyridine backbone, 2006, Synthesis, 16, 2677-2684 (Year: 2006).*
Chaudhary, Vikas, et al., "Scaffold-hopping and hybridization based design and building block strategic synthesis of pyridine-annulated purines: discovery of novel apoptotic anticancer agents", RSC Advances, Mar. 4, 2015, vol. 5, pp. 26051-26060.
Chimirri, A., et al., "Synthesis and biological activity of novel 1H,3H-thiazolo[3,4-a]benzimidazoles: non-nucleoside human immunodeficiency virus type 1 reverse transcriptase inhibitors", Antiviral Chem. Chemother., 1999, vol. 10, pp. 211-217.
Chimirri, Alba, et al, "Synthesis and Antitumour Activity of 1H,3H-Thiazolo[3,4-a]benzimidazole Derivatives", Archiv der Pharmazie, 2001, vol. 334 (6), pp. 203-208.
Meng, Tao, et al., "Synthesis and biological evaluation of 6H-pyrido[2,1:2,3]imidazo[4,5-c]isoquinolin-5(6H)-ones as antimitotic agents and inhibitors of tubulin polymerization", Bioorganic & Medicinal Chemistry, 2014, vol. 22, pp. 848-855.

(Continued)

Primary Examiner — Kristin A Vajda
(74) Attorney, Agent, or Firm — Gary Greenblatt

(57) ABSTRACT

Disclosed are compounds of Formula (I) or a salt thereof, wherein: X is $CR_6$ or N; W is: (i) —$(CR_3R_3)_{1-4}$— or (ii) —$(CR_3R_3)x$—Y—$(CR_3R_3)y$—; and Y, $R_1$, $R_2$, $R_3$, $R_5$, $R_6$, $R_7$, x, and y are define herein. Also disclosed are methods of using such compounds as modulators of TNFα, and pharmaceutical compositions comprising such compounds. These compounds are useful in treating inflammatory and autoimmune diseases.

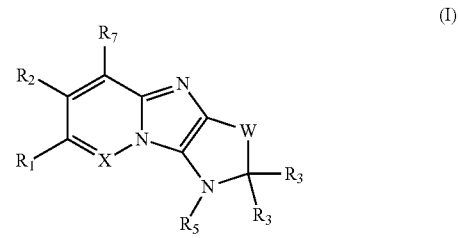

(I)

12 Claims, 2 Drawing Sheets

(56) References Cited

OTHER PUBLICATIONS

International Search Report Application No. PCT/US2016/022742—dated Sep. 19, 2017.

* cited by examiner (II)

(III-a)

(III-b)

(IV-a)

(IV-b)

(IV-c)

(V-a)

(V-b)

(V-c)

(V-d)

HETEROCYCLIC COMPOUNDS USEFUL AS INHIBITORS OF TNF

CROSS-REFERENCE TO RELATED APPLICATIONS

This application is a national phase application under 35 U.S.C. § 371 of International Patent Application No. PCT/US2016/022742, filed Mar. 17, 2016, which claims priority to U.S. Application Ser. No. 62/134,800, filed Mar. 18, 2015, which are expressly incorporated fully herein by reference.

DESCRIPTION

The present invention generally relates to heterocyclic compounds useful as modulators of TNFα signaling. Provided herein are heterocyclic compounds, compositions comprising such compounds, and methods of their use. The invention further pertains to pharmaceutical compositions containing at least one compound according to the invention that are useful for the treatment of conditions related to TNFα activity, including inflammatory and autoimmune disorders.

TNFα is the first and archetypical member of the TNF superfamily (TNFSF) of ligands. TNFSF ligands are involved in the regulation of several key biological processes including cell differentiation, cell survival, cell death, and inflammation. Ligands of the TNF superfamily play a pivotal role in the regulation and orchestration of the immune and inflammatory responses at multiple levels. A common structural feature of TNFSF ligands is the formation of trimeric complexes that can bind to and activate specific TNFSF receptors. Similar to several other family members, TNFα is a type II transmembrane protein that can be secreted as a soluble form following proteolytic cleavage by a metalloprotease. Both the transmembrane and soluble forms of TNFα form biologically active trimeric complexes that signal through TNF receptors 1 and 2. TNFα can act on multiple cell types (T cells, monocytes, endothelial cells) through TNFRs to induce activation of the immune system, production of inflammatory cytokines, osteoclastogenesis, and cell death.

Based on their physiological and pathophysiological functions, TNF and TNFSF ligands are implicated in the pathogenesis of a number of inflammatory and autoimmune disorders (see, for example, Keystone, E. C. et al., *J. Rheumatol.*, 37:27-39 (2010); and Sedger, L. M. et al., *Cytokine Growth Factor Rev.*, 25(4):453-472 (2014)). To date, a number of TNFα modulating agents have been developed and are commercially available. The mechanism of action of clinically-proven protein-based therapeutic agents directed against TNFα is to act as competitive antagonists to inhibit TNFα from binding to TNFR1 and TNFR2. These agents include antibodies specific to TNFα including adalimumab, golimumab, certolizumab pegol, and infliximab. Another approved agent for the treatment of TNFα-mediated disorders is etanercept, a chimera of the immunoglobulin molecule and the TNFR2 ectodomain which also prevents TNFα from binding to the cellular receptors.

Being modulators of human TNFα activity, the heterocyclic compounds are beneficial in the treatment and/or prevention of a number of human maladies. These include inflammatory and autoimmune disorders, neurological and neurodegenerative disorders, pain and nociceptive disorders, cardiovascular disorders, metabolic disorders, ocular disorders, and oncological disorders.

WO 2013/186229, WO 2014/009295, and WO 2014/009296 disclose compounds useful as modulators of TNFα.

In view of the numerous conditions that are contemplated to benefit by treatment involving modulation of TNF, it is immediately apparent that new compounds capable of modulating the signaling of TNFα and methods of using these compounds should provide substantial therapeutic benefits to a wide variety of patients.

The present invention relates to a new class of heterocyclic compounds found to be effective inhibitors of TNFα activity. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of TNFα, and are useful for the treatment of inflammatory and autoimmune disorders, neurological and neurodegenerative disorders, cardiovascular disorders, metabolic disorders, ocular disorders, and oncological disorders; or stereoisomers, tautomers, pharmaceutically acceptable salts, solvates or prodrugs thereof.

The present invention also provides pharmaceutical compositions comprising a pharmaceutically acceptable carrier and at least one of the compounds of Formula (I) or stereoisomers, tautomers, pharmaceutically acceptable salts, solvates, or prodrugs thereof.

The present invention also provides a method for modulation of TNFα comprising administering to a host in need of such treatment a therapeutically effective amount of at least one of the compounds of Formula (I) or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of Formula (I) or stereoisomers, tautomers, pharmaceutically acceptable salts, solvates, or prodrugs thereof.

One embodiment provides a method for treating inflammatory and autoimmune diseases. Particular, inflammatory and autoimmune diseases include, but are not limited to, systemic lupus erythematosus, psoriasis, Crohn's disease, ulcerative colitis, asthma, graft versus host disease, allograft rejection, chronic obstructive pulmonary disease, Graves' disease, rheumatoid arthritis, lupus nephritis, cutaneous lupus, ankylosing spondylitis, cryopyrin-associated periodic syndromes (CAPS), TNF receptor associated periodic syndrome (TRAPS), Wegener's granulomatosis, sarcoidosis, familial Mediterranean fever (FMF), adult onset stills, systemic onset juvenile idiopathic arthritis, psoriatic arthritis, multiple sclerosis, neuropathic pain, gout, and gouty arthritis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of inflammatory and autoimmune diseases.

The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

BRIEF DESCRIPTION OF THE DRAWINGS

The invention is illustrated by reference to the accompanying drawings described below.

DETAILED DESCRIPTION

Figure 1:
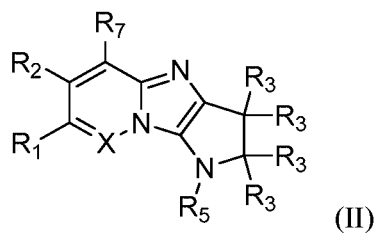
FIG. 1 shows the structures of the compounds of Formula (II); the compounds of Formula (III-a) and Formula (III-b); and the compounds of Formula (IV-a), Formula (IV-b), and Formula (IV-c).
Figure 1:
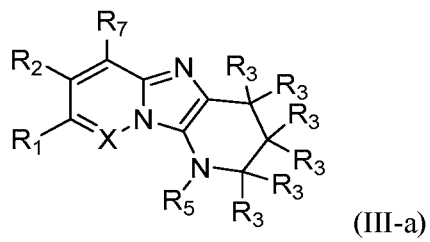
Figure 1:
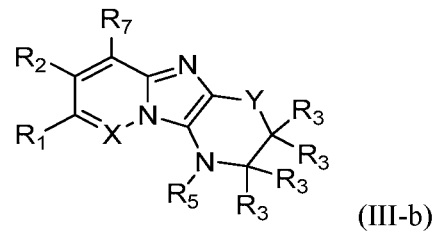
Figure 1:
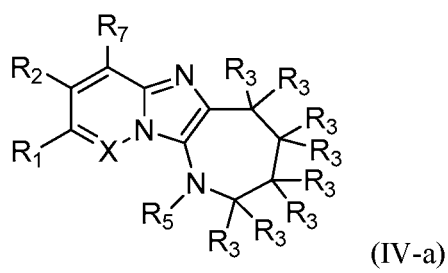
Figure 1:
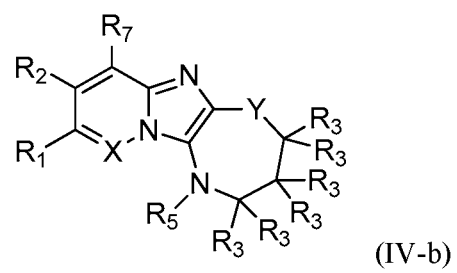
Figure 1:
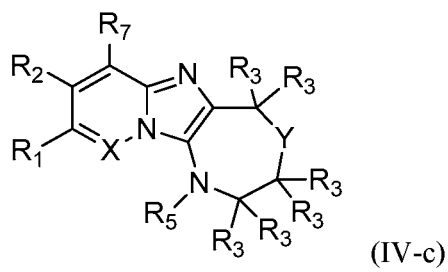
Figure 2:
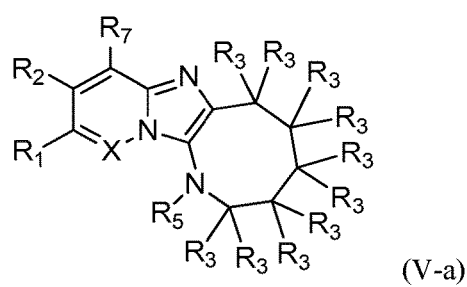
FIG. 2 shows the structures of the compounds of Formula (V-a), Formula (V-b), Formula (V-c), and Formula (V-d).
Figure 2:
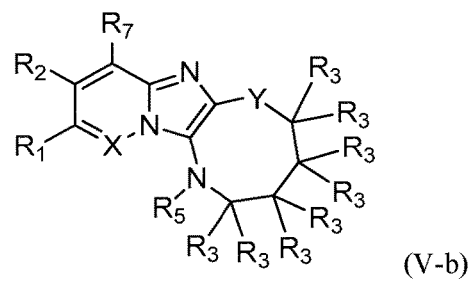
Figure 2:
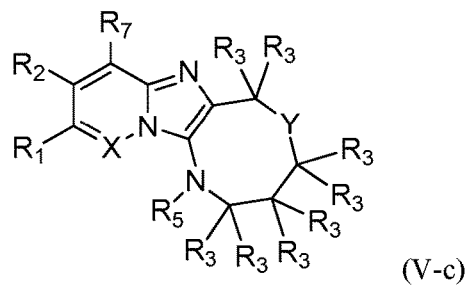
Figure 2:
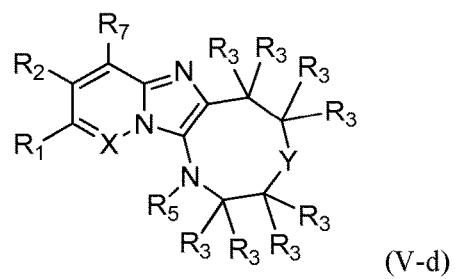

The first aspect of the present invention provides at least one compound of Formula (I):

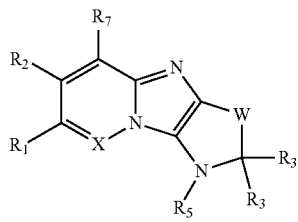

or salts thereof, wherein:
X is $CR_6$ or N;
W is:
  (i) $-(CR_3R_3)_{1-4}-$; or
  (ii) $-(CR_3R_3)_x-Y-(CR_3R_3)_y-$;
each Y is independently O, $NR_4$, or $S(O)_p$;
x is zero, 1, or 2;
y is 1, 2, or 3, provided that (x+y) is 1, 2, or 3;
$R_1$ is H, $R_{1a}$, $C_{1-6}$ haloalkyl, $C_{2-6}$ alkenyl substituted with zero to 6 $R_{1a}$, $C_{2-6}$ alkynyl substituted with zero to 4 $R_{1a}$, $-(CR_gR_g)_r$(3-14 membered carbocyclyl substituted with zero to 3 $R_{1a}$), $-(CR_gR_g)_r$(aryl substituted with zero to 3 $R_{1a}$), $-(CR_gR_g)_r$(5-7 membered heterocyclyl substituted with zero to 3 $R_{1a}$), or $-(CR_gR_g)_r$(mono- or bicyclic heteroaryl substituted with zero to 3 $R_{1a}$);
$R_2$ is H, halo, $-CN$, $-CF_3$, $-OCF_3$, $-NO_2$, $C_{1-6}$ alkyl substituted with zero to 6 $R_{1a}$, $-(CR_gR_g)_rOR_e$, $-(CR_gR_g)_rNR_cR_c$, $-(CR_gR_g)_rS(O)_pR_b$, $-(CR_gR_g)_r$(3-14 membered carbocyclyl substituted with zero to 3 $R_{1a}$), $-(CR_gR_g)_r$(aryl substituted with zero to 3 $R_{1a}$), $-(CR_gR_g)_r$(5-7 membered heterocyclyl substituted with zero to 3 $R_{1a}$), or $-(CR_gR_g)_r$(monocyclic heteroaryl substituted with zero to 3 $R_{1a}$);
each $R_3$ is independently H, halo, $-CN$, $-OH$, $-OCF_3$, $C_{1-6}$ alkyl, $C_{1-6}$ haloalkyl, $C_{2-6}$ alkenyl, $C_{2-6}$ alkynyl, $-(CR_gR_g)_rC(O)R_b$, $-(CR_gR_g)_rC(O)OR_b$, $-(CR_gR_g)_rC(O)NR_cR_c$, $-(CR_gR_g)_rOR_e$, $-(CR_gR_g)_rOC(O)R_b$, $-(CR_gR_g)_rOC(O)NR_cR_c$, $-(CR_gR_g)_rOC(O)OR_d$, $-(CR_gR_g)_rNR_cR_c$, $-(CR_gR_g)_rNR_bC(O)R_d$, $-(CR_gR_g)_rNR_bC(O)OR_d$, $-(CR_gR_g)_rNR_bC(O)NR_cR_c$, $-(CR_gR_g)_rNR_bS(O)_pR_d$, $-(CR_gR_g)_rS(O)_pR_b$, $-(CR_gR_g)_rS(O)_pNR_cR_c$, $-(CR_gR_g)_r$(3-14 membered carbocyclyl substituted with zero to 3 $R_{1a}$), $-(CR_gR_g)_r$(aryl substituted with zero to 3 $R_{1a}$), $-(CR_gR_g)_r$(5-7 membered heterocyclyl substituted with zero to 3 $R_{1a}$), or $-(CR_gR_g)_r$(mono- or bicyclic heteroaryl substituted with zero to 3 $R_{1a}$); or two $R_3$ along with the carbon atom to which they are attached form $C=O$, $C=NOR_b$, a spirocarbocyclyl ring, or a spiroheterocyclyl ring;
each $R_4$ is independently H, $C_{1-6}$ alkyl substituted with zero to 6 $R_{1a}$, $C_{3-7}$ cycloalkyl substituted with zero to 6 $R_{1a}$, $-C(O)R_b$, $-C(O)NR_cR_c$, $-C(O)OR_b$, $-S(O)_2R_b$, $-S(O)_2NR_cR_c$, $-S(O)_2OR_b$, $-(CR_gR_g)_r$(3-14 membered carbocyclyl substituted with zero to 3 $R_{1a}$), $-(CR_gR_g)_r$(aryl substituted with zero to 3 $R_{1a}$), $-(CR_gR_g)_r$(5-7 membered heterocyclyl substituted with zero to 3 $R_{1a}$), or $-(CR_gR_g)_r$(monocyclic heteroaryl substituted with zero to 3 $R_{1a}$);
$R_5$ is $-(CR_gR_g)_r$(3-14 membered carbocyclyl substituted with zero to 3 $R_{1a}$), $-(CR_gR_g)_r$(aryl substituted with zero to 3 $R_{1a}$), $-(CR_gR_g)_r$(5-10 membered heterocyclyl substituted with zero to 3 $R_{1a}$), or $-(CR_gR_g)_r$(mono- or bicyclic heteroaryl substituted with zero to 3 $R_{1a}$);
$R_6$ is H, halo, or $-CN$;
$R_7$ is H, halo, $-CN$, $C_{1-6}$ alkyl, or $C_{1-3}$ alkoxy;
each $R_{1a}$ is independently F, Cl, $-CN$, $C_{1-6}$ alkyl substituted with zero to 6 $R_a$, $C_{3-6}$ cycloalkyl substituted with zero to 6 $R_a$, $C_{1-3}$ alkoxy substituted with zero to 6 $R_a$, $C_{1-3}$ haloalkoxy, heterocycloalkyl substituted with zero to 6 $R_a$, aryl substituted with zero to 6 $R_a$, mono- or bicyclic heteroaryl substituted with zero to 6 $R_a$, $-C(O)R_b$, $-C(O)OR_b$, $-C(O)NR_cR_c$, $-OC(O)R_b$, $-OC(O)NR_cR_c$, $-OC(O)OR_d$, $-NR_cR_c$, $-NR_bC(O)R_d$, $-NR_bC(O)OR_d$, $-NR_bS(O)_pR_d$, $-NR_bC(O)NR_cR_c$, $-NR_bS(O)_pNR_cR_c$, $-S(O)_pR_b$, $-S(O)_pNR_cR_c$, or $-C(O)NR_b(CH_2)_{1-3}NR_cR_c$;
each $R_a$ is independently halo, $-CN$, $-OH$, $-NH_2$, $C_{1-3}$ alkyl, $C_{1-3}$ fluoroalkyl, $C_{2-4}$ alkenyl, $C_{2-4}$ alkynyl, $C_{1-3}$ alkoxy, $C_{1-3}$ fluoroalkoxy, $-C(O)OH$, $-C(O)(C_{1-3}$ alkyl), $-C(O)O(C_{1-4}$ alkyl), $-OC(O)(C_{1-3}$ alkyl), $-NH(C_{1-3}$ alkyl), $-N(C_{1-3}$ alkyl)$_2$, $-C(O)NH(C_{1-3}$ alkyl), $-OC(O)NH(C_{1-3}$ alkyl), $-NHC(O)NH(C_{1-3}$ alkyl), $-C(=NH)(NH_2)$, $C_{3-7}$ carbocyclyl, aryl, 5-7 membered heterocyclyl, mono- or bicyclic heteroaryl, $-O(aryl)$, $-O(benzyl)$, $-O(heterocyclyl)$, $-S(C_{1-3}$ alkyl), $-S(aryl)$, $-S(heterocyclyl)$, $-S(O)(aryl)$, $-S(O)(heterocyclyl)$, $-S(O)_2(aryl)$, $-S(O)_2(heterocyclyl)$, $-NHS(O)_2(aryl)$, $-NHS(O)_2(heterocyclyl)$, $-NHS(O)_2NH(aryl)$, $-NHS(O)_2NH(heterocyclyl)$, $-NH(aryl)$ $-NH(heterocyclyl)$, $-NHC(O)(aryl)$, $-NHC(O)(C_{1-3}$ alkyl), $-NHC(O)(heterocyclyl)$, $-OC(O)(aryl)$, $-OC(O)(heterocyclyl)$, $-NHC(O)NH(aryl)$, $-NHC(O)NH(heterocyclyl)$, $-OC(O)O(C_{1-3}$ alkyl), $-OC(O)O(aryl)$, $-OC(O)O(heterocyclyl)$, $-OC(O)NH(aryl)$, $-OC(O)NH(heterocyclyl)$, $-NHC(O)O(aryl)$, $-NHC(O)O(heterocyclyl)$, $-NHC(O)O(C_{1-3}$ alkyl), $-C(O)NH(aryl)$, $-C(O)NH(heterocyclyl)$, $-C(O)O(aryl)$, $-C(O)O(heterocyclyl)$, $-N(C_{1-3}$ alkyl)$S(O)_2(aryl)$, $-N(C_{1-3}$ alkyl)$S(O)_2(heterocyclyl)$, $-N(C_{1-3}$ alkyl)$S(O)_2NH(aryl)$, $-N(C_{1-3}$ alkyl)$S(O)_2NH(heterocyclyl)$, $-N(C_{1-3}$ alkyl)(aryl), $-N(C_{1-3}$ alkyl)(heterocyclyl), $-N(C_{1-3}$ alkyl)C(O)(aryl), $-N(C_{1-3}$ alkyl)C(O)(heterocyclyl), $-N(C_{1-3}$ alkyl)C(O)NH(aryl), $-(CH_2)_{0-3}C(O)NH(heterocyclyl)$, $-OC(O)N(C_{1-3}$ alkyl)(aryl), $-OC(O)N(C_{1-3}$ alkyl)(heterocyclyl), $-N(C_{1-3}$ alkyl)C(O)O(aryl), $-N(C_{1-3}$ alkyl)C(O)O(heterocyclyl), $-C(O)N(C_{1-3}$ alkyl)(aryl), —C(O)N($C_{1-3}$ alkyl)(heterocyclyl), —NHS(O)$_2$N($C_{1-3}$ alkyl)(aryl), —NHS(O)$_2$N($C_{1-3}$ alkyl)(heterocyclyl), —NHP(O)$_2$N($C_{1-3}$ alkyl)(aryl), —NHC(O)N($C_{1-3}$ alkyl)(aryl), —NHC(O)N($C_{1-3}$ alkyl)(heterocyclyl), —N($C_{1-3}$ alkyl)S(O)$_2$N($C_{1-3}$ alkyl)(aryl), —N($C_{1-3}$ alkyl)S(O)$_2$N($C_{1-3}$ alkyl)(heterocyclyl), —N($C_{1-3}$ alkyl)C(O)N($C_{1-3}$ alkyl)(aryl), —N($C_{1-3}$ alkyl)C(O)N($C_{1-3}$ alkyl)(heterocyclyl), or —Si($C_{1-3}$ alkyl)$_3$;

each $R_b$ is independently H, $C_{1-6}$ alkyl substituted with zero to 6 $R_f$, $C_{3-7}$ cycloalkyl substituted with zero to 6 $R_f$, heterocycloalkyl substituted with zero to 6 $R_f$, aryl substituted with zero to 3 $R_f$, or mono- or bicyclic heteroaryl substituted with zero to 3 $R_f$;

each $R_c$ is independently H, $C_{1-6}$ alkyl substituted with zero to 6 $R_f$, $C_{3-7}$ cycloalkyl substituted with zero to 6 $R_f$, heterocycloalkyl substituted with zero to 6 $R_f$, aryl substituted with zero to 3 $R_f$, or mono- or bicyclic heteroaryl substituted with zero to 3 $R_f$; or when attached to the same nitrogen, two $R_c$ along with the nitrogen atom to which they are attached form 4-8 membered heterocyclic ring optionally substituted with $R_g$;

each $R_d$ is independently H, $C_{1-6}$ alkyl substituted with zero to 6 $R_f$, $C_{3-7}$ cycloalkyl substituted with zero to 6 $R_f$, heterocycloalkyl substituted with zero to 6 $R_f$, aryl substituted with zero to 3 $R_f$, or mono- or bicyclic heteroaryl substituted with zero to 3 $R_f$;

each $R_e$ is independently H, $C_{1-6}$ alkyl substituted with zero to 6 $R_f$, $C_{1-3}$ haloalkyl, $C_{3-7}$ cycloalkyl substituted with zero to 6 $R_f$, heterocycloalkyl substituted with zero to 6 $R_f$, aryl substituted with zero to 3 $R_f$, or mono- or bicyclic heteroaryl substituted with zero to 3 $R_f$;

each $R_f$ is independently H, halo, —OH, —CN, $C_{1-6}$ alkyl substituted with zero to 6 $R_a$, $C_{1-3}$ alkoxy, $C_{3-7}$ cycloalkyl substituted with zero to 6 $R_a$, heterocycloalkyl substituted with zero to 6 $R_a$, aryl substituted with zero to 3 $R_a$, or mono- or bicyclic heteroaryl substituted with zero to 3 $R_a$;

each $R_g$ is independently H, F, —OH, —CN, $C_{1-3}$ alkyl, —CF$_3$, or phenyl;

each p is independently zero, 1, or 2; and each r is independently zero, 1, 2, 3, or 4.

One embodiment provides a compound of Formula (I) or a salt thereof, wherein X is CR$_6$ and W, R$_1$, R$_2$, R$_3$, R$_5$, R$_6$, and R$_7$ are defined in the first aspect. Included in this embodiment are compounds in which R$_6$ is H. Also included are compounds in which R$_7$ is H.

One embodiment provides a compound of Formula (I) or a salt thereof, wherein X is N and W, R$_1$, R$_2$, R$_3$, R$_5$, and R$_7$ are defined in the first aspect. Included in this embodiment are compounds in which R$_7$ is H.

One embodiment provides a compound of Formula (I) or a salt thereof, wherein X is CR$_6$; R$_6$ is H, F, or —CN; and W, R$_1$, R$_2$, R$_3$, R$_5$, and R$_7$ are defined in the first aspect. Included in this embodiment are compounds in which R$_6$ is F or —CN.

One embodiment provides a compound of Formula (I) or a salt thereof, wherein W is —CR$_3$R$_3$—; and X, R$_1$, R$_2$, R$_3$, R$_5$, R$_6$, and R$_7$ are defined in the first aspect. Compounds of this embodiment have the structure of compounds of Formula (II). Included in this embodiment are compounds in which X is CR$_6$. Also included in this embodiment are compounds in which X is N.

One embodiment provides a compound of Formula (I) or a salt thereof, wherein W is —(CR$_3$R$_3$)$_2$—; and X, R$_1$, R$_2$, R$_3$, R$_5$, R$_6$, and R$_7$ are defined in the first aspect. Compounds of this embodiment have the structure of compounds of Formula (III-a). Included in this embodiment are compounds in which X is CR$_6$. Also included in this embodiment are compounds in which X is N. Additionally, included in this embodiment are compounds in which W is —CH$_2$CH$_2$— and —CH(CH$_3$)CH$_2$—.

One embodiment provides a compound of Formula (I) or a salt thereof, wherein W is —Y—(CR$_3$R$_3$)—; and X, Y, R$_1$, R$_2$, R$_3$, R$_5$, R$_6$, and R$_7$ are defined in the first aspect. Compounds of this embodiment have the structure of compounds of Formula (III-b). Included in this embodiment are compounds in which X is CR$_6$. Also included in this embodiment are compounds in which X is N.

One embodiment provides a compound of Formula (I) or a salt thereof, wherein W is —(CR$_3$R$_3$)$_3$—; and X, R$_1$, R$_2$, R$_3$, R$_5$, R$_6$, and R$_7$ are defined in the first aspect. Compounds of this embodiment have the structure of compounds of Formula (IV-a). Included in this embodiment are compounds in which X is CR$_6$. Also included in this embodiment are compounds in which X is N.

One embodiment provides a compound of Formula (I) or a salt thereof, wherein W is —Y—(CR$_3$R$_3$)$_2$—; and X, Y, R$_1$, R$_2$, R$_3$, R$_5$, R$_6$, and R$_7$ are defined in the first aspect. Compounds of this embodiment have the structure of compounds of Formula (IV-b). Included in this embodiment are compounds in which X is CR$_6$. Also included in this embodiment are compounds in which X is N.

One embodiment provides a compound of Formula (I) or a salt thereof, wherein W is —CR$_3$R$_3$—Y—CR$_3$R$_3$—; and X, Y, R$_1$, R$_2$, R$_3$, R$_5$, R$_6$, and R$_7$ are defined in the first aspect. Compounds of this embodiment have the structure of compounds of Formula (IV-c). Included in this embodiment are compounds in which X is CR$_6$. Also included in this embodiment are compounds in which X is N.

One embodiment provides a compound of Formula (I) or a salt thereof, wherein W is —(CR$_3$R$_3$)$_4$—; and X, R$_1$, R$_2$, R$_3$, R$_5$, R$_6$, and R$_7$ are defined in the first aspect. Compounds of this embodiment have the structure of compounds of Formula (V-a). Included in this embodiment are compounds in which X is CR$_6$. Also included in this embodiment are compounds in which X is N.

One embodiment provides a compound of Formula (I) or a salt thereof, wherein W is —Y—(CR$_3$R$_3$)$_3$—; and X, Y, R$_1$, R$_2$, R$_3$, R$_5$, R$_6$, and R$_7$ are defined in the first aspect. Compounds of this embodiment have the structure of compounds of Formula (V-b). Included in this embodiment are compounds in which X is CR$_6$. Also included in this embodiment are compounds in which X is N.

One embodiment provides a compound of Formula (I) or a salt thereof, wherein W is —CR$_3$R$_3$—Y—(CR$_3$R$_3$)$_2$—; and X, Y, R$_1$, R$_2$, R$_3$, R$_5$, R$_6$, and R$_7$ are defined in the first aspect. Compounds of this embodiment have the structure of compounds of Formula (V-c). Included in this embodiment are compounds in which X is CR$_6$. Also included in this embodiment are compounds in which X is N.

One embodiment provides a compound of Formula (I) or a salt thereof, wherein W is —(CR$_3$R$_3$)$_2$—Y—CR$_3$R$_3$—; and X, Y, R$_1$, R$_2$, R$_3$, R$_5$, R$_6$, and R$_7$ are defined in the first aspect. Compounds of this embodiment have the structure of compounds of Formula (V-d). Included in this embodiment are compounds in which X is CR$_6$. Also included in this embodiment are compounds in which X is N.

One embodiment provides a compound of Formula (I) or a salt thereof, wherein W is —(CR$_3$R$_3$)$_{1-4}$—; and X, R$_1$, R$_2$, R$_3$, R$_5$, R$_6$, and R$_7$ are defined in the first aspect. Compounds of this embodiment have the structures of Formula (II), Formula (III-a), Formula (IV-a), and Formula (V-a). Included in this embodiment are compounds in which X is CR$_6$. Also included in this embodiment are compounds in which X is N.

One embodiment provides a compound of Formula (I) or a salt thereof, wherein W is $-(CR_3R_3)_x-Y-(CR_3R_3)_y-$; and X, Y, $R_1$, $R_2$, $R_3$, $R_5$, $R_6$, $R_7$, x, and y are defined in the first aspect. Compounds of this embodiment have the structures of Formula (III-b), Formula (IV-b), Formula (IV-c), Formula (V-b), Formula (V-c), and Formula (V-d). Included in this embodiment are compounds in which X is $CR_6$. Also included in this embodiment are compounds in which X is N.

One embodiment provides a compound of Formula (I) or a salt thereof, wherein W is $-(CR_3R_3)_2-$ or $-Y-CR_3R_3-$; and X, Y, $R_1$, $R_2$, $R_3$, $R_5$, $R_6$, and $R_7$ are defined in the first aspect. Included in this embodiment are the compounds of Formula (III-a) and Formula (III-b). Included in this embodiment are compounds in which X is $CR_6$. Also included in this embodiment are compounds in which X is N.

One embodiment provides a compound of Formula (I) or a salt thereof, wherein W is $-(CR_3R_3)_3-$, $-Y-(CR_3R_3)_2-$, or $-CR_3R_3-Y-CR_3R_3-$; and X, Y, $R_1$, $R_2$, $R_3$, $R_5$, $R_6$, and $R_7$ are defined in the first aspect. Included in this embodiment are the compounds of Formula (IV-a), Formula (IV-b), or Formula (IV-c). Included in this embodiment are compounds in which X is $CR_6$. Also included in this embodiment are compounds in which X is N.

One embodiment provides a compound of Formula (I) or a salt thereof, wherein W is $-(CR_3R_3)_4-$, $-Y-(CR_3R_3)_3-$, $-CR_3R_3-Y-(CR_3R_3)_2-$, or $-(CR_3R_3)_2-Y-CR_3R_3-$; and X, Y, $R_1$, $R_2$, $R_3$, $R_5$, $R_6$, and $R_7$ are defined in the first aspect. Included in this embodiment are the compounds of Formula (V-a), Formula (V-b), Formula (V-c), or Formula (V-d). Included in this embodiment are compounds in which X is $CR_6$. Also included in this embodiment are compounds in which X is N.

One embodiment provides a compound of Formula (I) or a salt thereof, wherein W is $-(CR_3R_3)_x-Y-(CR_3R_3)_y-$; Y is O; and X, $R_1$, $R_2$, $R_3$, $R_5$, $R_6$, $R_7$, x, and y are defined in the first aspect. Compounds of this embodiment have the structures of Formula (III-b), Formula (IV-b), Formula (IV-c), Formula (V-b), Formula (V-c), and Formula (V-d). Included in this embodiment are compounds in which X is $CR_6$. Also included in this embodiment are compounds in which X is N.

One embodiment provides a compound of Formula (I) or a salt thereof, wherein W is $-(CR_3R_3)_x-Y-(CR_3R_3)_y-$; Y is $NR_4$; and X, $R_1$, $R_2$, $R_3$, $R_4$, $R_5$, $R_6$, $R_7$, x, and y are defined in the first aspect. Compounds of this embodiment have the structures of Formula (III-b), Formula (IV-b), Formula (IV-c), Formula (V-b), Formula (V-c), and Formula (V-d). Included in this embodiment are compounds in which X is $CR_6$. Also included in this embodiment are compounds in which X is N.

One embodiment provides a compound of Formula (I) or a salt thereof, wherein W is $-(CR_3R_3)_x-Y-(CR_3R_3)_y-$; Y is $S(O)_p$; and X, $R_1$, $R_2$, $R_3$, $R_5$, $R_6$, $R_7$, p, x, and y are defined in the first aspect. Compounds of this embodiment have the structures of Formula (III-b), Formula (IV-b), Formula (IV-c), Formula (V-b), Formula (V-c), and Formula (V-d). Included in this embodiment are compounds in which X is $CR_6$. Also included in this embodiment are compounds in which X is N.

One embodiment provides a compound of Formula (I) or a salt thereof, wherein $R_1$ is H, $R_{1a}$, $C_{1-6}$ haloalkyl, $C_{2-6}$ alkenyl substituted with zero to 6 $R_{1a}$, or $C_{2-6}$ alkynyl substituted with zero to 4 $R_{1a}$; and X, W, $R_{1a}$, $R_2$, $R_3$, $R_5$, and $R_7$ are defined in the first aspect.

One embodiment provides a compound of Formula (I) or a salt thereof, wherein $R_1$ is $R_{1a}$; and X, W, $R_{1a}$, $R_2$, $R_3$, $R_5$, and $R_7$ are defined in the first aspect.

One embodiment provides a compound of Formula (I) or a salt thereof, wherein $R_1$ is: F, Cl, Br, —CN; and X, W, $R_{1a}$, $R_2$, $R_3$, $R_5$, and $R_7$ are defined in the first aspect.

One embodiment provides a compound of Formula (I) or a salt thereof, wherein $R_1$ is $C_{1-6}$ haloalkyl, $C_{2-6}$ alkenyl substituted with zero to 6 $R_{1a}$, or $C_{2-6}$ alkynyl substituted with zero to 4 $R_{1a}$; and X, W, $R_{1a}$, $R_2$, $R_3$, $R_5$, and $R_7$ are defined in the first aspect.

One embodiment provides a compound of Formula (I) or a salt thereof, wherein $R_1$ is $-(CR_gR_g)_r$(3-14 membered carbocyclyl substituted with zero to 3 $R_{1a}$), $-(CR_gR_g)_r$(aryl substituted with zero to 3 $R_{1a}$), $-(CR_gR_g)_r$(5-7 membered heterocyclyl substituted with zero to 3 $R_{1a}$), or $-(CR_gR_g)_r$(mono- or bicyclic heteroaryl substituted with zero to 3 $R_{1a}$); and X, W, $R_{1a}$, $R_2$, $R_3$, $R_5$, $R_7$, $R_g$, and r are defined in the first aspect. Included in this embodiment are compounds in which r is 1. Also included in this embodiment are compounds in which $R_1$ is $-CH_2$(3-14 membered carbocyclyl substituted with zero to 3 $R_{1a}$), $-CH_2$(aryl substituted with zero to 3 $R_{1a}$), $-CH_2$(5-7 membered heterocyclyl substituted with zero to 3 $R_{1a}$), or $-CH_2$(mono- or bicyclic heteroaryl substituted with zero to 3 $R_{1a}$).

One embodiment provides a compound of Formula (I) or a salt thereof, wherein $R_1$ is 3-14 membered carbocyclyl substituted with zero to 3 $R_{1a}$, aryl substituted with zero to 3 $R_{1a}$, 5-7 membered heterocyclyl substituted with zero to 3 $R_{1a}$, or mono- or bicyclic heteroaryl substituted with zero to 3 $R_{1a}$; and X, W, $R_{1a}$, $R_2$, $R_3$, $R_5$, and $R_7$ are defined in the first aspect. Also included in this embodiment are compounds in which $R_1$ is $-CH_2$(3-14 membered carbocyclyl substituted with zero to 3 $R_{1a}$), $-CH_2$(aryl substituted with zero to 3 $R_{1a}$), $-CH_2$(5-7 membered heterocyclyl substituted with zero to 3 $R_{1a}$), or $-CH_2$(mono- or bicyclic heteroaryl substituted with zero to 3 $R_{1a}$).

One embodiment provides a compound of Formula (I) or a salt thereof, wherein $R_2$ is H, halo, —CN, —$CF_3$, —$OCF_3$, —$NO_2$, or $C_{1-6}$ alkyl substituted with zero to 6 $R_{1a}$; and X, W, $R_{1a}$, $R_1$, $R_3$, $R_5$, and $R_7$ are defined in the first aspect. Included in this embodiment are compounds in which $R_2$ is H, halo, —CN, —$CH_3$, —$CF_3$, or —$OCF_3$. Also included in this embodiment are compounds in which $R_2$ is H, F, Cl, or —$CH_3$.

One embodiment provides a compound of Formula (I) or a salt thereof, wherein $R_2$ is $-(CR_gR_g)_rOR_e$, $-(CR_gR_g)_rNR_cR_c$, $-(CR_gR_g)_rS(O)_pR_b$, $-(CR_gR_g)_r$(3-14 membered carbocyclyl substituted with zero to 3 $R_{1a}$), $-(CR_gR_g)_r$(aryl substituted with zero to 3 $R_{1a}$), $-(CR_gR_g)_r$(5-7 membered heterocyclyl substituted with zero to 3 $R_{1a}$), or $-(CR_gR_g)_r$(monocyclic heteroaryl substituted with zero to 3 $R_{1a}$); and X, W, $R_1$, $R_3$, $R_5$, $R_7$, $R_{1a}$, $R_b$, $R_c$, $R_e$, $R_g$, p, and r are defined in the first aspect. Included in this embodiment are compounds in which r is 1. Also included in this embodiment are compounds in which $R_1$ is $-CH_2$(3-14 membered carbocyclyl substituted with zero to 3 $R_{1a}$), $-CH_2$(aryl substituted with zero to 3 $R_{1a}$), $-CH_2$(5-7 membered heterocyclyl substituted with zero to 3 $R_{1a}$), or $-CH_2$(mono- or bicyclic heteroaryl substituted with zero to 3 $R_{1a}$).

One embodiment provides a compound of Formula (I) or a salt thereof, wherein each $R_3$ is independently H, halo, —CN, —OH, —$OCF_3$, $C_{1-6}$ alkyl, $C_{1-6}$ haloalkyl, $C_{2-6}$ alkenyl, $C_{2-6}$ alkynyl, $-(CR_gR_g)_rC(O)R_b$, $-(CR_gR_g)_rC(O)OR_b$, $-(CR_gR_g)_rC(O)NR_cR_c$, $-(CR_gR_g)_rOR_e$, $-(CR_gR_g)_rOC(O)R_b$, $-(CR_gR_g)_rOC(O)NR_cR_c$, $-(CR_gR_g)_rOC(O)OR_d$, $-(CR_gR_g)_rNR_cR_c$, $-(CR_gR_g)_rNR_bC(O)R_d$, —$(CR_gR_g)_rNR_bC(O)OR_d$, —$(CR_gR_g)_rNR_bC(O)NR_cR_c$, —$(CR_gR_g)_rNR_bS(O)_pR_d$, —$(CR_gR_g)_rS(O)_pR_b$, —$(CR_gR_g)_rS(O)_pNR_cR_c$, —$(CR_gR_g)_r$(3-14 membered carbocyclyl substituted with zero to 3 $R_{1a}$), —$(CR_gR_g)_r$(aryl substituted with zero to 3 $R_{1a}$), —$(CR_gR_g)_r$(5-7 membered heterocyclyl substituted with zero to 3 $R_{1a}$), or —$(CR_gR_g)_r$(mono- or bicyclic heteroaryl substituted with zero to 3 $R_{1a}$); and X, W, $R_1$, $R_2$, $R_5$, $R_7$, $R_{1a}$, $R_b$, $R_c$, $R_d$, $R_e$, $R_g$, P, and r are defined in the first aspect.

One embodiment provides a compound of Formula (I) or a salt thereof, wherein each $R_3$ is independently H, halo, —CN, —OH, —$OCF_3$, $C_{1-6}$ alkyl, $C_{1-6}$ haloalkyl, $C_{2-6}$ alkenyl, or $C_{2-6}$ alkynyl; and X, W, $R_1$, $R_2$, $R_5$, and $R_7$ are defined in the first aspect. Included in this embodiment are compounds in which $R_3$ is H, —OH, —CN, —$OCF_3$, $C_{1-3}$ alkyl, or $C_{1-3}$ fluoroalkyl. Also included in this embodiment are compounds in which $R_3$ is H, —OH, —CN, —$OCF_3$, —$CH_3$, and —$CF_3$.

One embodiment provides a compound of Formula (I) or a salt thereof, wherein each $R_3$ is independently H, —$(CR_gR_g)_rC(O)R_b$, —$(CR_gR_g)_rC(O)OR_b$, —$(CR_gR_g)_rC(O)NR_cR_c$, —$(CR_gR_g)_rOR_e$, —$(CR_gR_g)_rOC(O)R_b$, —$(CR_gR_g)_rOC(O)NR_cR_c$, —$(CR_gR_g)_rOC(O)OR_d$, —$(CR_gR_g)_rNR_cR_c$, —$(CR_gR_g)_rNR_bC(O)R_d$, —$(CR_gR_g)_rNR_bC(O)OR_d$, —$(CR_gR_g)_rNR_bC(O)NR_cR_c$, —$(CR_gR_g)_rNR_bS(O)_pR_d$, —$(CR_gR_g)_rS(O)_pR_b$, or —$(CR_gR_g)_rS(O)_pNR_cR_c$; and X, W, $R_1$, $R_2$, $R_5$, $R_7$, $R_b$, $R_c$, $R_d$, $R_e$, $R_g$, p, and r are defined in the first aspect. Included in this embodiment are compounds in which each $R_g$ is H or —$CH_3$.

One embodiment provides a compound of Formula (I) or a salt thereof, wherein each $R_3$ is independently H, —$(CR_gR_g)_r$(3-14 membered carbocyclyl substituted with zero to 3 $R_{1a}$), —$(CR_gR_g)_r$(aryl substituted with zero to 3 $R_{1a}$), —$(CR_gR_g)_r$(5-7 membered heterocyclyl substituted with zero to 3 $R_{1a}$), or —$(CR_gR_g)_r$(mono- or bicyclic heteroaryl substituted with zero to 3 $R_{1a}$); and X, W, $R_1$, $R_2$, $R_5$, $R_7$, $R_{1a}$, $R_g$, and r are defined in the first aspect.

One embodiment provides a compound of Formula (I) or a salt thereof, wherein two $R_3$ along with the carbon atom to which they are attached form C=O, C=$NOR_b$, a spirocarbocyclyl group, or a spiroheterocyclyl group; the remaining $R_3$ are H, —OH, or —$CH_3$; and X, W, $R_1$, $R_2$, $R_5$, $R_7$, and $R_b$ are defined in the first aspect.

One embodiment provides a compound of Formula (I) or a salt thereof, wherein each $R_3$ is independently H, —OH, or —$CH_3$; and X, W, $R_1$, $R_2$, $R_5$, and $R_7$ are defined in the first aspect.

One embodiment provides a compound of Formula (I) or a salt thereof, wherein W is —$(CR_3R_3)_x$—Y—$(CR_3R_3)_y$—; Y is $NR_4$; $R_4$ is H, $C_{1-6}$ alkyl substituted with zero to 6 $R_{1a}$, or $C_{3-7}$ cycloalkyl substituted with zero to 6 $R_{1a}$; and X, $R_1$, $R_{1a}$, $R_2$, $R_3$, $R_5$, $R_7$, x, and y are defined in the first aspect.

One embodiment provides a compound of Formula (I) or a salt thereof, wherein W is —$(CR_3R_3)_x$—Y—$(CR_3R_3)_y$—; Y is $NR_4$; $R_4$ is —$C(O)R_b$, —$C(O)NR_cR_c$, —$C(O)OR_b$, —$S(O)_2R_b$, —$S(O)_2NR_cR_c$, or —$S(O)_2OR_b$; and X, $R_1$, $R_2$, $R_3$, $R_5$, $R_7$, $R_b$, $R_c$, x, and y are defined in the first aspect.

One embodiment provides a compound of Formula (I) or a salt thereof, wherein W is —$(CR_3R_3)_x$—Y—$(CR_3R_3)_y$—; Y is $NR_4$; $R_4$ is —$(CR_gR_g)_r$(3-14 membered carbocyclyl substituted with zero to 3 $R_{1a}$), —$(CR_gR_g)_r$(aryl substituted with zero to 3 $R_{1a}$), —$(CR_gR_g)_r$(5-7 membered heterocyclyl substituted with zero to 3 $R_{1a}$), or —$(CR_gR_g)_r$(monocyclic heteroaryl substituted with zero to 3 $R_{1a}$); and X, $R_1$, $R_{1a}$, $R_2$, $R_3$, $R_5$, $R_7$, $R_{1a}$, r, x, and y are defined in the first aspect.

One embodiment provides a compound of Formula (I) or a salt thereof, wherein $R_5$ is —$(CR_gR_g)_r$(3-14 membered carbocyclyl substituted with zero to 3 $R_{1a}$) or —$(CR_gR_g)_r$(aryl substituted with zero to 3 $R_{1a}$); and X, W, $R_1$, $R_{1a}$, $R_2$, $R_3$, $R_7$, $R_g$, and r are defined in the first aspect. Included in this embodiment are compounds in which $R_5$ is —$(CR_gR_g)_r$(aryl substituted with zero to 3 $R_{1a}$). Also included in this embodiment are compounds in which each $R_g$ is H or —OH.

One embodiment provides a compound of Formula (I) or a salt thereof, wherein $R_5$ is —$(CR_gR_g)_r$(phenyl substituted with zero to 3 $R_{1a}$); and X, W, $R_1$, $R_{1a}$, $R_2$, $R_3$, $R_4$, $R_7$, $R_g$, and r are defined in the first aspect. Included in this embodiment are compounds in which $R_5$ is —$(CH_2)_r$(phenyl substituted with zero to 3 $R_{1a}$). Also included in this embodiment are compounds in which $R_5$ is phenyl substituted with zero to 3 $R_{1a}$.

One embodiment provides a compound of Formula (I) or a salt thereof, wherein $R_5$ is —$(CR_gR_g)_r$(5-10 membered heterocyclyl substituted with zero to 3 $R_{1a}$) or —$(CR_gR_g)_r$(mono- or bicyclic heteroaryl substituted with zero to 3 $R_{1a}$); and X, W, $R_1$, $R_{1a}$, $R_2$, $R_3$, $R_4$, $R_7$, $R_g$, and r are defined in the first aspect. Included in this embodiment are compounds in which $R_5$ is —$(CR_gR_g)_r$(mono- or bicyclic heteroaryl substituted with zero to 3 $R_{1a}$). Also included in this embodiment are compounds in which each $R_g$ is H.

One embodiment provides a compound of Formula (I) or a salt thereof, wherein $R_6$ is H, F, Cl, or —CN; and W, X, $R_1$, $R_2$, $R_3$, $R_5$, and $R_7$ are defined in the first aspect. Included in this embodiment are compounds in which $R_6$ is H or F. Also included in this embodiment are compounds in which $R_6$ is H.

One embodiment provides a compound of Formula (I) or a salt thereof, wherein $R_7$ is H, halo, or —CN; and X, W, $R_1$, $R_2$, $R_3$, and $R_5$ are defined in the first aspect. Included in this embodiment are compounds in which $R_7$ is H, F, Cl, or —CN. Also included in this embodiment are compounds in which $R_7$ is H, F, or —CN.

One embodiment provides a compound of Formula (I) or a salt thereof, wherein $R_7$ is H, $C_{1-6}$ haloalkyl, or $C_{1-3}$ alkoxy; and X, W, $R_1$, $R_2$, $R_3$, and $R_5$ are defined in the first aspect. Included in this embodiment are compounds in which $R_7$ is H, $C_{1-3}$ haloalkyl, or $C_{1-3}$ alkoxy. Also included in this embodiment are compounds in which $R_7$ is $C_{1-6}$ haloalkyl, or $C_{1-3}$ alkoxy.

One embodiment provides a compound of Formula (I) or a salt thereof, wherein $R_7$ is H, $C_{1-6}$ fluoroalkyl, or $C_{1-3}$ alkoxy; and X, W, $R_1$, $R_2$, $R_3$, and $R_5$ are defined in the first aspect. Included in this embodiment are compounds in which $R_7$ is H, $C_{1-3}$ fluoroalkyl, or $C_{1-3}$ alkoxy. Also included in this embodiment are compounds in which $R_7$ is $C_{1-6}$ fluoroalkyl, or $C_{1-3}$ alkoxy.

One embodiment provides a compound of Formula (I) or a salt thereof, wherein $R_7$ is H, F, Cl, —CN, $C_{1-2}$ fluoroalkyl, or $C_{1-3}$ alkoxy; and X, W, $R_1$, $R_2$, $R_3$, $R_3$, and $R_5$ are defined in the first aspect. Included in this embodiment are compounds in which $R_7$ is H, F, —CN, —$CF_3$, or —$OCH_3$. Also included in this embodiment are compounds in which $R_7$ is H, F, or —$CF_3$.

One embodiment provides a compound of Formula (I) or a salt thereof, wherein X is $CR_6$; W is —$(CR_3R_3)_{1-2}$—; $R_1$ is aryl substituted with zero to 3 $R_{1a}$ or mono- or bicyclic heteroaryl substituted with zero to 3 $R_{1a}$; $R_2$ is H, F, Cl, or $C_{1-3}$ alkyl; each $R_3$ is independently H, —OH, or —$CH_3$; $R_5$ is phenyl, pyridinyl, pyrimidinyl, isoquinolinyl, indolyl, isoindolinonyl, benzoimidazolyl, or benzothiazolyl, each substituted with 0 to 3 substituents independently selected from F, Cl, —CN, $C_{1-3}$ alkyl, $C_{1-3}$ fluoroalkyl, $C_{1-3}$ alkoxy, or $C_{1-3}$ fluoroalkoxy; $R_6$ is H or —$CH_3$; each $R_{1a}$ is independently F, Cl, —CN, $C_{1-3}$ alkyl substituted with zero to 6

$R_a$, $C_{1-3}$ alkoxy, $C_{1-3}$ fluoroalkoxy, morpholinyl, or methyloxadiazolyl; and each $R_a$ is independently F, —OH, —CN, or —NH$_2$.

One embodiment provides a compound of Formula (I) or a salt thereof, wherein W is —(CR$_3$R$_3$)$_2$—; X is CR$_6$; and $R_1$, $R_2$, $R_3$, $R_5$, $R_6$, and $R_7$ are defined in the first aspect. Included in this embodiment are compounds in which W is —CH$_2$CH$_2$—, —CH(CH$_3$)CH$_2$—, or —CH$_2$CH(CH$_3$)—. Also included in this embodiment are compounds in which W is —CH$_2$CH$_2$— or —CH(CH$_3$)CH$_2$—.

One embodiment provides a compound of Formula (I) or a salt thereof, wherein: X is CR$_6$; W is —(CR$_3$R$_3$)$_2$—; $R_1$ is phenyl, pyrazolyl, pyridinyl, or pyrimidinyl, each substituted with —CH$_3$, —OCH$_3$, —C(CH$_3$)$_2$OH, morpholinyl, or methyloxadiazolyl; $R_2$ is H, Cl, or —CH$_3$; each $R_3$ is H or —CH$_3$; $R_5$ is phenyl substituted with 0 to 2 substituents independently selected from F, Cl, —CH$_3$, —CH$_2$CH$_3$, —CF$_3$, —OCH$_3$, —OCHF$_2$, and —OCF$_3$; or isoquinolinyl; and $R_6$ is H.

One embodiment provides a compound of Formula (I) or a salt thereof, wherein: X is CR$_6$; W is —CH$_2$CH$_2$— or —CH(CH$_3$)CH$_2$—; $R_1$ is phenyl, pyrazolyl, pyridinyl, or pyrimidinyl, each substituted with —CH$_3$, —OCH$_3$, —C(CH$_3$)$_2$OH, morpholinyl, or methyloxadiazolyl; $R_2$ is H, Cl, or —CH$_3$; $R_5$ is phenyl substituted with 0 to 2 substituents independently selected from F, Cl, —CH$_3$, —CH$_2$CH$_3$, —CF$_3$, —OCH$_3$, —OCHF$_2$, and —OCF$_3$; or isoquinolinyl; and $R_6$ is H.

One embodiment provides a compound of Formula (I) or a salt thereof, wherein said compound is 1-(2,5-dimethylphenyl)-8-(6-methoxypyridin-3-yl)-7-methyl-1,2,3,4-tetrahydroimidazo[1,2-a:5,4-b']dipyridine (1); 1-(2-(difluoromethoxy)phenyl)-8-(6-methoxypyridin-3-yl)-7-methyl-1,2,3,4-tetrahydroimidazo[1,2-a:5,4-b']dipyridine (2); 1-(2,5-dimethylphenyl)-7-methyl-8-(1-methyl-1H-pyrazol-4-yl)-1,2,3,4-tetrahydroimidazo [1,2-a:5,4-b']dipyridine (3); 1-(2-(difluoromethoxy)phenyl)-7-methyl-8-(1-methyl-1H-pyrazol-4-yl)-1,2,3,4-tetrahydroimidazo[1,2-a:5,4-b']dipyridine (4); 1-(2,5-dimethylphenyl)-8-(6-methoxypyridin-3-yl)-1,2,3,4-tetrahydroimidazo[1,2-a:5,4-b']dipyridine (5); 1-(2-(difluoromethoxy)phenyl)-8-(6-methoxypyridin-3-yl)-1,2,3,4-tetrahydroimidazo[1,2-a:5,4-b']dipyridine (6); 1-(2-methoxy-5-methylphenyl)-8-(6-methoxypyridin-3-yl)-1,2,3,4-tetrahydroimidazo[1,2-a:5,4-b']dipyridine (7); 1-(isoquinolin-1-yl)-8-(6-methoxypyridin-3-yl)-1,2,3,4-tetrahydroimidazo[1,2-a:5,4-b']dipyridine (8); 8-(6-methoxypyridin-3-yl)-1-(o-tolyl)-1,2,3,4-tetrahydroimidazo [1,2-a:5,4-b']dipyridine (9); 8-(6-methoxypyridin-3-yl)-1-(2-(trifluoromethoxy)phenyl)-1,2,3,4-tetrahydroimidazo[1,2-a:5,4-b']dipyridine (10); 8-(6-methoxypyridin-3-yl)-1-(2-methyl-5-(trifluoromethyl)phenyl)-1,2,3,4-tetrahydroimidazo[1,2-a:5,4-b']dipyridine (11); 1-(2,5-dimethylphenyl)-8-(1-methyl-1H-pyrazol-4-yl)-1,2,3,4-tetrahydroimidazo [1,2-a:5,4-b']dipyridine (12); 1-(2-(difluoromethoxy)phenyl)-8-(1-methyl-1H-pyrazol-4-yl)-1,2,3,4-tetrahydroimidazo[1,2-a:5,4-b']dipyridine (13); 4-(5-(1-(2,5-dimethylphenyl)-1,2,3,4-tetrahydroimidazo[1,2-a:5,4-b']dipyridin-8-yl)pyrimidin-2-yl)morpholine (14); 4-(5-(1-(2-(difluoromethoxy)phenyl)-1,2,3,4-tetrahydroimidazo[1,2-a:5,4-b']dipyridin-8-yl)pyrimidin-2-yl)morpholine (15); 2-(4-(1-(2,5-dimethylphenyl)-1,2,3,4-tetrahydroimidazo[1,2-a:5,4-b']dipyridin-8-yl)phenyl)-5-methyl-1,3,4-oxadiazole (16); 2-(4-(1-(2-(difluoromethoxy)phenyl)-1,2,3,4-tetrahydroimidazo[1,2-a:5,4-b']dipyridin-8-yl)phenyl)-5-methyl-1,3,4-oxadiazole (17); 2-(5-(1-(2,5-dimethylphenyl)-1,2,3,4-tetrahydroimidazo[1,2-a:5,4-b']dipyridin-8-yl)pyrimidin-2-yl)propan-2-ol (18); 4-(5-(1-(2-(difluoromethoxy)-5-methylphenyl)-1,2,3,4-tetrahydroimidazo[1,2-a:5,4-b']dipyridin-8-yl)pyrimidin-2-yl)morpholine (19); 1-(2-(difluoromethoxy)-5-methylphenyl)-8-(6-methoxypyridin-3-yl)-1,2,3,4-tetrahydroimidazo[1,2-a:5,4-b']dipyridine (20); 2-(5-(7-chloro-1-phenyl-1,2,3,4-tetrahydroimidazo[1,2-a:5,4-b']dipyridin-8-yl)pyrimidin-2-yl)propan-2-ol (21); 7-chloro-1-(2-(difluoromethoxy)phenyl)-8-(6-methoxypyridin-3-yl)-1,2,3,4-tetrahydroimidazo[1,2-a:5,4-b']dipyridine (22); 7-chloro-1-(2,5-dimethylphenyl)-8-(6-methoxypyridin-3-yl)-1,2,3,4-tetrahydroimidazo[1,2-a:5,4-b']dipyridine (23); 1-(2,3-dimethylphenyl)-8-(6-methoxypyridin-3-yl)-1,2,3,4-tetrahydroimidazo[1,2-a:5,4-b']dipyridine (24); 1-(5-fluoro-2-methylphenyl)-8-(6-methoxypyridin-3-yl)-1,2,3,4-tetrahydroimidazo[1,2-a:5,4-b']dipyridine (25); 1-(4-fluoro-2-methylphenyl)-8-(6-methoxypyridin-3-yl)-1,2,3,4-tetrahydroimidazo[1,2-a:5,4-b']dipyridine (26); 1-(2-methoxy-5-methylphenyl)-8-(6-methoxypyridin-3-yl)-1,2,3,4-tetrahydroimidazo [1,2-a:5,4-b']dipyridine (27); 1-(2-ethylphenyl)-8-(6-methoxypyridin-3-yl)-1,2,3,4-tetrahydroimidazo[1,2-a:5,4-b']dipyridine (28); 8-(6-methoxypyridin-3-yl)-1-(2-(trifluoromethoxy)phenyl)-1,2,3,4-tetrahydroimidazo[1,2-a:5,4-b']dipyridine (29); 1-(2,4-dimethylphenyl)-8-(6-methoxypyridin-3-yl)-1,2,3,4-tetrahydroimidazo[1,2-a:5,4-b']dipyridine (30); 1-(2-chlorophenyl)-8-(6-methoxypyridin-3-yl)-1,2,3,4-tetrahydroimidazo [1,2-a:5,4-b']dipyridine (31); 1-(5-chloro-2-methylphenyl)-8-(6-methoxypyridin-3-yl)-1,2,3,4-tetrahydroimidazo[1,2-a:5,4-b']dipyridine (32); 4-(5-(1-(2,5-dimethylphenyl)-1,2,3,4-tetrahydroimidazo[1,2-a:5,4-b']dipyridin-8-yl)pyrimidin-2-yl)morpholine (33); 2-(5-(1-(2-(difluoromethoxy)phenyl)-1,2,3,4-tetrahydroimidazo[1,2-a:5,4-b']dipyridin-8-yl)pyrimidin-2-yl)propan-2-ol (34); 2-(4-(1-(2-(difluoromethoxy)phenyl)-1,2,3,4-tetrahydroimidazo[1,2-a:5,4-b']dipyridin-8-yl)phenyl)propan-2-ol (35); 2-(4-(1-(2,5-dimethylphenyl)-1,2,3,4-tetrahydroimidazo[1,2-a:5,4-b']dipyridin-8-yl)phenyl)propan-2-ol (36); 1-(2,5-dimethylphenyl)-8-(6-methoxypyridin-3-yl)-4-methyl-1,2,3,4-tetrahydroimidazo[1,2-a:5,4-b']dipyridine (37); 1-(2-(difluoromethoxy)phenyl)-8-(6-methoxypyridin-3-yl)-4-methyl-1,2,3,4-tetrahydroimidazo[1,2-a:5,4-b']dipyridine (38); 1-(2,5-dimethylphenyl)-4-methyl-8-(1-methyl-1H-pyrazol-4-yl)-1,2,3,4-tetrahydroimidazo [1,2-a:5,4-b']dipyridine (39); 1-(2-(difluoromethoxy)phenyl)-4-methyl-8-(1-methyl-1H-pyrazol-4-yl)-1,2,3,4-tetrahydroimidazo[1,2-a:5,4-b']dipyridine (40); or 4-(5-(1-(2,5-dimethylphenyl)-6,7-dimethyl-1,2,3,4-tetrahydroimidazo[1,2-a:5,4-b']dipyridin-8-yl)pyrimidin-2-yl)morpholine (41).

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I); and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen", as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "haloalkyl" as used herein is intended to include both branched and straight-chain saturated aliphatic hydrocarbon groups substituted with one or more halogen atoms. For example, "$C_{1-4}$ haloalkyl" is intended to include $C_1$, $C_2$, $C_3$, and $C_4$ alkyl groups substituted with one or more halogen atoms. Representative examples of haloalkyl groups include, but are not limited to, —CF$_3$, —CCl$_3$, —CFCl$_2$, and —CH$_2$CF$_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and $C_{1-4}$ cyanoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms. The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl", as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "cycloalkenyl", as used herein, refers to a nonaromatic cyclic hydrocarbon ring having one double bond. For example, $C_{5-6}$ cycloalkenyl denotes cyclopentenyl and cyclohexenyl.

The term "cycloalkynyl", as used herein, refers to a nonaromatic cyclic hydrocarbon ring having one triple bond. For example, $C_{5-6}$ cycloalkynyl denotes cyclopentynyl and cyclohexynyl.

The term "alkoxy", as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "carbocyclo" or "carbocyclyl" may be used interchangeably and refer to cyclic groups having at least one saturated or partially saturated non-aromatic ring wherein all atoms of all rings are carbon. The carbocyclyl ring may be unsubstituted or may contain one or more substituents as valence allows. Thus, the term includes nonaromatic rings such as, for example, cycloalkyl, cycloalkenyl, and cycloalkynyl rings. Exemplary bicyclic carbocyclyl groups include, indanyl, indenyl, dihydronaphthalenyl, tetrahydronaphthenyl, hexahydronaphthalenyl, octahydronaphthalenyl, decahydronaphthalenyl, bicycloheptanyl, bicyclooctanyl, and bicyclononanyl.

The term "aryl" as used herein, refers to a group of atoms derived from a molecule containing aromatic ring(s) by removing one hydrogen that is bonded to the aromatic ring(s). Heteroaryl groups that have two or more rings must include only aromatic rings. Representative examples of aryl groups include, but are not limited to, phenyl and naphthyl. The aryl ring may be unsubstituted or may contain one or more substituents as valence allows.

The term "benzyl", as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The term "heterocyclo" or "heterocyclyl" may be used interchangeably and refer to cyclic groups having at least saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The term "spirocarbocyclo", "spirocarbocyclic", or "spirocarbocyclyl" refers to a carbocyclyl ring attached to the molecular moiety by a carbon atom in the carbocyclyl ring that is shared with the molecular moiety.

The term "spiroheterocyclo", "spiroheterocyclic", or "spiroheterocyclyl" refers to a heterocyclyl ring attached to the molecular moiety by a carbon atom in the heterocyclyl ring that is shared with the molecular moiety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example, when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) Wermuth, C. G. et al., *The Practice of Medicinal Chemistry*, Chapter 31, Academic Press (1996);
b) Bundgaard, H. ed., *Design of Prodrugs*, Elsevier (1985);
c) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991); and
d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TNFα, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example, heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions can be presented in a pack or dispenser device which can contain one or more unit dosage forms including the compound of Formula (I). The pack can, for example, comprise metal or plastic foil, such as a blister pack. The pack or dispenser device can be accompanied by instructions for administration.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two-day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The pharmaceutical compositions may contain other therapeutic agents and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Utility

The compounds of the invention modulate the activity of TNFα. Accordingly, compounds of Formula (I) have utility in treating conditions associated with the modulation of TNFα.

The compounds in accordance with the present invention are beneficial in the treatment and/or prevention of various human ailments. The compounds in accordance with the present invention can be beneficial either as a standalone therapy or in combination with other therapies that therapeutically could provide greater benefit. The ailments for which the compounds in the present invention could be of benefit include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus, psoriasis, psoriatic arthropathy, vasculitis, polymyositis, scleroderma, multiple sclerosis, systemic sclerosis, ankylosing spondylitis, rheumatoid arthritis, psoriatic arthritis, non-specific inflammatory arthritis, juvenile inflammatory arthritis, juvenile idiopathic arthritis (including oligoarticular and polyarticular forms thereof), anemia of chronic disease, Still's disease (juvenile and/or adult onset), Behcet's disease and Sjögren's syndrome. Autoimmune endocrine disorders include thyroiditis. Organ-specific autoimmune disorders include Addison's disease, hemolytic or pernicious anemia, acute kidney injury, diabetic nephropathy, obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis, minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease, respiratory distress syndrome, sepsis, fever, muscular dystrophy (including Duchenne muscular dystrophy), and organ transplant rejection (including kidney allograft rejection).

Neurological and neurodegenerative disorders include Alzheimer's disease, Parkinson's disease, Huntington's disease, ischemia, stroke, amyotrophic lateral sclerosis, spinal cord injury, head trauma, seizures, and epilepsy.

Cardiovascular disorders include thrombosis, cardiac hypertrophy, hypertension, irregular contractility of the heart (e.g., during heart failure), and myocardial infarction.

Metabolic disorders include diabetes (including insulin-dependent diabetes mellitus and juvenile diabetes), dyslipidemia, and metabolic syndrome.

Ocular disorders include retinopathy (including diabetic retinopathy, proliferative retinopathy, non-proliferative retinopathy and retinopathy of prematurity), macular edema (including diabetic macular edema), age-related macular degeneration, vascularization (including corneal vascularization and neovascularization), retinal vein occlusion, and various forms of uveitis and keratitis.

Oncological disorders, which may be acute or chronic, include proliferative disorders, especially cancer, and cancer-associated complications (including skeletal complications, cachexia and anemia). Particular categories of cancer include hematological malignancy (including leukemia and lymphoma) and non-hematological malignancy (including solid tumor cancer, sarcoma, meningioma, glioblastoma multiform, neuroblastoma, melanoma, gastric carcinoma and renal cell carcinoma). Chronic leukemia may be myeloid or lymphoid.

One embodiment provides a method of treating a disorder selected from autoimmune and inflammatory disorders; neurological and neurodegenerative disorders; pain and nociceptive disorders; cardiovascular disorders; metabolic disorders; ocular disorders; and oncological disorders, comprising administering to a mammalian patient in need of treatment, a compound according to claim 1 or a pharmaceutically acceptable salt thereof. Preferably, the patient is human. For example, a therapeutically effective amount for treating a disorder may be administered in the method of the present embodiment.

One embodiment provides a method of treating a disease or disorder associated with the activity of TNFα, comprising administering to a mammalian patient in need of treatment, a compound according to claim 1 or a pharmaceutically acceptable salt thereof. Preferably, the patient is human. For example, a therapeutically effective amount for treating a disorder may be administered in the method of the present embodiment.

One embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment or prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of cancer.

The present invention provides the use of compounds of Formula (I) as pharmacological tools in the search for new pharmacological agents or in the development of new biological assays. In one embodiment, the compounds of Formula (I) are useful as radioligands or can be coupled to a fluorophore and utilized in assays to identify pharmacologically active compounds.

In one embodiment, the compounds of Formula (I) inhibit TNFα functional activity with $IC_{50}$ values of less than 10 µM, for example, from 0.001 to less than 10 µM, as measured by the TNF induced HEK-Blue assay. Preferably, the compounds of Formula (I) inhibit TNFα functional activity with $IC_{50}$ values of less than 1 µM, for example, from 0.001 to less than 1 µM. Other preferred compounds inhibit TNFα functional activity with $IC_{50}$ values of 100 nM and less, for example, from 1 to 100 nM.

Examples of compounds of Formula (I) as specified in the "Examples" section below, have been tested in one or more of the assays described below.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Scheme 1 illustrates a general synthesis of compounds 6, including imidazo[1,2-a]pyridines wherein Z=CH and imidazo[1,2-b]pyridazines wherein Z=N. The reaction of substituted aminopyridines or substituted aminopyrazines 1 with N-protected heterocyclic ketones 2 wherein n=1-3, such as, but not limited to, tert-butyl 3-oxopiperidine-1-carboxylate, in the presence of a catalytic amount of a weak acid, such as acetic acid, affords fused-tricyclic heterocycles of structure 3. The formation of compounds 3 requires prolonged heating (24-72 hours) in an appropriate solvent, such as toluene, that facilitates azeotropic removal of water using a Dean-Stark apparatus, and concomitant exposure to atmospheric oxygen. Compounds 3 can then be reacted with different boronic acids or boronic acid esters ($R_1$—$B(OR)_2$) under standard Suzuki coupling conditions, using a palladium catalyst such as $PdCl_2$(dppf), to synthesize compounds 4, where $R_1$ represents various aryl and heteroaryl groups. Removal of the tert-butyloxycarbonyl protecting group using standard conditions known to one skilled in the art, such as trifluoroacetic acid in dichloromethane, affords compounds of structure 5. Palladium-catalyzed C—N cross-coupling of compounds 5 with various aryl- and heteroaryl halides ($R_5$—X) under Buchwald-Hartwig conditions provides compounds of general structure 6. The 2nd generation RuPhos precatalyst, also known as chloro(2-dicyclohexylphosphino-2',6'-diisopropoxy-1,1'-biphenyl)[2-(2'-amino-1, 1'-biphenyl)]palladium(II), in combination with RuPhos and sodium tert-butoxide is particularly useful in affecting the N-arylation of compounds 5.

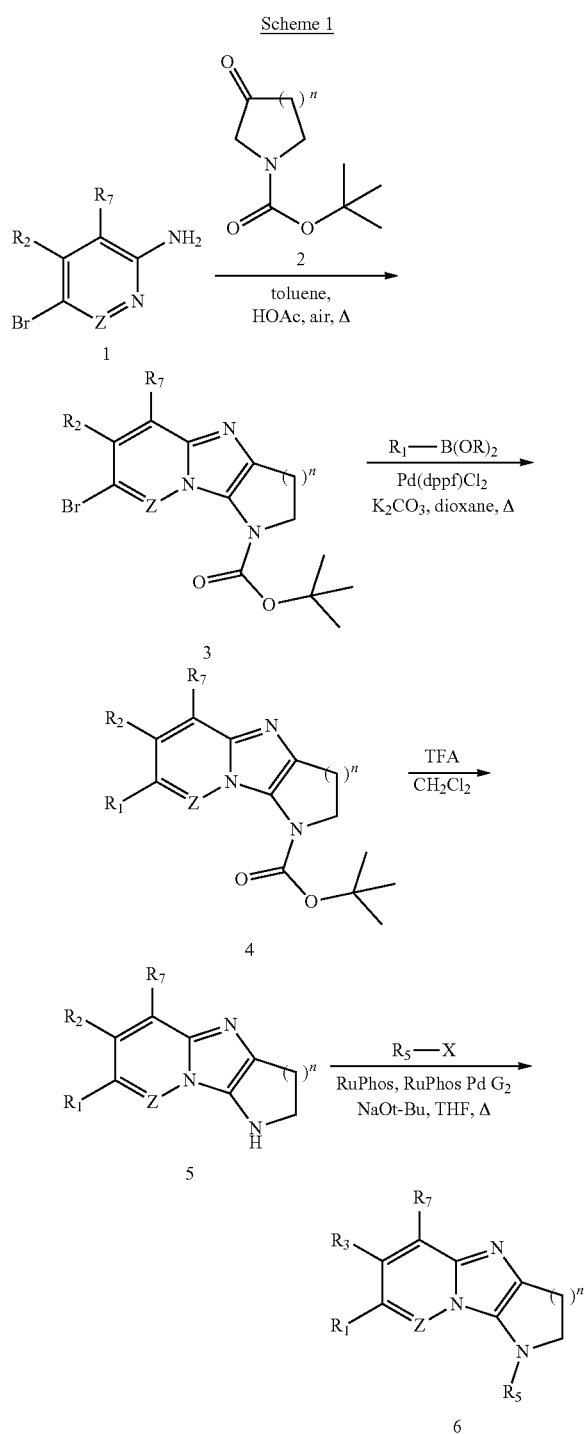

Alternatively, as depicted in Scheme 2, intermediates of structure 5 can also be prepared from compounds 3 by a reaction sequence wherein the order of the acid-promoted N-deprotection and Suzuki coupling steps are switched. This alternative route is particularly useful when $R_1$ contains an acid labile functional group.

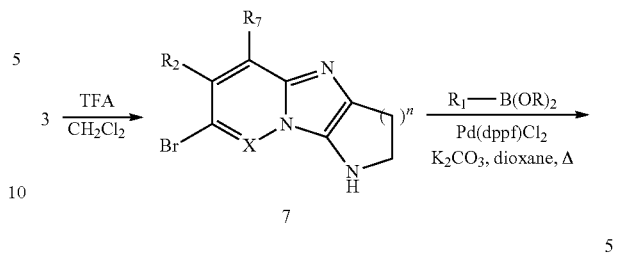

Abbreviations

DCM dichloromethane
DMSO dimethyl sulfoxide
EtOAc ethyl acetate
h hour(s)
HPLC High Pressure Liquid Chromatography
LC/MS Liquid Chromatography-Mass Spectroscopy
MeOH methanol
min minute(s)
mmol millimole(s)
NMR nuclear magnetic resonance spectroscopy
$PdCl_2(dppf)$ [1,1'-bis(diphenylphosphino)ferrocene]dichloropalladium(II)
TFA trifluoroacetic acid
THF tetrahydrofuran

EXAMPLES

The following Examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well-known bioisosteric replacements known in the art, for example, replacement of a carboxylic acid group with a tetrazole or a phosphate moiety.

Example 1

1-(2,5-Dimethylphenyl)-8-(6-methoxypyridin-3-yl)-7-methyl-1,2,3,4-tetrahydroimidazo [1,2-a:5,4-b'] dipyridine

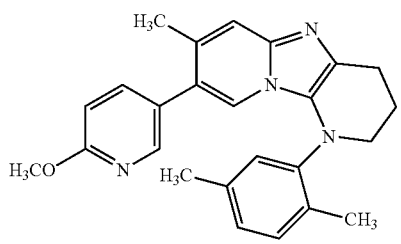

Intermediate 1A: tert-Butyl 8-bromo-7-methyl-3,4-dihydroimidazo[1,2-a:5,4-b']dipyridine-1(2H)-carboxylate

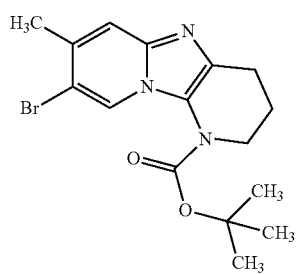

A mixture of 5-bromo-4-methylpyridin-2-amine (5.0 g, 26.7 mmol), tert-butyl 3-oxopiperidine-1-carboxylate (5.33 g, 26.7 mmol), and acetic acid (0.153 mL, 2.67 mmol) in toluene (100 mL) was heated to reflux. Water was azeotroped using a Dean-Stark apparatus. The mixture was heated at reflux for 24 h. After cooling to room temperature, air was bubbled through the reaction mixture for 2 h to promote oxidative dehydrogenation. The resulting dark solution was concentrated under high vacuum to afford a black oil. The oil was diluted with ethyl acetate and washed with saturated aqueous sodium bicarbonate solution. The aqueous portion was back extracted with ethyl acetate. The combined organic portions were washed with brine, dried over magnesium sulfate, filtered and concentrated in vacuo. The crude product was purified twice using silica gel column chromatography (100% EtOAc) to afford tert-butyl 8-bromo-7-methyl-3,4-dihydroimidazo[1,2-a:5,4-b']dipyridine-1(2H)-carboxylate (1.18 g, 3.06 mmol, 12% yield). LC/MS (M+H) 366.1, 368.1; $^1$H NMR (500 MHz, chloroform-d) δ 8.13 (s, 1H), 7.35 (s, 1H), 3.76 (br. s., 2H), 2.93 (t, J=6.8 Hz, 2H), 2.46 (s, 3H), 2.14-2.05 (m, 2H), 1.53 (s, 9H).

Intermediate 1B: tert-Butyl 8-(6-methoxypyridin-3-yl)-7-methyl-3,4-dihydroimidazo [1,2-a:5,4-b'] dipyridine-1(2H)-carboxylate

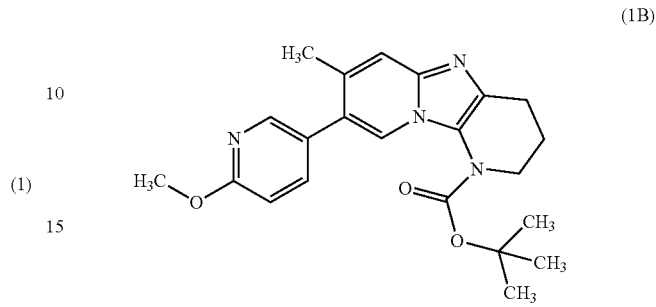

A mixture of tert-butyl 8-bromo-7-methyl-3,4-dihydroimidazo[1,2-a:5,4-b']dipyridine-1(2H)-carboxylate (200 mg, 0.546 mmol), (6-methoxypyridin-3-yl)boronic acid (84 mg, 0.546 mmol), 2 M solution of aqueous potassium carbonate (426 μl, 0.852 mmol), and dioxane (4 mL) was purged with bubbled nitrogen for 10 min. PdCl$_2$(dppf)-CH$_2$Cl$_2$ adduct (44.6 mg, 0.055 mmol) was added, the vial was purged with nitrogen, sealed with a Teflon cap and heated at 90° C. for 16 h. The reaction mixture was cooled to room temperature and added to a saturated solution of aqueous sodium bicarbonate. The mixture was extracted with ethyl acetate. The combined organic layers were washed with brine, dried over sodium sulfate, filtered, and concentrated in vacuo. The crude product was purified using silica gel column chromatography (100% ethyl acetate) to afford tert-butyl 8-(6-methoxypyridin-3-yl)-7-methyl-3,4-dihydroimidazo[1,2-a:5,4-b']dipyridine-1(2H)-carboxylate (189 mg, 0.455 mmol, 83% yield). LC/MS (M+H) 395.20; $^1$H NMR (500 MHz, chloroform-d) δ 8.17 (d, J=2.1 Hz, 1H), 7.77 (s, 1H), 7.58 (dd, J=8.5, 2.1 Hz, 1H), 7.37 (s, 1H), 6.85 (d, J=8.4 Hz, 1H), 4.02 (s, 3H), 3.76 (br. s., 2H), 2.96 (t, J=6.7 Hz, 2H), 2.26 (s, 3H), 2.15-2.08 (m, 2H), 1.45 (br. s., 9H).

Intermediate 1C: 8-(6-Methoxypyridin-3-yl)-7-methyl-1,2,3,4-tetrahydroimidazo [1,2-a:5,4-b'] dipyridine, TFA

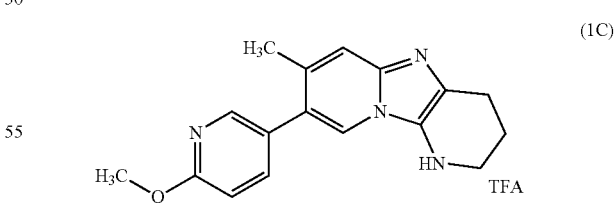

Trifluoroacetic acid (2 mL) was added to a solution of tert-butyl 8-(6-methoxypyridin-3-yl)-7-methyl-3,4-dihydroimidazo[1,2-a:5,4-b']dipyridine-1(2H)-carboxylate (187 mg, 0.474 mmol) in DCM (10 mL). The mixture was allowed to stir at room temperature for 2 h. The reaction mixture was concentrated in vacuo. Residual solvents were removed under high vacuum to afford 8-(6-methoxypyridin-3-yl)-7-methyl-1,2,3,4-tetrahydroimidazo[1,2-a:5,4-b']

dipyridine, TFA (114 mg, quantitative yield). Material was used as is without any purification. LC/MS (M+H) 295.2.

Example 1

A mixture of RuPhos (2-dicyclohexylphosphino-2',6'-diisopropoxybiphenyl) (0.014 g, 0.031 mmol), RuPhos Pd G2 (chloro(2-dicyclohexylphosphino-2',6'-diisopropoxy-1,1'-biphenyl)[2-(2'-amino-1,1'-biphenyl)]palladium(II)) (0.012 g, 0.015 mmol), and sodium tert-butoxide (0.018 g, 0.183 mmol) was capped in a high pressure vial and purged with nitrogen. To this vial was added a solution of 2-bromo-1,4-dimethylbenzene (0.023 g, 0.122 mmol) and 8-(6-methoxypyridin-3-yl)-7-methyl-1,2,3,4-tetrahydroimidazo[1,2-a:5,4-b']dipyridine, TFA (18.0 mg, 0.061 mmol) dissolved in THF (4 mL). The vial was heated at 85° C. for 16 h. The vial was allowed to cool to room temperature and then uncapped. The reaction mixture was diluted with ethyl acetate and washed with saturated aqueous sodium bicarbonate solution. The aqueous layer was back extracted with ethyl acetate. The combined organic layers were washed with brine, dried over magnesium sulfate, filtered, and concentrated in vacuo. The crude product was passed through a short plug of silica gel (1 g), eluting with ethyl acetate to remove non-polar impurities. Then the material was eluted with 5% MeOH/ethyl acetate to obtain the desired product with unreacted starting material. The latter fraction was concentrated, and the residue was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-90% B over 15 minutes, then a 6-minute hold at 100% B; Flow: 20 mL/min. Fractions containing the desired product were combined and dried via centrifugal evaporation to afford 1-(2,5-dimethylphenyl)-8-(6-methoxypyridin-3-yl)-7-methyl-1,2,3,4-tetrahydroimidazo[1,2-a:5,4-b']dipyridine (1.9 mg, 9% yield). LC/MS (M+H) 399.0; $^1$H NMR (500 MHz, DMSO-$d_6$) δ 7.86 (s, 1H), 7.61 (d, J=8.1 Hz, 1H), 7.39 (s, 1H), 7.16 (d, J=7.7 Hz, 1H), 6.82 (d, J=8.8 Hz, 1H), 6.85 (d, J=7.7 Hz, 1H), 6.69 (s, 1H), 6.23 (s, 1H), 3.84 (s, 3H), 3.58-3.37 (m, 2H), 2.88-2.76 (m, 2H), 2.34 (br. s., 3H), 2.17 (s, 3H), 2.07 (s, 3H), 1.93-1.80 (m, 2H).

Example 2

1-(2-(Difluoromethoxy)phenyl)-8-(6-methoxypyridin-3-yl)-7-methyl-1,2,3,4-tetrahydroimidazo[1,2-a:5,4-b']dipyridine

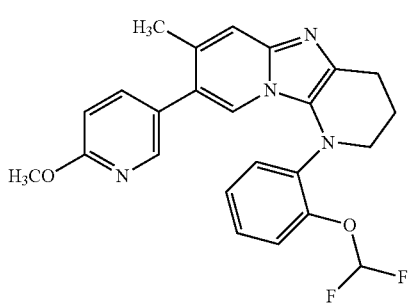

(2)

Following the N-arylation procedure and purification method used in the final step for the preparation of Example 1, 8-(6-methoxypyridin-3-yl)-7-methyl-1,2,3,4-tetrahydroimidazo[1,2-a:5,4-b']dipyridine, TFA (Intermediate 1C, 18.0 mg, 0.061 mmol) was reacted with 1-bromo-2-(difluoromethoxy)benzene (0.027 g, 0.122 mmol) to afford 1-(2-(difluoromethoxy)phenyl)-8-(6-methoxypyridin-3-yl)-7-methyl-1,2,3,4-tetrahydroimidazo[1,2-a:5,4-b']dipyridine (2.0 mg, 7% yield). LC/MS (M+H) 437.0; $^1$H NMR (500 MHz, DMSO-$d_6$) δ 7.92 (br. s., 1H), 7.65 (d, J=8.4 Hz, 1H), 7.43 (s, 1H), 7.27 (d, J=7.7 Hz, 1H), 7.30 (t, J=74.3 Hz, 1H), 7.15-7.07 (m, 2H), 6.93 (s, 1H), 6.83 (d, J=8.8 Hz, 1H), 6.32 (d, J=7.7 Hz, 1H), 3.84 (s, 3H), 3.75-3.54 (m, 2H), 2.87-2.78 (m, 2H), 2.19 (s, 3H), 1.87-1.74 (m, 2H).

Example 3

1-(2,5-Dimethylphenyl)-7-methyl-8-(1-methyl-1H-pyrazol-4-yl)-1,2,3,4-tetrahydroimidazo[1,2-a:5,4-b']dipyridine

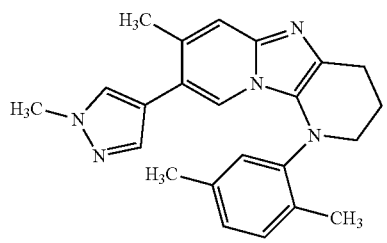

(3)

Intermediate 3A: tert-Butyl 7-methyl-8-(1-methyl-1H-pyrazol-4-yl)-3,4-dihydroimidazo[1,2-a:5,4-b']dipyridine-1(2H)-carboxylate

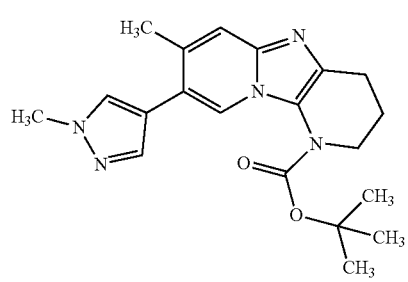

(3A)

Following the metal-mediated coupling procedure and purification method used in the preparation of Intermediate 1B, tert-butyl 8-bromo-7-methyl-3,4-dihydroimidazo[1,2-a:5,4-b']dipyridine-1(2H)-carboxylate (Intermediate 1A, 200 mg, 0.546 mmol) was reacted with (1-methyl-1H-pyrazol-4-yl)boronic acid (68.8 mg, 0.546 mmol) to afford tert-butyl 7-methyl-8-(1-methyl-1H-pyrazol-4-yl)-3,4-dihydroimidazo[1,2-a:5,4-b']dipyridine-1(2H)-carboxylate (62.5 mg, 30% yield). LC/MS (M+H) 368.2; $^1$H NMR (400 MHz, chloroform-d) δ 7.82 (s, 1H), 7.59 (d, J=0.8 Hz, 1H), 7.46 (s, 1H), 7.32 (s, 1H), 4.00 (s, 3H), 3.75 (br. s., 2H), 2.94 (t, J=6.8 Hz, 2H), 2.37 (d, J=0.8 Hz, 3H), 2.13-2.05 (m, 2H), 1.46 (br. s., 9H).

Intermediate 3B: 1-(2,5-Dimethylphenyl)-7-methyl-8-(1-methyl-1H-pyrazol-4-yl)-1,2,3,4-tetrahydroimidazo[1,2-a:5,4-b']dipyridine, TFA

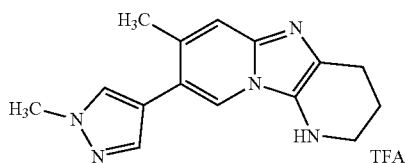

(3B)

Trifluoroacetic acid (1 mL) was added to a solution of tert-butyl 7-methyl-8-(1-methyl-1H-pyrazol-4-yl)-3,4-dihydroimidazo[1,2-a:5,4-b']dipyridine-1(2H)-carboxylate (62 mg, 0.169 mmol) in DCM (5 mL). The mixture was allowed to stir at room temperature for 2 h. The reaction mixture was concentrated in vacuo. Residual solvents were removed under high vacuum to afford 1-(2,5-dimethylphenyl)-7-methyl-8-(1-methyl-1H-pyrazol-4-yl)-1,2,3,4-tetrahydroimidazo[1,2-a:5,4-b']dipyridine, TFA (64 mg, quantitative yield). Material was used as is without any purification. LC/MS (M+H) 268.2.

Example 3

Following the N-arylation procedure and purification method used in the final step for the preparation of Example 1, 1-(2,5-dimethylphenyl)-7-methyl-8-(1-methyl-1H-pyrazol-4-yl)-1,2,3,4-tetrahydroimidazo[1,2-a:5,4-b']dipyridine, TFA (28 mg, 0.073 mmol) was reacted with 2-bromo-1,4-dimethylbenzene (0.027 g, 0.147 mmol) to afford 1-(2,5-dimethylphenyl)-7-methyl-8-(1-methyl-1H-pyrazol-4-yl)-1,2,3,4-tetrahydroimidazo[1,2-a:5,4-b']dipyridine (2.2 mg, 9% yield). LC/MS (M+H) 372.0; $^1$H NMR (500 MHz, DMSO-d$_6$) δ 7.73 (s, 1H), 7.33 (s, 1H), 7.25 (s, 1H), 7.20 (d, J=7.3 Hz, 1H), 6.86 (d, J=7.3 Hz, 1H), 6.75 (s, 1H), 6.23 (s, 1H), 3.53-3.46 (m, 2H), 2.88-2.74 (m, 2H), 2.40 (s, 3H), 2.28 (s, 3H), 2.06 (s, 3H), 1.82 (s, 3H), 1.97-1.77 (m, 2H).

Example 4

1-(2-(Difluoromethoxy)phenyl)-7-methyl-8-(1-methyl-1H-pyrazol-4-yl)-1,2,3,4-tetrahydroimidazo[1,2-a:5,4-b']dipyridine

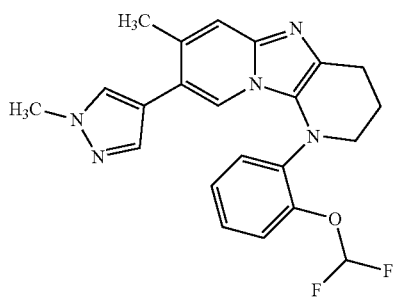

(4)

Following the N-arylation procedure and purification method used in the final step for the preparation of Example 1, 1-(2,5-dimethylphenyl)-7-methyl-8-(1-methyl-1H-pyrazol-4-yl)-1,2,3,4-tetrahydroimidazo[1,2-a:5,4-b']dipyridine, TFA (Intermediate 3B, 25 mg, 0.066 mmol) was reacted with 1-bromo-2-(difluoromethoxy)benzene (0.029 g, 0.131 mmol) to afford 1-(2-(difluoromethoxy)phenyl)-7-methyl-8-(1-methyl-1H-pyrazol-4-yl)-1,2,3,4-tetrahydroimidazo[1,2-a:5,4-b']dipyridine (1.8 mg, 7% yield). LC/MS (M+H) 410.0; $^1$H NMR (500 MHz, DMSO-d$_6$) δ 7.77 (s, 1H), 7.40 (s, 1H), 7.33 (s, 1H), 7.31 (d, J=8.1 Hz, 1H), 7.35 (t, J=74.5 Hz, 1H), 7.18-7.05 (m, 2H), 6.94 (s, 1H), 6.31 (d, J=7.7 Hz, 1H), 3.82 (s, 3H), 3.74-3.56 (m, 2H), 2.83 (t, J=6.2 Hz, 2H), 2.31 (s, 3H), 1.87-1.79 (m, 2H).

Example 5

1-(2,5-Dimethylphenyl)-8-(6-methoxypyridin-3-yl)-1,2,3,4-tetrahydroimidazo [1,2-a:5,4-b']dipyridine

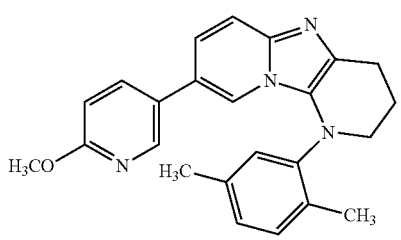

(5)

Intermediate 5A: tert-Butyl 8-bromo-3,4-dihydroimidazo[1,2-a:5,4-b']dipyridine-1(2H)-carboxylate

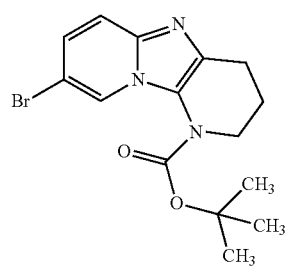

(5A)

A mixture of 5-bromopyridin-2-amine (7.80 g, 45.1 mmol), tert-butyl 3-oxopiperidine-1-carboxylate (8.98 g, 45.1 mmol), and acetic acid (0.258 mL, 4.51 mmol) in toluene (100 mL) was heated to reflux. Water was azeotroped using a Dean-Stark apparatus. The mixture was heated at reflux for 3 days. After cooling to room temperature, air was bubbled through the reaction mixture for 2 h to promote oxidative dehydrogenation. The resulting black solution was concentrated under high vacuum to afford a black oil. The black oil was diluted with ethyl acetate and washed with saturated aqueous sodium bicarbonate solution. The aqueous portion was back extracted with ethyl acetate. The combined organic portions were washed with brine, dried over magnesium sulfate, filtered and concentrated in vacuo. The crude product was purified twice using silica gel column chromatography (100% EtOAc) to afford tert-butyl 8-bromo-3,4-dihydroimidazo[1,2-a:5,4-b']dipyridine-1(2H)-carboxylate (2.74 g, 7.78 mmol, 17% yield). LC/MS (M+H) 352.1, 354.1; ¹H NMR (500 MHz, chloroform-d) δ 8.07 (dd, J=2.0, 0.8 Hz, 1H), 7.42-7.37 (m, 1H), 7.18 (dd, J=9.5, 2.0 Hz, 1H), 3.75 (br. s., 2H), 2.94 (t, J=6.7 Hz, 2H), 2.12-2.05 (m, 2H), 1.51 (s, 9H).

Intermediate 5B: tert-Butyl 8-(6-methoxypyridin-3-yl)-3,4-dihydroimidazo[1,2-a:5,4-b']dipyridine-1(2H)-carboxylate

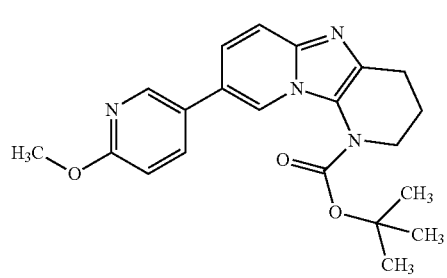

(5B)

Following the metal-mediated coupling procedure and purification method used in the preparation of Intermediate 1B, tert-butyl 8-bromo-3,4-dihydroimidazo[1,2-a:5,4-b']dipyridine-1(2H)-carboxylate (100 mg, 0.284 mmol) was reacted with (6-methoxypyridin-3-yl)boronic acid (43.4 mg, 0.284 mmol) to afford tert-butyl 8-(6-methoxypyridin-3-yl)-3,4-dihydroimidazo[1,2-a:5,4-b']dipyridine-1(2H)-carboxylate (89 mg, 0.222 mmol, 78% yield). LC/MS (M+H) 381.2; ¹H NMR (500 MHz, chloroform-d) δ 8.40 (d, J=2.4 Hz, 1H), 8.05 (s, 1H), 7.78 (dd, J=8.5, 2.6 Hz, 1H), 7.57 (d, J=9.3 Hz, 1H), 7.31 (dd, J=9.3, 1.8 Hz, 1H), 6.86 (d, J=8.5 Hz, 1H), 4.00 (s, 3H), 3.79 (br. s., 2H), 2.98 (t, J=6.8 Hz, 2H), 2.12 (dq, J=6.6, 5.8 Hz, 2H), 1.48 (br. s., 9H).

Intermediate 5C: 8-(6-Methoxypyridin-3-yl)-1,2,3,4-tetrahydroimidazo[1,2-a:5,4-b']dipyridine, TFA

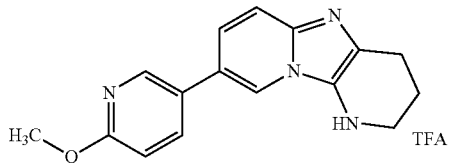

(5C)

Trifluoroacetic acid (1 mL) was added to a solution of tert-butyl 8-(6-methoxypyridin-3-yl)-3,4-dihydroimidazo[1,2-a:5,4-b']dipyridine-1(2H)-carboxylate (450 mg, 1.183 mmol) in DCM (5 mL). The mixture was allowed to stir at room temperature for 2 h. The reaction mixture was concentrated in vacuo. Residual solvents were removed under high vacuum. The residue was crystallized from THF (10 mL) to afford 8-(6-methoxypyridin-3-yl)-1,2,3,4-tetrahydroimidazo[1,2-a:5,4-b']dipyridine, TFA (205 mg, 0.509 mmol, 43.1% yield) as a light yellow crystalline solid. LC/MS (M+H) 281.2; ¹H NMR (500 MHz, methanol-d₄) δ 8.59-8.45 (m, 2H), 8.04 (dd, J=12.7, 9.1 Hz, 1H), 8.05 (dd, J=13.8, 9.1 Hz, 1H), 7.85 (dd, J=9.3, 0.9 Hz, 1H), 6.99 (dd, J=8.7, 0.6 Hz, 1H), 4.00 (s, 3H), 3.52-3.44 (m, 2H), 2.96 (t, J=6.3 Hz, 2H), 2.10 (dt, J=11.3, 6.0 Hz, 2H).

Example 5

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (30 mg, 0.076 mmol) was reacted with 2-bromo-1,4-dimethylbenzene (28.2 mg, 0.152 mmol) to afford 1-(2,5-dimethylphenyl)-8-(6-methoxypyridin-3-yl)-1,2,3,4-tetrahydroimidazo[1,2-a:5,4-b']dipyridine (21.4 mg, 0.055 mmol, 72% yield). LC/MS (M+H) 385.2; ¹H NMR (500 MHz, DMSO-d₆) δ 8.07 (s, 1H), 7.70 (d, J=8.4 Hz, 1H), 7.57 (d, J=9.2 Hz, 1H), 7.36 (d, J=9.2 Hz, 1H), 7.25 (d, J=7.3 Hz, 1H), 7.01 (s, 1H), 6.90 (d, J=7.0 Hz, 1H), 6.86 (d, J=8.4 Hz, 1H), 6.27 (s, 1H), 3.84 (s, 3H), 3.63-3.41 (m, 2H), 3.00-2.80 (m, 2H), 2.44 (s, 3H), 2.05 (s, 3H), 2.00-1.78 (m, 2H).

Example 6

1-(2-(Difluoromethoxy)phenyl)-8-(6-methoxypyridin-3-yl)-1,2,3,4-tetrahydroimidazo[1,2-a:5,4-b']dipyridine

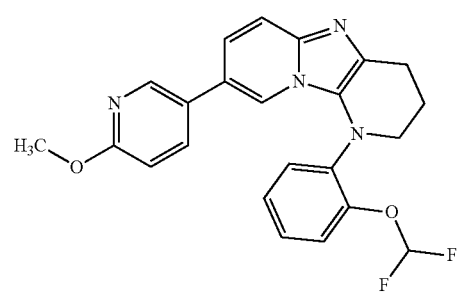

(6)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 55 mg, 0.108 mmol) was reacted with 1-bromo-2-(difluoromethoxy)benzene (48.3 mg, 0.216 mmol) to afford 1-(2-(difluoromethoxy)phenyl)-8-(6-methoxypyridin-3-yl)-1,2,3,4-tetrahydroimidazo [1,2-a:5,4-b']dipyridine (6.5 mg, 0.015 mmol, 14% yield). LC/MS (M+H) 423.1; ¹H NMR (500 MHz, DMSO-d₆) δ 8.19-8.13 (m, 1H), 7.76 (d, J=8.4 Hz, 1H), 7.61 (d, J=9.2 Hz, 1H), 7.42 (d, J=9.5 Hz, 1H), 7.35 (d, J=7.7 Hz, 1H), 7.39 (t, J=74.0 Hz, 1H), 7.24 (s, 1H), 7.18 (t, J=7.7 Hz, 1H), 7.11 (t, J=7.7 Hz, 1H), 6.87 (d, J=8.8 Hz, 1H), 6.35 (d, J=7.7 Hz, 1H), 3.85 (s, 3H), 3.77-3.64 (m, 2H), 2.89-2.84 (m, 2H), 1.89-1.81 (m, 2H).

Example 7

1-(2-Methoxy-5-methylphenyl)-8-(6-methoxypyridin-3-yl)-1,2,3,4-tetrahydroimidazo [1,2-a:5,4-b'] dipyridine

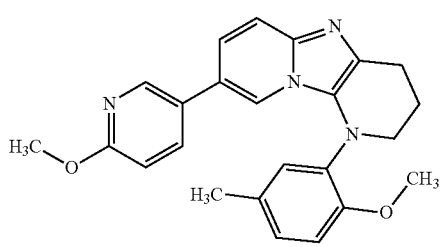

(7)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 35 mg, 0.089 mmol) was reacted with 2-bromo-1-methoxy-4-methylbenzene (89 mg, 0.444 mmol) to afford 1-(2-methoxy-5-methylphenyl)-8-(6-methoxypyridin-3-yl)-1,2,3,4-tetrahydroimidazo[1,2-a:5,4-b']dipyridine (9.1 mg, 0.022 mmol, 25% yield). LC/MS (M+H) 401.1; $^1$H NMR (500 MHz, DMSO-$d_6$) δ 8.12 (s, 1H), 7.74 (d, J=8.4 Hz, 1H), 7.58 (d, J=9.2 Hz, 1H), 7.38 (d, J=9.2 Hz, 1H), 7.10 (s, 1H), 7.04 (d, J=8.4 Hz, 1H), 6.95-6.83 (m, 2H), 6.06 (s, 1H), 3.85 (s, 3H), 3.87 (s, 3H), 3.71-3.54 (m, 2H), 2.86 (br. s., 2H), 2.03 (s, 3H), 1.89-1.76 (m, 2H).

Example 8

1-(Isoquinolin-1-yl)-8-(6-methoxypyridin-3-yl)-1,2,3,4-tetrahydroimidazo [1,2-a:5,4-b']dipyridine

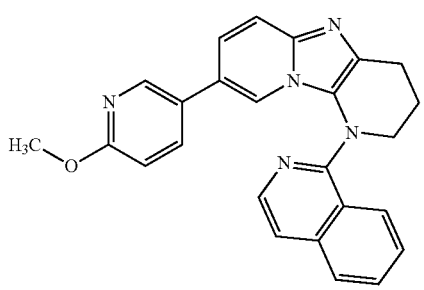

(8)

Following the N-arylation procedure and purification method used in the final step for the preparation of Example 1, 8-(6-methoxypyridin-3-yl)-1,2,3,4-tetrahydroimidazo [1,2-a:5,4-b']dipyridine, TFA (Intermediate 5C, 25 mg, 0.063 mmol) was reacted with 1-bromo-2-methylnaphthalene (28.0 mg, 0.127 mmol) to afford 1-(isoquinolin-1-yl)-8-(6-methoxypyridin-3-yl)-1,2,3,4-tetrahydroimidazo[1,2-a:5,4-b']dipyridine (20.4 mg, 0.050 mmol, 79% yield). LC/MS (M+H) 408.0; $^1$H NMR (500 MHz, DMSO-$d_6$) δ 8.38 (d, J=8.4 Hz, 1H), 8.06 (s, 1H), 8.01 (d, J=5.5 Hz, 2H), 7.83 (t, J=7.5 Hz, 1H), 7.75 (t, J=7.7 Hz, 1H), 7.68 (d, J=8.4 Hz, 1H), 7.61 (d, J=9.2 Hz, 1H), 7.54 (d, J=5.5 Hz, 1H), 7.39 (d, J=9.2 Hz, 1H), 7.06 (s, 1H), 6.79 (d, J=8.4 Hz, 1H), 4.22-4.00 (m, 2H), 3.79 (s, 3H), 2.99-2.86 (m, 2H), 1.98-1.84 (m, 2H).

Example 9

8-(6-Methoxypyridin-3-yl)-1-(o-tolyl)-1,2,3,4-tetrahydroimidazo[1,2-a:5,4-b']dipyridine

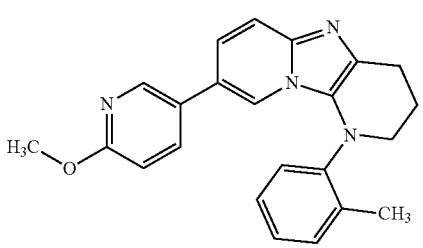

(9)

Following the N-arylation procedure and purification method used in the final step for the preparation of Example 1, 8-(6-methoxypyridin-3-yl)-1,2,3,4-tetrahydroimidazo [1,2-a:5,4-b']dipyridine, TFA (Intermediate 5C, 25 mg, 0.063 mmol) was reacted with 1-bromo-2-methylbenzene (21.69 mg, 0.127 mmol) to afford 8-(6-methoxypyridin-3-yl)-1-(o-tolyl)-1,2,3,4-tetrahydroimidazo[1,2-a:5,4-b'] dipyridine (13 mg, 0.035 mmol, 55% yield). LC/MS (M+H) 371.2; $^1$H NMR (500 MHz, DMSO-$d_6$) δ 8.06 (s, 1H), 7.68 (d, J=8.4 Hz, 1H), 7.56 (d, J=9.2 Hz, 1H), 7.34 (d, J=9.2 Hz, 1H), 7.37 (d, J=7.3 Hz, 1H), 7.15-7.00 (m, 2H), 6.99 (s, 1H), 6.84 (d, J=8.8 Hz, 1H), 6.40 (d, J=7.3 Hz, 1H), 3.83 (s, 3H), 3.61-3.44 (m, 2H), 2.97-2.80 (m, 2H), 2.50 (s, 3H), 1.98-1.78 (m, 2H).

Example 10

8-(6-Methoxypyridin-3-yl)-1-(2-(trifluoromethoxy)phenyl)-1,2,3,4-tetrahydroimidazo[1,2-a:5,4-b']dipyridine

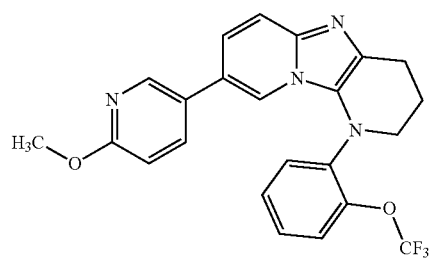

(10)

Following the N-arylation procedure and purification method used in the final step for the preparation of Example 1, 8-(6-methoxypyridin-3-yl)-1,2,3,4-tetrahydroimidazo [1,2-a:5,4-b']dipyridine, TFA (Intermediate 5C, 25 mg, 0.063 mmol) was reacted with 1-bromo-2-(trifluoromethoxy)benzene (30.6 mg, 0.127 mmol) to afford 8-(6-methoxypyridin-3-yl)-1-(2-(trifluoromethoxy)phenyl)-1,2, 3,4-tetrahydroimidazo [1,2-a:5,4-b']dipyridine (8.4 mg, 0.019 mmol, 30% yield). LC/MS (M+H) 441.2; $^1$H NMR (500 MHz, DMSO-$d_6$) δ 8.08 (s, 1H), 7.68 (d, J=8.4 Hz, 1H), 7.63 (d, J=9.5 Hz, 1H), 7.53 (br. s., 1H), 7.43 (d, J=9.2 Hz, 1H), 7.29-7.21 (m, 2H), 7.05 (s, 1H), 6.88 (d, J=8.8 Hz, 1H), 6.57-6.49 (m, 1H), 3.84 (s, 3H), 3.69 (br. s., 2H), 2.93-2.81 (m, 2H), 1.94-1.83 (m, 2H).

Example 11

8-(6-Methoxypyridin-3-yl)-1-(2-methyl-5-(trifluoromethyl)phenyl)-1,2,3,4-tetrahydroimidazo[1,2-a:5,4-b']dipyridine

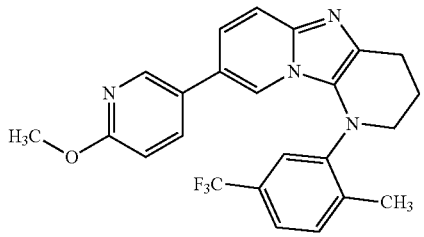

(11)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 2-bromo-1-fluoro-4-(trifluoromethyl)benzene (30.8 mg, 0.127 mmol) to afford 8-(6-methoxypyridin-3-yl)-1-(2-methyl-5-(trifluoromethyl)phenyl)-1,2,3,4-tetrahydroimidazo [1,2-a:5,4-b']dipyridine (15.3 mg, 0.035 mmol, 55% yield). LC/MS (M+H) 439.2; $^1$H NMR (500 MHz, DMSO-$d_6$) δ 8.06 (s, 1H), 7.70 (d, J=8.8 Hz, 1H), 7.66-7.58 (m, 2H), 7.47 (d, J=7.7 Hz, 1H), 7.40 (d, J=9.2 Hz, 1H), 7.02 (s, 1H), 6.86 (d, J=8.8 Hz, 1H), 6.53 (s, 1H), 3.84 (s, 3H), 3.66-3.57 (m, 2H), 3.01-2.84 (m, 2H), 2.58 (s, 3H), 1.97-1.86 (m, 2H).

Example 12

1-(2,5-Dimethylphenyl)-8-(1-methyl-1H-pyrazol-4-yl)-1,2,3,4-tetrahydroimidazo [1,2-a:5,4-b']dipyridine

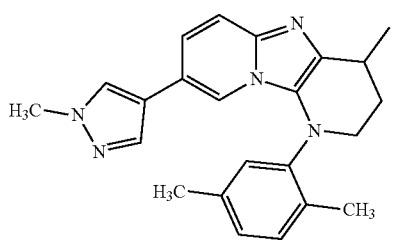

(12)

Intermediate 12A: tert-Butyl 8-(1-methyl-1H-pyrazol-4-yl)-3,4-dihydroimidazo [1,2-a:5,4-b']dipyridine-1(2H)-carboxylate

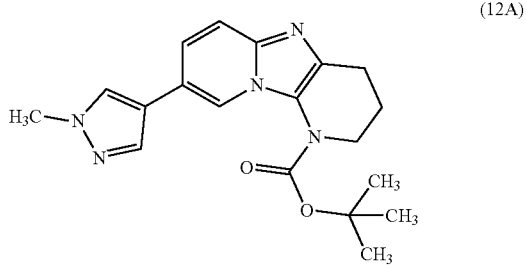 [SMILES: Cn1cc(-c2ccc3nc4c(n3c2)N(C(=O)OC(C)(C)C)CCC4)cn1]

(12A)

Following the metal-mediated coupling procedure and purification method used in the preparation of Intermediate 1B, tert-butyl 8-bromo-3,4-dihydroimidazo[1,2-a:5,4-b']dipyridine-1(2H)-carboxylate (Intermediate 5A, 133 mg, 0.378 mmol) was reacted with (1-methyl-1H-pyrazol-4-yl)boronic acid (47.5 mg, 0.378 mmol) to afford tert-butyl 8-(1-methyl-1H-pyrazol-4-yl)-3,4-dihydroimidazo[1,2-a:5,4-b']dipyridine-1(2H)-carboxylate (98 mg, 0.277 mmol, 73% yield). LC/MS (M+H) 354.3; $^1$H NMR (400 MHz, chloroform-d) δ 8.02 (dd, J=1.8, 1.0 Hz, 1H), 7.73 (s, 1H), 7.60 (s, 1H), 7.50 (dd, J=9.2, 0.8 Hz, 1H), 7.25 (dd, J=9.2, 1.8 Hz, 1H), 3.98 (s, 3H), 3.78 (br. s., 2H), 2.96 (t, J=6.8 Hz, 2H), 2.15-2.07 (m, 2H), 1.49 (br. s., 9H).

Intermediate 12B: 8-(1-Methyl-1H-pyrazol-4-yl)-1,2,3,4-tetrahydroimidazo[1,2-a:5,4-b']dipyridine, 2 TFA

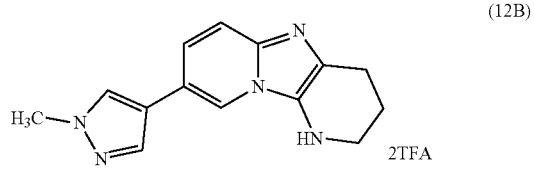 [SMILES: Cn1cc(-c2ccc3nc4c(n3c2)NCCC4)cn1]

(12B)

Trifluoroacetic acid (1 mL) was added to a solution of tert-butyl 8-(1-methyl-1H-pyrazol-4-yl)-3,4-dihydroimidazo[1,2-a:5,4-b']dipyridine-1(2H)-carboxylate (93 mg, 0.263 mmol) in DCM (5 mL). The mixture was allowed to stir at room temperature for 2 h. The reaction mixture was concentrated in vacuo. Residual solvents were removed under high vacuum to afford 8-(1-methyl-1H-pyrazol-4-yl)-1,2,3,4-tetrahydroimidazo [1,2-a:5,4-b']dipyridine, 2 TFA (132 mg, 0.274 mmol, quantitative yield). Material was used as is without any purification. LC/MS (M+H) 254.2.

Example 12

Following the N-arylation procedure and purification method used in the final step for the preparation of Example 1, 8-(1-methyl-1H-pyrazol-4-yl)-1,2,3,4-tetrahydroimidazo [1,2-a:5,4-b']dipyridine, 2 TFA (65 mg, 0.135 mmol) was reacted with 2-bromo-1,4-dimethylbenzene (50.0 mg, 0.270 mmol) to afford 1-(2,5-dimethylphenyl)-8-(1-methyl-1H-pyrazol-4-yl)-1,2,3,4-tetrahydroimidazo[1,2-a:5,4-b']dipyridine (19.8 mg, 0.055 mmol, 41% yield). LC/MS (M+H)

358.2; $^1$H NMR (500 MHz, DMSO-$d_6$) δ 7.86 (s, 1H), 7.48 (d, J=9.5 Hz, 1H), 7.44 (s, 1H), 7.26 (d, J=8.1 Hz, 2H), 6.99 (s, 1H), 6.90 (d, J=8.1 Hz, 1H), 6.26 (s, 1H), 3.81 (s, 3H), 3.61-3.39 (m, 2H), 2.98-2.75 (m, 2H), 2.46 (s, 3H), 2.05 (s, 3H), 2.00-1.77 (m, 2H).

Example 13

1-(2-(Difluoromethoxy)phenyl)-8-(1-methyl-1H-pyrazol-4-yl)-1,2,3,4-tetrahydroimidazo[1,2-a:5,4-b'] dipyridine

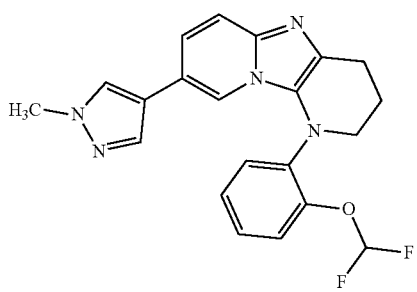

(13)

Following the N-arylation procedure and purification method used in the final step for the preparation of Example 1, 8-(1-methyl-1H-pyrazol-4-yl)-1,2,3,4-tetrahydroimidazo[1,2-a:5,4-b']dipyridine, 2 TFA (Intermediate 12B, 65 mg, 0.135 mmol) was reacted with 1-bromo-2-(difluoromethoxy)benzene (60.2 mg, 0.270 mmol) to afford 1-(2-(difluoromethoxy)phenyl)-8-(1-methyl-1H-pyrazol-4-yl)-1,2,3,4-tetrahydroimidazo[1,2-a:5,4-b']dipyridine (12.2 mg, 0.031 mmol, 10% yield). LC/MS (M+H) 396.1; $^1$H NMR (500 MHz, DMSO-$d_6$) δ 7.90 (s, 1H), 7.55-7.49 (m, 2H), 7.38 (t, J=74.0 Hz, 1H), 7.33 (t, J=9.7 Hz, 2H), 7.20-7.13 (m, 2H), 7.12-7.04 (m, 1H), 6.32 (d, J=8.1 Hz, 1H), 3.80 (s, 3H), 3.74-3.60 (m, 2H), 2.84 (t, J=6.2 Hz, 2H), 1.88-1.79 (m, 2H).

Example 14

4-(5-(1-(2,5-Dimethylphenyl)-1,2,3,4-tetrahydroimidazo[1,2-a:5,4-b']dipyridin-8-yl)pyrimidin-2-yl)morpholine

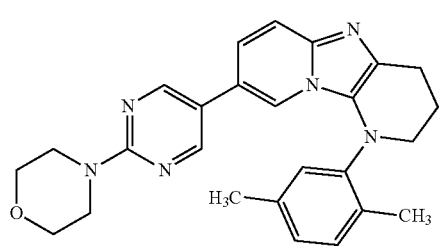

(14)

Intermediate 14A: tert-Butyl 8-(2-morpholinopyrimidin-5-yl)-3,4-dihydroimidazo [1,2-a:5,4-b'] dipyridine-1(2H)-carboxylate (14A)

Following the metal-mediated coupling procedure and purification method used in the preparation of Intermediate 1B, tert-butyl 8-bromo-3,4-dihydroimidazo[1,2-a:5,4-b'] dipyridine-1(2H)-carboxylate (Intermediate 5A, 120 mg, 0.341 mmol) was reacted with 4-(5-(4,4,5,5-tetramethyl-1,3,2-dioxaborolan-2-yl)pyrimidin-2-yl)morpholine (109 mg, 0.375 mmol) to afford tert-butyl 8-(2-morpholinopyrimidin-5-yl)-3,4-dihydroimidazo [1,2-a:5,4-b']dipyridine-1(2H)-carboxylate (120 mg, 0.275 mmol, 81% yield). LC/MS (M+H) 437.3; $^1$H NMR (500 MHz, chloroform-d) δ 8.56 (s, 2H), 8.01 (s, 1H), 7.57 (d, J=9.3 Hz, 1H), 7.25 (dd, J=9.3, 1.7 Hz, 1H), 3.84 (dt, J=33.3, 4.5 Hz, 10H), 2.97 (t, J=6.6 Hz, 2H), 2.12 (dq, J=6.5, 5.8 Hz, 2H), 1.50 (br. s., 9H).

Intermediate 14B: 4-(5-(1,2,3,4-Tetrahydroimidazo [1,2-a:5,4-b']dipyridin-8-yl)pyrimidin-2-yl)morpholine, 2 TFA (14B)

Trifluoroacetic acid (1 mL) was added to a solution of tert-butyl 8-(2-morpholinopyrimidin-5-yl)-3,4-dihydroimidazo[1,2-a:5,4-b']dipyridine-1(2H)-carboxylate (117 mg, 0.268 mmol) in DCM (5 mL). The mixture was allowed to stir at room temperature for 2 h. The reaction mixture was concentrated in vacuo. Residual solvents were removed under high vacuum to afford 4-(5-(1,2,3,4-tetrahydroimidazo [1,2-a:5,4-b']dipyridin-8-yl)pyrimidin-2-yl)morpholine, 2 TFA (155 mg, quantitative yield). Material was used as is without any purification. LC/MS (M+H) 337.2.

Example 14

Following the N-arylation procedure and purification method used in the final step for the preparation of Example 1, 4-(5-(1,2,3,4-tetrahydroimidazo[1,2-a:5,4-b']dipyridin-8-yl)pyrimidin-2-yl)morpholine, 2 TFA (37.8 mg, 0.067 mmol) was reacted with 2-bromo-1,4-dimethylbenzene (24.8 mg, 0.134 mmol) to afford 4-(5-(1-(2,5-dimethylphenyl)-1,2,3,4-tetrahydroimidazo[1,2-a:5,4-b']dipyridin-8-yl)pyrimidin-2-yl) morpholine (5.8 mg, 0.013 mmol, 20% yield). LC/MS (M+H) 441.3; $^1$H NMR (500 MHz, DMSO-$d_6$) δ 8.36 (s, 2H), 7.62-7.50 (m, 1H), 7.35 (d, J=9.2 Hz, 1H), 7.25 (d, J=7.7 Hz, 1H), 7.00 (br. s., 1H), 6.91 (d, J=8.1 Hz, 1H), 6.26 (s, 1H), 3.74-3.60 (m, 8H), 3.60-3.41 (m, 2H), 2.98-2.81 (m, 2H), 2.44 (s, 3H), 2.06 (s, 3H), 2.01-1.79 (m, 2H).

Example 15

4-(5-(1-(2-(Difluoromethoxy)phenyl)-1,2,3,4-tetrahydroimidazo[1,2-a:5,4-b']dipyridin-8-yl)pyrimidin-2-yl)morpholine

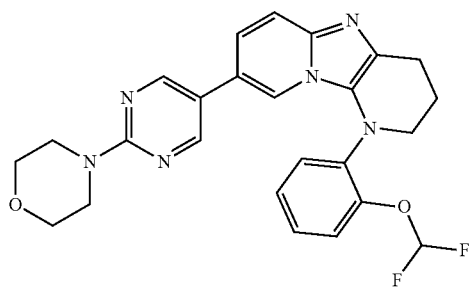

(15)

Following the N-arylation procedure and purification method used in the final step for the preparation of Example 1, 4-(5-(1,2,3,4-tetrahydroimidazo[1,2-a:5,4-b']dipyridin-8-yl)pyrimidin-2-yl)morpholine, 2 TFA (Intermediate 14B, 37.8 mg, 0.067 mmol) was reacted with 1-bromo-2-(difluoromethoxy)benzene (29.9 mg, 0.134 mmol) to afford 4-(5-(1-(2-(difluoromethoxy)phenyl)-1,2,3,4-tetrahydroimidazo[1,2-a:5,4-b']dipyridin-8-yl)pyrimidin-2-yl)morpholine (5.6 mg, 0.012 mmol, 18% yield). LC/MS (M+H) 479.3; $^1$H NMR (500 MHz, DMSO-$d_6$) δ 8.42 (s, 2H), 7.60 (d, J=8.8 Hz, 1H), 7.40 (d, J=9.2 Hz, 1H), 7.35 (t, J=74.5 Hz, 1H), 7.33 (d, J=8.4 Hz, 1H), 7.25-7.20 (m, 1H), 7.17 (t, J=7.5 Hz, 1H), 7.10 (t, J=7.5 Hz, 1H), 6.32 (d, J=8.1 Hz, 1H), 3.77-3.55 (m, 10H), 2.86 (t, J=5.7 Hz, 2H), 1.92-1.79 (m, 2H).

Example 16

2-(4-(1-(2,5-Dimethylphenyl)-1,2,3,4-tetrahydroimidazo[1,2-a:5,4-b']dipyridin-8-yl)phenyl)-5-methyl-1,3,4-oxadiazole

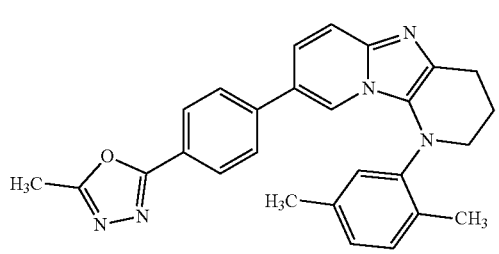

(16)

Intermediate 16A: tert-Butyl 8-(4-(5-methyl-1,3,4-oxadiazol-2-yl)phenyl)-3,4-dihydroimidazo[1,2-a:5,4-b']dipyridine-1(2H)-carboxylate

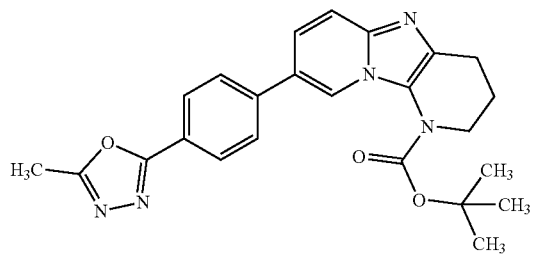

(16A)

Following the metal-mediated coupling procedure and purification method used in the preparation of Intermediate 1B, tert-butyl 8-bromo-3,4-dihydroimidazo[1,2-a:5,4-b']dipyridine-1(2H)-carboxylate (Intermediate 5A, 250 mg, 0.710 mmol) was reacted with (4-(5-methyl-1,3,4-oxadiazol-2-yl)phenyl)boronic acid (159 mg, 0.781 mmol) to afford tert-butyl 8-(4-(5-methyl-1,3,4-oxadiazol-2-yl)phenyl)-3,4-dihydroimidazo[1,2-a:5,4-b']dipyridine-1(2H)-carboxylate (162 mg, 0.375 mmol, 52.9% yield). LC/MS (M+H) 432.2.

Intermediate 16B: 2-Methyl-5-(4-(1,2,3,4-tetrahydroimidazo[1,2-a:5,4-b']dipyridin-8-yl)phenyl)-1,3,4-oxadiazole, 2 TFA

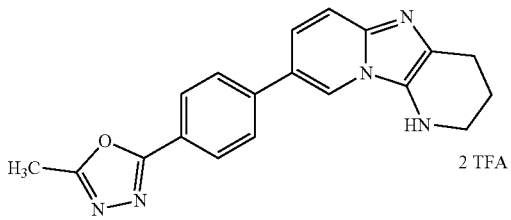

(16B)

Trifluoroacetic acid (1 mL) was added to a solution of tert-butyl 8-(4-(5-methyl-1,3,4-oxadiazol-2-yl)phenyl)-3,4-dihydroimidazo[1,2-a:5,4-b']dipyridine-1(2H)-carboxylate (162 mg, 0.375 mmol) in DCM (5 mL). The mixture was allowed to stir at room temperature for 2 h. The reaction mixture was concentrated in vacuo. Residual solvent were removed under high vacuum to afford 2-methyl-5-(4-(1,2,3,4-tetrahydroimidazo[1,2-a:5,4-b']dipyridin-8-yl)phenyl)-1,3,4-oxadiazole, 2 TFA (242 mg, quantitative yield). Material was used as is without any purification. LC/MS (M+H) 332.1.

Example 16

Following the N-arylation procedure and purification method used in the final step for the preparation of Example 1, 2-methyl-5-(4-(1,2,3,4-tetrahydroimidazo[1,2-a:5,4-b']dipyridin-8-yl)phenyl)-1,3,4-oxadiazole, 2 TFA (50 mg, 0.089 mmol) was reacted with 2-bromo-1,4-dimethylbenzene (33.1 mg, 0.179 mmol) to afford 2-(4-(1-(2,5-dimethylphenyl)-1,2,3,4-tetrahydroimidazo[1,2-a:5,4-b']dipyridin-8-yl)phenyl)-5-methyl-1,3,4-oxadiazole (1.8 mg, 3.89 µmol, 4% yield). LC/MS (M+H) 436.2; $^1$H NMR (500 MHz, DMSO-d$_6$) δ 7.96 (d, J=7.7 Hz, 2H), 7.59 (d, J=9.2 Hz, 1H), 7.54 (d, J=7.7 Hz, 2H), 7.44 (d, J=9.2 Hz, 1H), 7.25 (d, J=7.3 Hz, 1H), 7.14 (s, 1H), 6.91 (d, J=7.7 Hz, 1H), 6.31 (s, 1H), 3.61-3.42 (m, 2H), 2.99-2.81 (m, 2H), 2.58 (s, 3H), 2.45 (s, 3H), 2.06 (s, 3H), 2.01-1.80 (m, 2H).

Example 17

2-(4-(1-(2-(Difluoromethoxy)phenyl)-1,2,3,4-tetrahydroimidazo[1,2-a:5,4-b']dipyridin-8-yl)phenyl)-5-methyl-1,3,4-oxadiazole

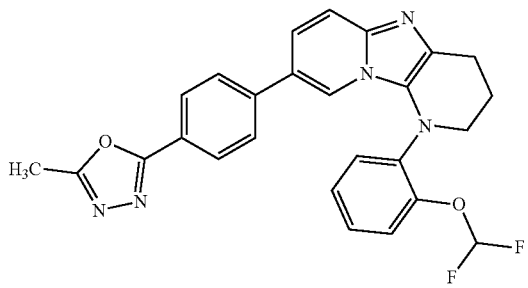
(17)

Following the N-arylation procedure and purification method used in the final step for the preparation of Example 1, 2-methyl-5-(4-(1,2,3,4-tetrahydroimidazo[1,2-a:5,4-b']dipyridin-8-yl)phenyl)-1,3,4-oxadiazole, 2 TFA (Intermediate 16B, 50 mg, 0.089 mmol) was reacted with 1-bromo-2-(difluoromethoxy)benzene (39.9 mg, 0.179 mmol) to afford 2-(4-(1-(2-(difluoromethoxy)phenyl)-1,2,3,4-tetrahydroimidazo[1,2-a:5,4-b']dipyridin-8-yl)phenyl)-5-methyl-1,3,4-oxadiazole (1.8 mg, 3.80 µmol, 4.3% yield). LC/MS (M+H) 474.2; $^1$H NMR (500 MHz, DMSO-d$_6$) δ 8.02-7.93 (m, J=8.1 Hz, 2H), 7.65 (d, J=9.2 Hz, 1H), 7.63-7.58 (m, J=8.1 Hz, 2H), 7.52 (d, J=9.2 Hz, 1H), 7.40 (t, J=74.4 Hz, 1H), 7.39-7.32 (m, 2H), 7.19 (t, J=7.7 Hz, 1H), 7.11 (t, J=7.7 Hz, 1H), 6.40 (d, J=7.7 Hz, 1H), 3.78-3.63 (m, 2H), 2.89 (t, J=6.1 Hz, 2H), 2.58 (s, 3H), 1.94-1.83 (m, 2H).

Example 18

2-(5-(1-(2,5-Dimethylphenyl)-1,2,3,4-tetrahydroimidazo[1,2-a:5,4-b']dipyridin-8-yl)pyrimidin-2-yl)propan-2-ol

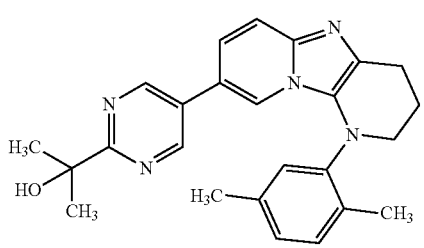
(18)

Intermediate 18A: 8-Bromo-1,2,3,4-tetrahydroimidazo[1,2-a:5,4-b']dipyridine, 2 TFA

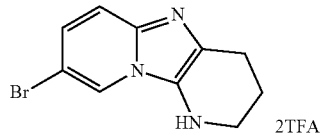
(18A)

Trifluoroacetic acid (1 mL) was added to a solution of tert-butyl 8-bromo-3,4-dihydroimidazo[1,2-a:5,4-b']dipyridine-1(2H)-carboxylate (60 mg, 0.170 mmol) in DCM (5 mL). The mixture was allowed to stir at room temperature for 2 h. The reaction mixture was concentrated in vacuo. Residual solvents were removed under high vacuum to afford 8-bromo-1,2,3,4-tetrahydroimidazo[1,2-a:5,4-b']dipyridine, 2 TFA (84 mg, quantitative yield). Material was used as is without any purification. LC/MS (M+H) 252.0, 254.0.

Intermediate 18B: 2-(5-(1,2,3,4-Tetrahydroimidazo[1,2-a:5,4-b']dipyridin-8-yl)pyrimidin-2-yl)propan-2-ol

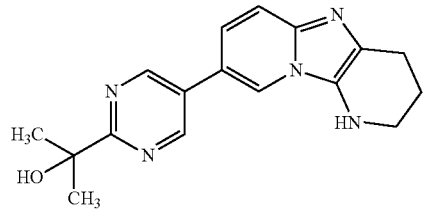
(18B)

Following the metal-mediated coupling procedure and purification method used in preparation of Intermediate 1B, 8-bromo-1,2,3,4-tetrahydroimidazo[1,2-a:5,4-b']dipyridine, 2 TFA (82 mg, 0.170 mmol) was reacted with 2-(5-(4,4,5,5-tetramethyl-1,3,2-dioxaborolan-2-yl)pyrimidin-2-yl)propan-2-ol (49.4 mg, 0.187 mmol) to afford 2-(5-(1,2,3,4-tetrahydroimidazo[1,2-a:5,4-b']dipyridin-8-yl)pyrimidin-2-yl)propan-2-ol (54 mg, 0.175 mmol, quantitative yield) (~86% HPLC UV purity). Material was used as is without any purification. LC/MS (M+H) 310.1.

Example 18

Following the N-arylation procedure and purification method used in the final step for the preparation of Example 1, 2-(5-(1,2,3,4-tetrahydroimidazo[1,2-a:5,4-b']dipyridin-8-yl)pyrimidin-2-yl)propan-2-ol (30.9 mg, 0.100 mmol) was reacted with 2-bromo-1,4-dimethylbenzene (37.0 mg, 0.200 mmol) to afford 2-(5-(1-(2,5-dimethylphenyl)-1,2,3,4-tetrahydroimidazo[1,2-a:5,4-b']dipyridin-8-yl)pyrimidin-2-yl)propan-2-ol (4.4 mg, 10.64 µmol, 11% yield). LC/MS (M+H) 414.1; $^1$H NMR (500 MHz, DMSO-d$_6$) δ 8.77 (s, 2H), 7.62 (d, J=8.8 Hz, 1H), 7.47 (d, J=9.2 Hz, 1H), 7.25 (d, J=7.3 Hz, 1H), 7.18 (s, 1H), 6.91 (d, J=7.7 Hz, 1H), 6.26 (s, 1H), 3.60-3.43 (m, 2H), 3.01-2.79 (m, 2H), 2.45 (s, 3H), 2.06 (s, 3H), 2.00-1.81 (m, 2H), 1.48 (s, 6H).

Example 19

4-(5-(1-(2-(Difluoromethoxy)-5-methylphenyl)-1,2,3,4-tetrahydroimidazo [1,2-a:5,4-b']dipyridin-8-yl)pyrimidin-2-yl)morpholine

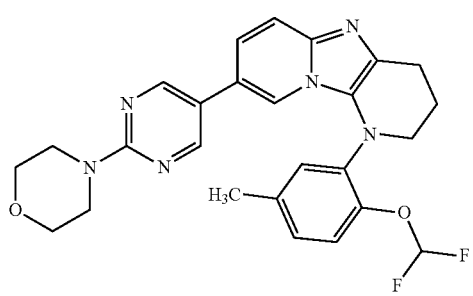

(19)

Intermediate 19A:
2-Bromo-1-(difluoromethoxy)-4-methylbenzene

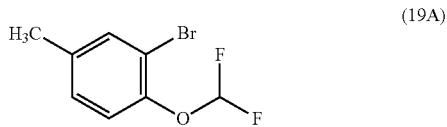

(19A)

Potassium hydroxide (7.50 g, 134 mmol) stirred in a mixture of acetonitrile (25 mL) and water (25 mL) was cooled to approximately −10° C. (ice/methanol bath). 2-Bromo-4-methylphenol (2.5 g, 13.37 mmol) was added dropwise, followed by diethyl (bromodifluoromethyl)phosphonate (7.14 g, 26.7 mmol) over 15 min. The mixture was then allowed to warm to rt over 1 h. The mixture was poured into water and extracted with ethyl acetate. The combined organic layers were washed with brine, dried (magnesium sulfate), filtered, and concentrated in vacuo. The crude product was purified using silica gel column chromatography (10:1 hexanes/ethyl acetate) to afford 2-bromo-1-(difluoromethoxy)-4-methylbenzene (2.35 g, 9.91 mmol, 74.2% yield) as a clear oil. $^1$H NMR (400 MHz, chloroform-d) δ 7.44 (s, 1H), 7.11 (s, 2H), 6.49 (t, J=73.8 Hz, 1H), 2.34 (s, 3H).

Example 19

Following the N-arylation procedure and purification method used in the final step for the preparation of Example 1, 4-(5-(1,2,3,4-tetrahydroimidazo[1,2-a:5,4-b']dipyridin-8-yl)pyrimidin-2-yl)morpholine, 2 TFA (Intermediate 14B, 30.2 mg, 0.067 mmol) was reacted with 2-bromo-1-(difluoromethoxy)-4-methylbenzene (31.8 mg, 0.134 mmol) to afford 4-(5-(1-(2-(difluoromethoxy)-5-methylphenyl)-1,2,3,4-tetrahydroimidazo [1,2-a:5,4-b']dipyridin-8-yl)pyrimidin-2-yl)morpholine (11.2 mg, 0.023 mmol, 34% yield). LC/MS (M+H) 493.3; $^1$H NMR (500 MHz, DMSO-d$_6$) δ 8.43 (s, 2H), 7.59 (d, J=9.5 Hz, 1H), 7.41 (d, J=9.2 Hz, 1H), 7.25-7.18 (m, 2H), 7.29 (t, J=74.5 Hz, 1H), 6.97 (d, J=8.1 Hz, 1H), 6.16 (s, 1H), 3.75-3.57 (m, 9H), 3.33-3.24 (m, 1H), 2.86 (t, J=5.7 Hz, 2H), 2.08 (s, 3H), 1.93-1.75 (m, 2H).

Example 20

1-(2-(Difluoromethoxy)-5-methylphenyl)-8-(6-methoxypyridin-3-yl)-1,2,3,4-tetrahydroimidazo[1,2-a:5,4-b']dipyridine

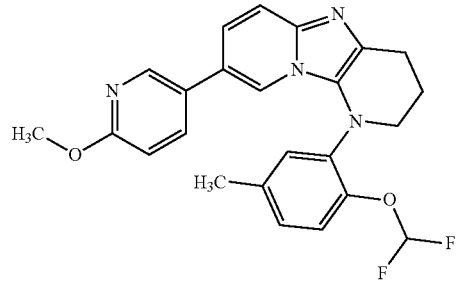

(20)

Following the N-arylation procedure and purification method used in the final step for the preparation of Example 1, 8-(6-methoxypyridin-3-yl)-1,2,3,4-tetrahydroimidazo [1,2-a:5,4-b']dipyridine, TFA (Intermediate 5C, 25 mg, 0.063 mmol) was reacted with 2-bromo-1-(difluoromethoxy)-4-methylbenzene (Intermediate 19A, 30.1 mg, 0.127 mmol) to afford 1-(2-(difluoromethoxy)-5-methylphenyl)-8-(6-methoxypyridin-3-yl)-1,2,3,4-tetrahydroimidazo [1,2-a:5,4-b']dipyridine (11.5 mg, 0.026 mmol, 41.6% yield). LC/MS (M+H) 437.2; $^1$H NMR (500 MHz, DMSO-d$_6$) δ 8.15 (br. s., 1H), 7.77 (d, J=8.1 Hz, 1H), 7.61 (d, J=8.8 Hz, 1H), 7.42 (d, J=8.8 Hz, 1H), 7.25 (s, 1H), 7.22 (d, J=8.1 Hz, 1H), 7.31 (t, J=74.5 Hz, 1H), 6.98 (d, J=7.3 Hz, 1H), 6.88 (d, J=8.4 Hz, 1H), 6.19 (s, 1H), 3.85 (s, 3H), 3.77-3.54 (m, 2H), 2.93-2.80 (m, 2H), 2.08 (s, 3H), 1.87 (br. s., 2H).

Example 21

2-(5-(7-Chloro-1-phenyl-1,2,3,4-tetrahydroimidazo [1,2-a:5,4-b']dipyridin-8-yl)pyrimidin-2-yl)propan-2-ol

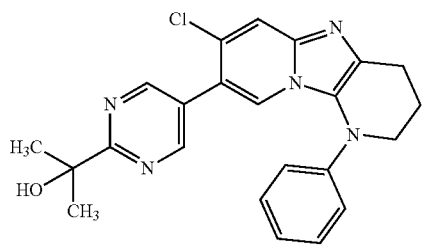

(21)

Intermediate 21A: tert-Butyl 8-bromo-7-chloro-3,4-dihydroimidazo[1,2-a:5,4-b']dipyridine-1(2H)-carboxylate

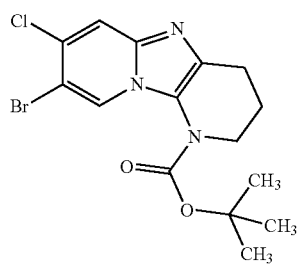

(21A)

A mixture of 5-bromo-4-chloropyridin-2-amine (2.62 g, 12.65 mmol), tert-butyl 3-oxopiperidine-1-carboxylate (2.52 g, 12.65 mmol), tert-butyl 3-oxopiperidine-1-carboxylate (2.52 g, 12.65 mmol), and acetic acid acetic acid (0.072 mL, 1.27 mmol) in toluene (100 mL) was heated to reflux. Water was azeotroped using a Dean-Stark apparatus. The mixture was heated at reflux for 3 days. After cooling to room temperature, air was bubbled through the reaction mixture for 2 h to promote oxidative dehydrogenation. The resulting dark solution was concentrated under high vacuum to afford a black oil. The oil was diluted with ethyl acetate and washed with saturated aqueous sodium bicarbonate solution. The aqueous portion was back extracted with ethyl acetate. The combined organic portions were washed with brine, dried over magnesium sulfate, filtered and concentrated in vacuo. The crude product was purified using silica gel column chromatography (100% EtOAc) to afford tert-butyl 8-bromo-7-chloro-3,4-dihydroimidazo[1,2-a:5,4-b']dipyridine-1(2H)-carboxylate (998 mg, 2.58 mmol, 20% yield). A portion was recrystallized from ethyl acetate/hexanes to afford an analytical sample. LC/MS (M+H) 386.0, 388.0; $^1$H NMR (500 MHz, DMSO-$d_6$) δ 8.43 (br. s., 1H), 7.95-7.83 (m, 1H), 3.69 (br. s., 2H), 2.81 (t, J=6.6 Hz, 2H), 1.97 (dq, J=6.4, 5.7 Hz, 2H), 1.44 (br. s., 9H).

Intermediate 21B: 8-Bromo-7-chloro-1,2,3,4-tetrahydroimidazo[1,2-a:5,4-b']dipyridine, 2 TFA

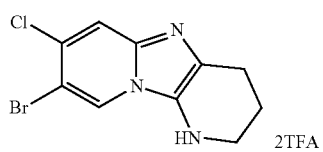

(21B)

Trifluoroacetic acid (1 mL) was added to a solution of tert-butyl 8-bromo-7-chloro-3,4-dihydroimidazo[1,2-a:5,4-b']dipyridine-1(2H)-carboxylate (250 mg, 0.647 mmol) in DCM (5 mL). The mixture was allowed to stir at room temperature for 2 h. The reaction mixture was concentrated in vacuo. Residual solvents were removed under high vacuum to afford 8-bromo-7-chloro-1,2,3,4-tetrahydroimidazo[1,2-a:5,4-b']dipyridine, 2 TFA (335 mg, quantitative yield). Material was used as is without any purification. LC/MS (M+H) 285.9, 287.9.

Intermediate 21C: 2-(5-(7-Chloro-1,2,3,4-tetrahydroimidazo[1,2-a:5,4-b']dipyridin-8-yl)pyrimidin-2-yl)propan-2-ol

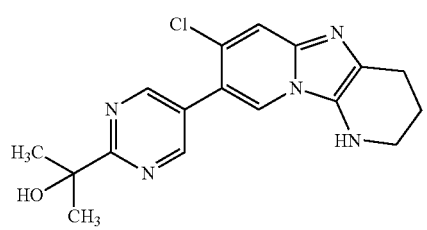

(21C)

Following the metal-mediated coupling procedure used in preparation of Intermediate 1B, 8-bromo-7-chloro-1,2,3,4-tetrahydroimidazo[1,2-a:5,4-b']dipyridine, 2 TFA (333 mg, 0.647 mmol) was reacted with (2-(2-hydroxypropan-2-yl)pyrimidin-5-yl)boronic acid (130 mg, 0.712 mmol). The crude reaction product was purified using silica gel column chromatography (10% MeOH/EtOAc) to afford 2-(5-(7-chloro-1,2,3,4-tetrahydroimidazo[1,2-a:5,4-b']dipyridin-8-yl)pyrimidin-2-yl)propan-2-ol (34 mg, 0.099 mmol, 15% yield). LC/MS (M+H) 344.1.

Example 21

Following the N-arylation procedure and purification method used in the final step for the preparation of Example 1, 2-(5-(7-chloro-1,2,3,4-tetrahydroimidazo[1,2-a:5,4-b']dipyridin-8-yl)pyrimidin-2-yl)propan-2-ol (17 mg, 0.049 mmol) was reacted with bromobenzene (15.53 mg, 0.099 mmol) to afford 2-(5-(7-chloro-1-phenyl-1,2,3,4-tetrahydroimidazo[1,2-a:5,4-b']dipyridin-8-yl)pyrimidin-2-yl)propan-2-ol (2.1 mg, 5.00 mol, 10% yield). LC/MS (M+H) 420.2; $^1$H NMR (500 MHz, DMSO-$d_6$) δ 8.77 (s, 2H), 7.92 (s, 1H), 7.35 (s, 1H), 7.29 (t, J=7.5 Hz, 2H), 6.99 (t, J=7.3 Hz, 1H), 6.74 (d, J=8.4 Hz, 2H), 3.86-3.75 (m, 2H), 3.34 (br. s., 1H), 2.89-2.85 (m, 2H), 1.88-1.81 (m, 2H), 1.49 (s, 6H).

Example 22

7-Chloro-1-(2-(difluoromethoxy)phenyl)-8-(6-methoxypyridin-3-yl)-1,2,3,4-tetrahydroimidazo[1,2-a:5,4-b']dipyridine

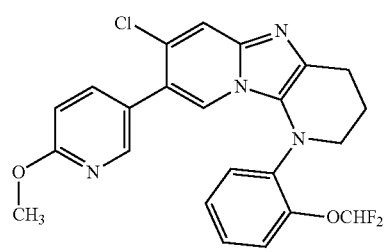

(22)

Intermediate 22A: tert-Butyl 7-chloro-8-(6-methoxypyridin-3-yl)-3,4-dihydroimidazo [1,2-a:5,4-b']dipyridine-1(2H)-carboxylate

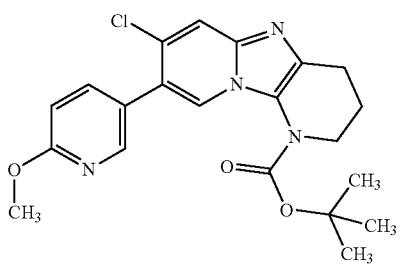

(22A)

Following the metal-mediated coupling procedure and purification method used in the preparation of Intermediate 1B, tert-butyl 8-bromo-7-chloro-3,4-dihydroimidazo [1,2-a:5,4-b']dipyridine-1(2H)-carboxylate (Intermediate 21A, 0.200 g, 0.517 mmol) was reacted with (6-methoxypyridin-3-yl)boronic acid (0.079 g, 0.517 mmol) to afford tert-butyl 7-chloro-8-(6-methoxypyridin-3-yl)-3,4-dihydroimidazo[1,2-a:5,4-b']dipyridine-1(2H)-carboxylate (220 mg, 0.498 mmol, 96% yield). LC/MS (M+H) 415.1; $^1$H NMR (500 MHz, DMSO-$d_6$) δ 8.25 (s, 1H), 8.04 (br. s., 1H), 7.90-7.75 (m, 2H), 6.96 (d, J=8.8 Hz, 1H), 3.99-3.88 (m, 3H), 3.71 (br. s., 2H), 2.84 (t, J=6.2 Hz, 2H), 2.00 (br. s., 2H), 1.36 (br. s., 9H).

Intermediate 22B: 7-Chloro-8-(6-methoxypyridin-3-yl)-1,2,3,4-tetrahydroimidazo [1,2-a:5,4-b']dipyridine, 2 TFA

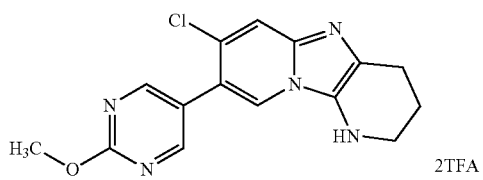

(22B)

2TFA

Trifluoroacetic acid (1 mL) was added to a solution of tert-butyl 7-chloro-8-(6-methoxypyridin-3-yl)-3,4-dihydroimidazo[1,2-a:5,4-b']dipyridine-1(2H)-carboxylate (Intermediate 22A, 210 mg, 0.506 mmol) in DCM (5 mL). The mixture was allowed to stir at room temperature for 2 h. The reaction mixture was concentrated in vacuo. Residual solvents were removed under high vacuum to afford 7-chloro-8-(6-methoxypyridin-3-yl)-1,2,3,4-tetrahydroimidazo[1,2-a:5,4-b']dipyridine, 2 TFA (261 mg, 95% yield). Material was used as is without any purification. LC/MS (M+H) 314.9. $^1$H NMR (500 MHz, DMSO-$d_6$) δ 8.26 (s, 1H), 8.08 (s, 1H), 7.85 (d, J=8.1 Hz, 1H), 7.71 (s, 1H), 6.96 (d, J=8.8 Hz, 1H), 3.92 (s, 4H), 2.78 (t, J=6.1 Hz, 2H), 2.55 (s, 2H), 1.91 (br. s., 2H).

Example 22

Following the N-arylation procedure and purification method used in the final step for the preparation of Example 1, 7-chloro-8-(6-methoxypyridin-3-yl)-1,2,3,4-tetrahydroimidazo[1,2-a:5,4-b']dipyridine, 2 TFA (50 mg, 0.092 mmol) was reacted with 1-bromo-2-(difluoromethoxy)benzene (71 mg, 0.32 mmol) to afford 7-chloro-1-(2-(difluoromethoxy)phenyl)-8-(6-methoxypyridin-3-yl)-1,2,3,4-tetrahydroimidazo [1,2-a:5,4-b']dipyridine (2.5 mg, 0.005 mmol, 5.4% yield). LC/MS (M+H) 457.0; $^1$H NMR (500 MHz, DMSO-$d_6$) δ 7.95 (s, 1H), 7.84 (s, 1H), 7.69 (d, J=8.4 Hz, 1H), 7.34-7.24 (m, 1H), 7.20-7.07 (m, 4H), 6.86 (d, J=8.4 Hz, 1H), 6.39 (d, J=7.3 Hz, 1H), 3.85 (s, 3H), 3.69 (br. s., 2H), 2.89 (d, J=10.3 Hz, 2H), 1.93-1.72 (m, 2H).

Example 23

7-Chloro-1-(2,5-dimethylphenyl)-8-(6-methoxypyridin-3-yl)-1,2,3,4-tetrahydroimidazo[1,2-a:5,4-b'] dipyridine

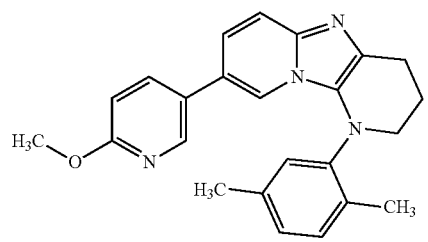

(23)

Following the N-arylation procedure and purification method used in the final step for the preparation of Example 1, 7-chloro-8-(6-methoxypyridin-3-yl)-1,2,3,4-tetrahydroimidazo[1,2-a:5,4-b']dipyridine, 2 TFA (50 mg, 0.092 mmol) was reacted with 2-bromo-1,4-dimethylbenzene (0.059 g, 0.318 mmol) to afford 7-chloro-1-(2,5-dimethylphenyl)-8-(6-methoxypyridin-3-yl)-1,2,3,4-tetrahydroimidazo[1,2-a:5,4-b']dipyridine (2.9 mg, 6.65 μmol, 7.2% yield). LC/MS (M+H) 419.2; $^1$H NMR (500 MHz, DMSO-$d_6$) δ 7.89 (s, 1H), 7.79 (s, 1H), 7.64 (d, J=7.7 Hz, 1H), 7.19 (d, J=7.7 Hz, 1H), 6.95-6.77 (m, 3H), 6.27 (s, 1H), 3.85 (s, 5H), 2.92 (br. s., 3H), 2.09 (d, J=13.2 Hz, 6H), 1.88 (br. s., 1H).

Example 24

1-(2,3-Dimethylphenyl)-8-(6-methoxypyridin-3-yl)-1,2,3,4-tetrahydroimidazo [1,2-a:5,4-b']dipyridine

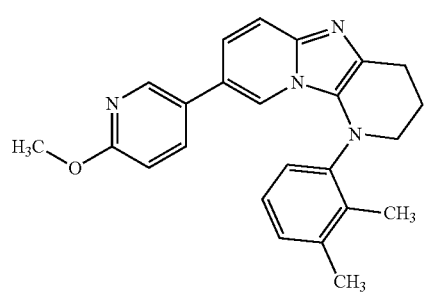

(24)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 1-bromo-2,3-dimethylbenzene (12.9 mg, 0.070 mmol) to afford 1-(2,3-dimethylphenyl)-8-(6-methoxypyridin-3-yl)-1,2,3,4-tetrahydroimidazo[1,2-a:5,4-b']dipyridine (11.8 mg, 0.031 mmol, 48% yield). LC/MS (M+H) 385.2; $^1$H NMR (500 MHz, DMSO-d$_6$) δ 8.08 (s, 1H), 7.70 (d, J=8.4 Hz, 1H), 7.56 (d, J=9.2 Hz, 1H), 7.33 (d, J=9.5 Hz, 1H), 7.05 (s, 1H), 7.00 (d, J=7.7 Hz, 1H), 6.93 (t, J=7.9 Hz, 1H), 6.86 (d, J=8.4 Hz, 1H), 6.24 (d, J=8.1 Hz, 1H), 3.84 (s, 3H), 3.67-3.53 (m, 1H), 3.52-3.38 (m, 1H), 2.96-2.79 (m, 2H), 2.42 (s, 3H), 2.33 (s, 3H), 1.96-1.75 (m, 2H).

Example 25

1-(5-Fluoro-2-methylphenyl)-8-(6-methoxypyridin-3-yl)-1,2,3,4-tetrahydroimidazo [1,2-a:5,4-b']dipyridine

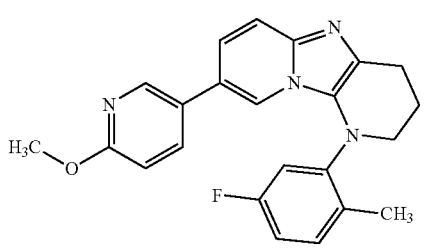

(25)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 2-bromo-4-fluoro-1-methylbenzene (23.97 mg, 0.127 mmol) to afford 1-(5-fluoro-2-methylphenyl)-8-(6-methoxypyridin-3-yl)-1,2,3,4-tetrahydroimidazo[1,2-a:5,4-b']dipyridine (10.6 mg, 0.027 mmol, 43% yield). LC/MS (M+H) 389.2; $^1$H NMR (500 MHz, DMSO-d$_6$) δ 8.14 (s, 1H), 7.75 (dd, J=8.6, 2.4 Hz, 1H), 7.64 (d, J=9.5 Hz, 1H), 7.46 (d, J=9.5 Hz, 1H), 7.41 (t, J=7.5 Hz, 1H), 7.10 (s, 1H), 6.99-6.90 (m, 1H), 6.88 (d, J=8.8 Hz, 1H), 6.22 (d, J=9.9 Hz, 1H), 3.85 (s, 3H), 3.56 (br. s., 2H), 3.01-2.83 (m, 2H), 2.47 (s, 3H), 2.00-1.81 (m, 2H).

Example 26

1-(4-Fluoro-2-methylphenyl)-8-(6-methoxypyridin-3-yl)-1,2,3,4-tetrahydroimidazo [1,2-a:5,4-b']dipyridine

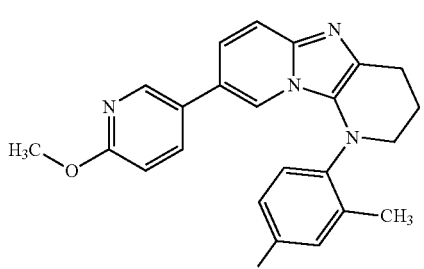

(26)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 1-bromo-4-fluoro-2-methylbenzene (36.0 mg, 0.190 mmol) to afford 1-(4-fluoro-2-methylphenyl)-8-(6-methoxypyridin-3-yl)-1,2,3,4-tetrahydroimidazo[1,2-a:5,4-b']dipyridine (3.6 mg, 9.3 μmol, 15% yield). LC/MS (M+H) 389.1; $^1$H NMR (500 MHz, DMSO-d$_6$) δ 8.12 (s, 1H), 7.73 (d, J=8.8 Hz, 1H), 7.59 (d, J=8.1 Hz, 1H), 7.41 (d, J=8.8 Hz, 1H), 7.25 (d, J=9.2 Hz, 1H), 7.08 (br. s., 1H), 6.91-6.81 (m, 2H), 6.50-6.40 (m, 1H), 3.85 (s, 3H), 3.44 (br. s., 2H), 2.90 (br. s., 2H), 2.47 (s, 3H), 1.88 (br. s., 2H).

Example 27

1-(2-Methoxy-5-methylphenyl)-8-(6-methoxypyridin-3-yl)-1,2,3,4-tetrahydroimidazo[1,2-a:5,4-b']dipyridine

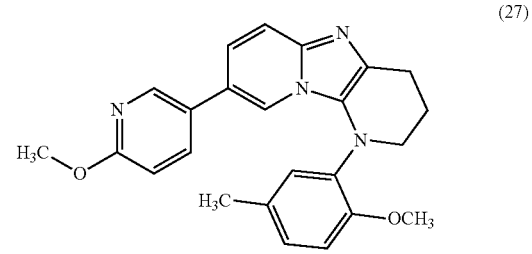 [SMILES: COc1ccc(-c2ccc3nc4c(n3c2)N(c2cc(C)ccc2OC)CCC4)cn1]

(27)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 35 mg, 0.089 mmol) was reacted with 2-bromo-1-methoxy-4-methylbenzene (89 mg, 0.444 mmol) to afford 1-(2-methoxy-5-methylphenyl)-8-(6-methoxypyridin-3-yl)-1,2,3,4-tetrahydroimidazo[1,2-a:5,4-b']dipyridine (9.1 mg, 22 μmol, 25% yield). LC/MS (M+H) 401.1; $^1$H NMR (500 MHz, DMSO-d$_6$) δ 8.12 (s, 1H), 7.74 (d, J=8.4 Hz, 1H), 7.58 (d, J=9.2 Hz, 1H), 7.38 (d, J=9.2 Hz, 1H), 7.10 (s, 1H), 7.04 (d, J=8.4 Hz, 1H), 6.95-6.83 (m, 2H), 6.06 (s, 1H), 3.85 (s, 3H), 3.87 (s, 3H), 3.71-3.54 (m, 2H), 2.86 (br. s., 2H), 2.03 (s, 3H), 1.89-1.76 (m, 2H).

Example 28

1-(2-Ethylphenyl)-8-(6-methoxypyridin-3-yl)-1,2,3,4-tetrahydroimidazo [1,2-a:5,4-b']dipyridine

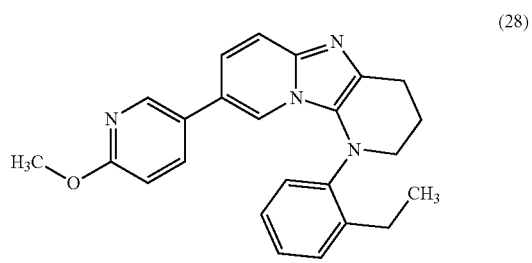 [SMILES: CCc1ccccc1N1CCCc2nc3ccc(-c4ccc(OC)nc4)cn3c21]

(28)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 1-bromo-2-ethylbenzene (35.2 mg, 0.190 mmol) to afford 1-(2-ethylphenyl)-8-(6-methoxypyridin-3-yl)-1,2,3,4-tetrahydroimidazo[1,2-a:5,4-b']dipyridine (9.7 mg, 25 µmol, 40% yield). LC/MS (M+H) 385.2; $^1$H NMR (500 MHz, DMSO-$d_6$) δ 8.05 (s, 1H), 7.66 (t, J=8.1 Hz, 2H), 7.53-7.40 (m, 2H), 7.18 (t, J=7.2 Hz, 1H), 7.11-7.03 (m, 2H), 6.87 (d, J=8.4 Hz, 1H), 6.53 (d, J=7.7 Hz, 1H), 3.84 (s, 3H), 3.65 (t, J=12.3 Hz, 1H), 3.48 (d, J=12.1 Hz, 1H), 3.06 (dd, J=14.5, 7.2 Hz, 1H), 2.91 (d, J=27.9 Hz, 2H), 2.83-2.74 (m, 1H), 1.95 (br. s., 2H), 1.34 (t, J=7.5 Hz, 3H).

Example 29

8-(6-Methoxypyridin-3-yl)-1-(2-(trifluoromethoxy)phenyl)-1,2,3,4-tetrahydroimidazo[1,2-a:5,4-b']dipyridine

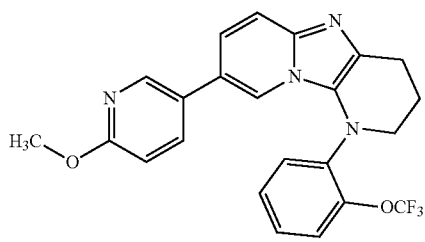

(29)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 1-bromo-2-(trifluoromethoxy)benzene (30.6 mg, 0.127 mmol) to afford 8-(6-methoxypyridin-3-yl)-1-(2-(trifluoromethoxy)phenyl)-1,2,3,4-tetrahydroimidazo [1,2-a:5,4-b']dipyridine (8.4 mg, 19 µmol, 30% yield). LC/MS (M+H) 441.2; $^1$H NMR (500 MHz, DMSO-$d_6$) δ 8.08 (s, 1H), 7.68 (d, J=8.4 Hz, 1H), 7.63 (d, J=9.5 Hz, 1H), 7.53 (br. s., 1H), 7.43 (d, J=9.2 Hz, 1H), 7.29-7.21 (m, 2H), 7.05 (s, 1H), 6.88 (d, J=8.8 Hz, 1H), 6.57-6.49 (m, 1H), 3.84 (s, 3H), 3.69 (br. s., 2H), 2.93-2.81 (m, 2H), 1.94-1.83 (m, 2H).

Example 30

1-(2,4-Dimethylphenyl)-8-(6-methoxypyridin-3-yl)-1,2,3,4-tetrahydroimidazo[1,2-a:5,4-b']dipyridine

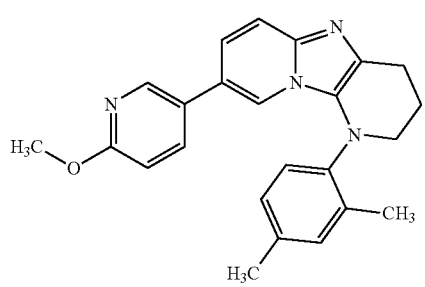

(30)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 1-bromo-2,4-dimethylbenzene (23.46 mg, 0.127 mmol) to afford 1-(2,4-dimethylphenyl)-8-(6-methoxypyridin-3-yl)-1,2,3,4-tetrahydroimidazo[1,2-a:5,4-b']dipyridine (11 mg, 27 µmol, 43% yield). LC/MS (M+H) 385.2; $^1$H NMR (500 MHz, DMSO-$d_6$) δ 8.13 (d, J=2.2 Hz, 1H), 7.72 (dd, J=8.8, 2.6 Hz, 1H), 7.56 (d, J=9.2 Hz, 1H), 7.34 (d, J=9.2 Hz, 1H), 7.18 (s, 1H), 7.05 (s, 1H), 6.86 (d, J=8.4 Hz, 1H), 6.83 (d, J=8.1 Hz, 1H), 6.30 (d, J=8.1 Hz, 1H), 3.85 (s, 3H), 3.62-3.48 (m, 1H), 3.48-3.39 (m, 1H), 2.96-2.80 (m, 2H), 2.48 (s, 3H), 2.23 (s, 3H), 1.98-1.84 (m, 2H).

Example 31

1-(2-Chlorophenyl)-8-(6-methoxypyridin-3-yl)-1,2,3,4-tetrahydroimidazo[1,2-a:5,4-b']dipyridine

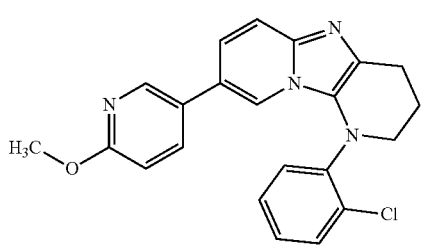

(31)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 1-bromo-2-chlorobenzene (24.27 mg, 0.127 mmol) to afford 1-(2-chlorophenyl)-8-(6-methoxypyridin-3-yl)-1,2,3,4-tetrahydroimidazo[1,2-a:5,4-b']dipyridine (11 mg, 27 µmol, 43% yield). LC/MS (M+H) 391.1; $^1$H NMR (500 MHz, DMSO-$d_6$) δ 8.09 (s, 1H), 7.70 (dd, J=8.6, 2.4 Hz, 1H), 7.63 (d, J=9.2 Hz, 2H), 7.44 (d, J=9.5 Hz, 1H), 7.25-7.17 (m, 2H), 7.04 (s, 1H), 6.86 (d, J=8.4 Hz, 1H), 6.59-6.50 (m, 1H), 3.84 (s, 3H), 3.79-3.59 (m, 2H), 2.90 (t, J=5.1 Hz, 2H), 1.91 (t, J=5.0 Hz, 2H).

Example 32

1-(5-Chloro-2-methylphenyl)-8-(6-methoxypyridin-3-yl)-1,2,3,4-tetrahydroimidazo[1,2-a:5,4-b']dipyridine

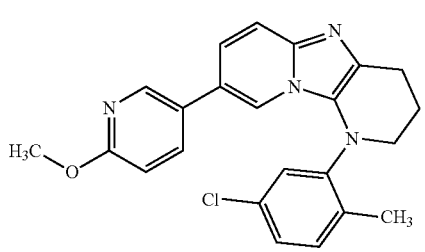

(32)

Following the N-arylation procedure and purification method used in the final step for the preparation of Example 1, 8-(6-methoxypyridin-3-yl)-1,2,3,4-tetrahydroimidazo[1,2-a:5,4-b']dipyridine, TFA (Intermediate 5C, 25 mg, 0.063 mmol) was reacted with 2-bromo-4-chloro-1-methylbenzene (26.1 mg, 0.127 mmol) to afford 1-(5-chloro-2-methylphenyl)-8-(6-methoxypyridin-3-yl)-1,2,3,4-tetrahydroimidazo[1,2-a:5,4-b']dipyridine (9.1 mg, 22 μmol, 36% yield). LC/MS (M+H) 405.1; $^1$H NMR (500 MHz, DMSO-d$_6$) δ 8.14 (d, J=1.8 Hz, 1H), 7.76 (dd, J=8.6, 2.4 Hz, 1H), 7.62 (d, J=9.2 Hz, 1H), 7.47-7.37 (m, 2H), 7.16 (d, J=8.1 Hz, 1H), 7.09 (s, 1H), 6.88 (d, J=8.4 Hz, 1H), 6.37 (s, 1H), 3.85 (s, 3H), 3.61-3.52 (m, 2H), 2.99-2.79 (m, 2H), 2.48 (s, 3H), 1.97-1.84 (m, 2H).

Example 33

4-(5-(1-(2,5-Dimethylphenyl)-1,2,3,4-tetrahydroimidazo[1,2-a:5,4-b']dipyridin-8-yl)pyrimidin-2-yl)morpholine

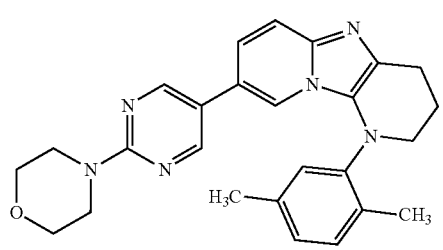

(33)

Following the N-arylation procedure and purification method used in the final step for the preparation of Example 1, 4-(5-(1,2,3,4-tetrahydroimidazo[1,2-a:5,4-b']dipyridin-8-yl)pyrimidin-2-yl)morpholine, 2 TFA (Intermediate 14B, 37.8 mg, 0.067 mmol) was reacted with 2-bromo-1,4-dimethylbenzene (24.80 mg, 0.134 mmol) to afford 4-(5-(1-(2,5-dimethylphenyl)-1,2,3,4-tetrahydroimidazo[1,2-a:5,4-b']dipyridin-8-yl)pyrimidin-2-yl)morpholine (9.1 mg, 22 μmol, 36% yield). LC/MS (M+H) 441.3; $^1$H NMR (500 MHz, DMSO-d$_6$) δ 8.36 (s, 2H), 7.62-7.50 (m, 1H), 7.35 (d, J=9.2 Hz, 1H), 7.25 (d, J=7.7 Hz, 1H), 7.00 (br. s., 1H), 6.91 (d, J=8.1 Hz, 1H), 6.26 (s, 1H), 3.74-3.60 (m, 8H), 3.60-3.41 (m, 2H), 2.98-2.81 (m, 2H), 2.44 (s, 3H), 2.06 (s, 3H), 2.01-1.79 (m, 2H).

Example 34

2-(5-(1-(2-(Difluoromethoxy)phenyl)-1,2,3,4-tetrahydroimidazo[1,2-a:5,4-b']dipyridin-8-yl)pyrimidin-2-yl)propan-2-ol

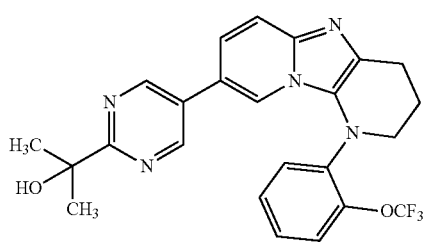

(34)

Following the N-arylation procedure and purification method used in the final step for the preparation of Example 1, 2-(5-(1,2,3,4-tetrahydroimidazo[1,2-a:5,4-b']dipyridin-8-yl)pyrimidin-2-yl)propan-2-ol (Intermediate 18B, 30 mg, 0.97 mmol) was reacted with 1-bromo-2-(difluoromethoxy)benzene (87 mg, 0.388 mmol) to afford 2-(5-(1-(2-(difluoromethoxy)phenyl)-1,2,3,4-tetrahydroimidazo[1,2-a:5,4-b']dipyridin-8-yl)pyrimidin-2-yl)propan-2-ol (14.1 mg, 31 μmol, 32% yield). LC/MS (M+H) 452.2; $^1$H NMR (500 MHz, DMSO-d$_6$) δ 8.84 (s, 2H), 7.68 (d, J=9.5 Hz, 1H), 7.54 (d, J=9.2 Hz, 1H), 7.45 (s, 1H), 7.36 (t, J=74.1 Hz, 1H), 7.34 (d, J=8.1 Hz, 1H), 7.19 (dd, J=13.8, 6.4 Hz, 1H), 7.11 (t, J=7.5 Hz, 1H), 6.35 (d, J=7.7 Hz, 1H), 3.81-3.62 (m, 2H), 2.94-2.84 (m, 3H), 1.90-1.80 (m, 2H), 1.49 (s, 6H).

Example 35

2-(4-(1-(2-(Difluoromethoxy)phenyl)-1,2,3,4-tetrahydroimidazo[1,2-a:5,4-b']dipyridin-8-yl)phenyl)propan-2-ol

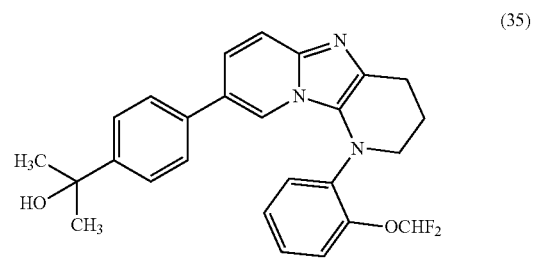 [SMILES: CC(C)(O)c1ccc(-c2ccc3nc4c(n3c2)N(c2ccccc2OC(F)F)CCC4)cc1]

(35)

Intermediate 35A: 2-(4-(1,2,3,4-Tetrahydroimidazo[1,2-a:5,4-b']dipyridin-8-yl)phenyl) propan-2-ol

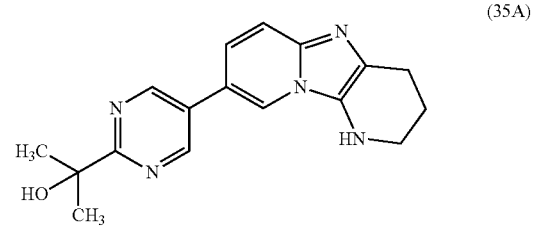 [SMILES: CC(C)(O)c1ncc(-c2ccc3nc4c(n3c2)NCCC4)cn1]

(35A)

Following the metal-mediated coupling procedure and purification method used in preparation of Intermediate 1B, 8-bromo-1,2,3,4-tetrahydroimidazo[1,2-a:5,4-b']dipyridine, (Intermediate 18A, 61.6 mg, 0.244 mmol) was reacted with (4-(2-hydroxypropan-2-yl)phenyl)boronic acid (44 mg, 0.244 mmol) to afford 2-(4-(1,2,3,4-tetrahydroimidazo[1,2-a:5,4-b']dipyridin-8-yl)phenyl)propan-2-ol (67 mg, 0.218 mmol, 89% yield). Material was used as is without any purification. LC/MS (M+H) 308.2.

Example 35

Following the N-arylation procedure and purification method used in the final step for the preparation of Example 1, 2-(4-(1,2,3,4-tetrahydroimidazo[1,2-a:5,4-b']dipyridin-8-yl)phenyl)propan-2-ol (Intermediate 35A, 29 mg, 0.094 mmol) was reacted with 1-bromo-2-(difluoromethoxy)benzene (0.063 g, 0.283 mmol) to afford 2-(4-(1-(2-(difluoromethoxy)phenyl)-1,2,3,4-tetrahydroimidazo[1,2-a:5,4-b']dipyridin-8-yl)phenyl)propan-2-ol (3.1 mg, 6.9 μmol, 7.3% yield). LC/MS (M+H) 450.1; ¹H NMR (500 MHz, DMSO-d₆) δ ¹H NMR (500 MHz, DMSO-d₆) δ 8.02 (q, J=9.3 Hz, 2H), 7.56-7.43 (m, 3H), 7.42-7.23 (m, 5H), 7.20-7.03 (m, 2H), 6.80 (d, J=8.1 Hz, 1H), 3.74 (br. s., 2H), 2.98 (br. s., 2H), 1.93 (br. s., 2H), 1.41 (s, 6H).

Example 36

2-(4-(1-(2,5-Dimethylphenyl)-1,2,3,4-tetrahydroimidazo[1,2-a:5,4-b']dipyridin-8-yl)phenyl)propan-2-ol

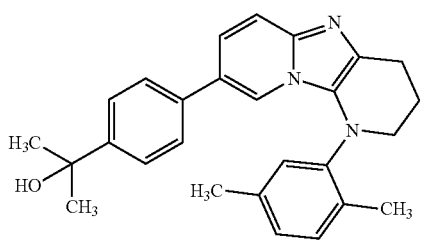

(36)

Following the N-arylation procedure and purification method used in the final step for the preparation of Example 1, 2-(4-(1,2,3,4-tetrahydroimidazo[1,2-a:5,4-b']dipyridin-8-yl)phenyl)propan-2-ol (Intermediate 35A, 38 mg, 0.124 mmol)) was reacted with 2-bromo-1,4-dimethylbenzene (0.069 g, 0.371 mmol) to afford 2-(4-(1-(2,5-dimethylphenyl)-1,2,3,4-tetrahydroimidazo[1,2-a:5,4-b']dipyridin-8-yl)phenyl)propan-2-ol (1.4 mg, 2.7 μmol, 2.2% yield). LC/MS (M+H) 412.2; ¹H NMR (500 MHz, DMSO-d₆) δ 7.96 (s, 2H), 7.52-6.97 (m, 8H), 6.57 (s, 1H), 3.61-3.52 (m, 2H), 3.10-2.91 (m, 2H), 2.46 (s, 3H), 2.09 (s, 3H), 1.97 (br. s., 2H), 1.41 (s, 6H).

Example 37

1-(2,5-Dimethylphenyl)-8-(6-methoxypyridin-3-yl)-4-methyl-1,2,3,4-tetrahydroimidazo[1,2-a:5,4-b']dipyridine

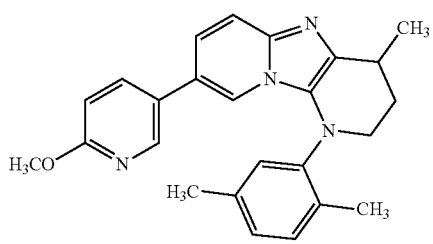

(37)

Intermediate 37A: tert-Butyl 8-bromo-4-methyl-3,4-dihydroimidazo[1,2-a:5,4-b']dipyridine-1(2H)-carboxylate

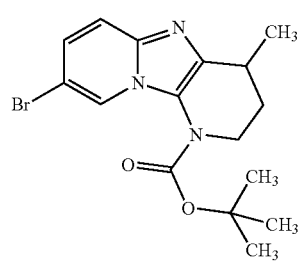

(37A)

A mixture of 5-bromopyridin-2-amine (1.622 g, 9.38 mmol), tert-butyl 4-methyl-3-oxopiperidine-1-carboxylate (2.0 g, 9.38 mmol), and acetic acid (0.054 mL, 0.938 mmol) in toluene (100 mL) was heated to reflux. Water was azeotroped using a Dean-Stark apparatus. The mixture was heated at reflux for 3 days. After cooling to room temperature, air was bubbled through the reaction mixture for 2 h to promote oxidative dehydrogenation. The resulting black solution was concentrated under high vacuum to afford a black oil. The black oil was diluted with ethyl acetate and washed with saturated aqueous sodium bicarbonate solution. The aqueous portion was back extracted with ethyl acetate. The combined organic portions were washed with brine, dried over magnesium sulfate, filtered and concentrated in vacuo. The crude product was purified twice using silica gel column chromatography (100% EtOAc) to afford a total combined mass of 1.05 g of an inseparable mixture (~1:1) of starting 5-bromopyridin-2-amine and tert-butyl 8-bromo-4-methyl-3,4-dihydroimidazo[1,2-a:5,4-b']dipyridine-1(2H)-carboxylate (~7% yield). The mixture was used for subsequent chemistry without further purification. LC/MS (M+H) 366.1, 368.1.

Intermediate 37B: tert-Butyl 8-(6-methoxypyridin-3-yl)-4-methyl-3,4-dihydroimidazo [1,2-a:5,4-b']dipyridine-1(2H)-carboxylate

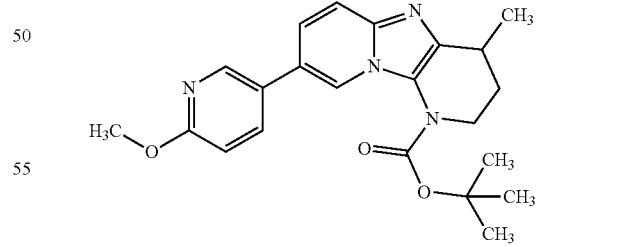

(37B)

Following the metal-mediated coupling procedure and purification method used in the preparation of Intermediate 1B, tert-butyl 8-bromo-4-methyl-3,4-dihydroimidazo [1,2-a:5,4-b']dipyridine-1(2H)-carboxylate (impure Intermediate 37A, 300 mg, 0.819 mmol) was reacted with (6-methoxypyridin-3-yl)boronic acid (188 mg, 1.23 mmol) to afford tert-butyl 8-(6-methoxypyridin-3-yl)-4-methyl-3,4-dihydroimidazo[1,2-a:5,4-b']dipyridine-1(2H)-carboxylate (125 mg, 0.317 mmol, 39% yield). LC/MS (M+H) 395.2; $^1$H NMR (500 MHz, chloroform-d) δ 8.39 (dd, J=2.4, 0.6 Hz, 1H), 8.09 (s, 1H), 7.78 (dd, J=8.7, 2.6 Hz, 2H), 7.45 (d, J=8.4 Hz, 1H), 6.87 (dd, J=8.6, 0.7 Hz, 1H), 4.03-3.89 (m, 4H), 3.65 (br. s., 1H), 3.27-3.16 (m, 1H), 2.24 (dtd, J=14.0, 6.9, 2.4 Hz, 1H), 1.77 (dddd, J=14.0, 9.3, 6.9, 2.7 Hz, 1H), 1.50 (s, 9H), 1.48 (br. s., 3H).

Intermediate 37C: 8-(6-Methoxypyridin-3-yl)-4-methyl-1,2,3,4-tetrahydroimidazo [1,2-a:5,4-b'] dipyridine, 2 TFA

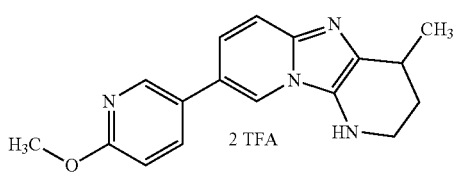

(37C)

Trifluoroacetic acid (1 mL) was added to a solution of tert-butyl 8-(6-methoxypyridin-3-yl)-4-methyl-3,4-dihydroimidazo[1,2-a:5,4-b']dipyridine-1(2H)-carboxylate (125 mg, 0.317 mmol) in DCM (5 mL). The mixture was allowed to stir at room temperature for 2 h. The reaction mixture was concentrated in vacuo. Residual solvents were removed under high vacuum to afford 8-(6-methoxypyridin-3-yl)-4-methyl-1,2,3,4-tetrahydroimidazo[1,2-a:5,4-b']dipyridine, 2 TFA (168 mg, 0.322 mmol, quantitative yield). LC/MS (M+H) 295.1.

Example 37

Following the N-arylation procedure and purification method used in the final step for the preparation of Example 1, 8-(6-methoxypyridin-3-yl)-4-methyl-1,2,3,4-tetrahydroimidazo[1,2-a:5,4-b']dipyridine, 2 TFA (83 mg, 0.158 mmol) was reacted with 2-bromo-1,4-dimethylbenzene (58.5 mg, 0.316 mmol) to afford 1-(2,5-dimethylphenyl)-8-(6-methoxypyridin-3-yl)-4-methyl-1,2,3,4-tetrahydroimidazo[1,2-a:5,4-b']dipyridine (8.6 mg, 0.022 mmol, 14% yield). LC/MS (M+H) 399.2; $^1$H NMR (500 MHz, DMSO-d$_6$) δ 8.08 (s, 1H), 7.71 (d, J=8.8 Hz, 1H), 7.64 (d, J=9.2 Hz, 1H), 7.45 (d, J=9.5 Hz, 1H), 7.26 (d, J=7.7 Hz, 1H), 7.04 (s, 1H), 6.93 (d, J=7.3 Hz, 1H), 6.88 (d, J=8.8 Hz, 1H), 6.30 (d, J=18.0 Hz, 1H), 3.85 (s, 3H), 3.70-3.61 (m, 1H), 3.45 (d, J=13.9 Hz, 1H), 3.25-3.07 (m, 1H), 2.48-2.41 (m, 3H), 2.16-1.88 (m, 4H), 1.69-1.53 (m, 1H), 1.49-1.28 (m, 3H).

Example 38

1-(2-(Difluoromethoxy)phenyl)-8-(6-methoxypyridin-3-yl)-4-methyl-1,2,3,4-tetrahydroimidazo[1,2-a:5,4-b']dipyridine

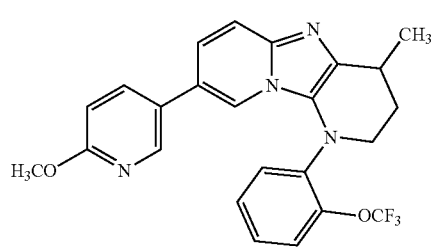

(38)

Following the N-arylation procedure and purification method used in the final step for the preparation of Example 1, 8-(6-methoxypyridin-3-yl)-4-methyl-1,2,3,4-tetrahydroimidazo[1,2-a:5,4-b']dipyridine, 2 TFA (83 mg, 0.158 mmol) was reacted with 1-bromo-2-(difluoromethoxy)benzene (70.5 mg, 0.316 mmol) to afford 1-(2-(difluoromethoxy)phenyl)-8-(6-methoxypyridin-3-yl)-4-methyl-1,2,3,4-tetrahydroimidazo[1,2-a:5,4-b']dipyridine (3.0 mg, 6.87 μmol, 4.4% yield). LC/MS (M+H) 437.2; $^1$H NMR (500 MHz, DMSO-d$_6$) δ 8.19-8.11 (m, 1H), 7.77 (dd, J=8.6, 2.4 Hz, 1H), 7.70 (d, J=9.2 Hz, 1H), 7.54 (d, J=6.2 Hz, 1H), 7.38 (t, J=74.1 Hz, 1H), 7.36 (d, J=8.1 Hz, 1H), 7.28 (s, 1H), 7.20 (t, J=7.7 Hz, 1H), 7.15-7.08 (m, 1H), 6.88 (d, J=8.4 Hz, 1H), 6.42 (d, J=8.1 Hz, 1H), 3.85 (s, 3H), 3.81-3.64 (m, 2H), 3.20-3.08 (m, 1H), 2.08-1.91 (m, 1H), 1.55 (br. s., 1H), 1.37 (d, J=5.5 Hz, 3H).

Example 39

1-(2,5-Dimethylphenyl)-4-methyl-8-(1-methyl-1H-pyrazol-4-yl)-1,2,3,4-tetrahydroimidazo[1,2-a:5,4-b'] dipyridine

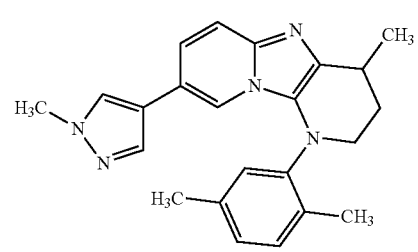

(39)

Intermediate 39A: tert-Butyl 8-(6-methoxypyridin-3-yl)-4-methyl-3,4-dihydroimidazo [1,2-a:5,4-b'] dipyridine-1(2H)-carboxylate

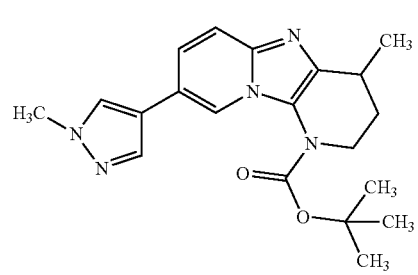

(39A)

Following the metal-mediated coupling procedure and purification method used in the preparation of Intermediate 1B, tert-butyl 8-bromo-4-methyl-3,4-dihydroimidazo [1,2-a:5,4-b']dipyridine-1(2H)-carboxylate (Intermediate 37A, 350 mg, 0.956 mmol) was reacted with (1-methyl-1H-pyrazol-4-yl)boronic acid (120 mg, 0.956 mmol) to afford tert-butyl 4-methyl-8-(1-methyl-1H-pyrazol-4-yl)-3,4-dihydroimidazo[1,2-a:5,4-b']dipyridine-1(2H)-carboxylate (88 mg, 0.24 mmol, 25% yield). LC/MS (M+H) 368.2.

Intermediate 39B: 4-Methyl-8-(1-methyl-1H-pyrazol-4-yl)-1,2,3,4-tetrahydroimidazo [1,2-a:5,4-b'] dipyridine, 2 TFA

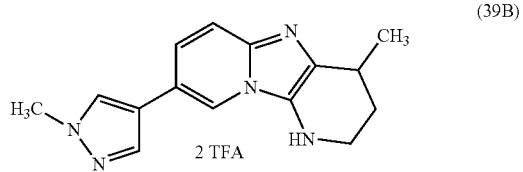

(39B)

Trifluoroacetic acid (1 mL) was added to a solution of tert-butyl 4-methyl-8-(1-methyl-1H-pyrazol-4-yl)-3,4-dihydroimidazo[1,2-a:5,4-b']dipyridine-1(2H)-carboxylate (88 mg, 0.239 mmol) in DCM (5 mL). The mixture was allowed to stir at room temperature for 2 h. The reaction mixture was concentrated in vacuo. Residual solvents were removed under high vacuum to afford 4-methyl-8-(1-methyl-1H-pyrazol-4-yl)-1,2,3,4-tetrahydroimidazo[1,2-a:5,4-b']dipyridine, 2 TFA (129 mg, 0.260 mmol, quantitative yield). LC/MS (M+H) 268.1.

Example 39

Following the N-arylation procedure and purification method used in the final step for the preparation of Example 1, 4-methyl-8-(1-methyl-1H-pyrazol-4-yl)-1,2,3,4-tetrahydroimidazo[1,2-a:5,4-b']dipyridine, 2 TFA (55 mg, 0.111 mmol) was reacted with 2-bromo-1,4-dimethylbenzene (61.6 mg, 0.333 mmol) to afford 1-(2,5-dimethylphenyl)-4-methyl-8-(1-methyl-1H-pyrazol-4-yl)-1,2,3,4-tetrahydroimidazo[1,2-a:5,4-b']dipyridine (3.8 mg, 10.2 µmol, 9.2% yield). LC/MS (M+H) 372.2; $^1$H NMR (500 MHz, DMSO-$d_6$) δ 7.86 (s, 1H), 7.50 (d, J=9.5 Hz, 1H), 7.46-7.39 (m, 1H), 7.26 (d, J=7.7 Hz, 2H), 6.98 (s, 1H), 6.91 (d, J=7.3 Hz, 1H), 6.30-6.18 (m, 1H), 3.80 (s, 3H), 3.70-3.53 (m, 1H), 3.21-3.01 (m, 2H), 2.46 (br. s., 3H), 2.05 (s, 3H), 1.91-1.85 (m, 1H), 1.65-1.50 (m, 1H), 1.46-1.26 (m, 3H).

Example 40

1-(2-(Difluoromethoxy)phenyl)-4-methyl-8-(1-methyl-1H-pyrazol-4-yl)-1,2,3,4-tetrahydroimidazo [1,2-a:5,4-b']dipyridine

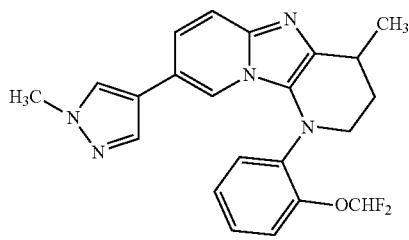

(40)

Following the N-arylation procedure and purification method used in the final step for the preparation of Example 1, 4-methyl-8-(1-methyl-1H-pyrazol-4-yl)-1,2,3,4-tetrahydroimidazo[1,2-a:5,4-b']dipyridine, 2 TFA (Intermediate 39B, 64 mg, 0.129 mmol) was reacted with 1-bromo-2-(difluoromethoxy)benzene (86 mg, 0.388 mmol) to afford 1-(2-(difluoromethoxy)phenyl)-4-methyl-8-(1-methyl-1H-pyrazol-4-yl)-1,2,3,4-tetrahydroimidazo[1,2-a:5,4-b']dipyridine (6.6 mg, 0.016 mmol, 12% yield). LC/MS (M+H) 410.2; $^1$H NMR (500 MHz, DMSO-$d_6$) δ 7.93 (s, 1H), 7.61 (d, J=8.8 Hz, 1H), 7.53 (s, 1H), 7.44 (d, J=9.9 Hz, 1H), 7.38 (t, J=74.1 Hz, 1H), 7.36 (d, J=8.1 Hz, 1H), 7.22-7.16 (m, 2H), 7.13-7.06 (m, 1H), 6.39 (d, J=8.4 Hz, 1H), 3.81 (s, 3H), 3.78-3.60 (m, 2H), 3.16-3.05 (m, 1H), 1.98 (dd, J=11.0, 3.3 Hz, 1H), 1.59-1.47 (m, 1H), 1.35 (d, J=6.6 Hz, 3H).

Example 41

4-(5-(1-(2,5-Dimethylphenyl)-6,7-dimethyl-1,2,3,4-tetrahydroimidazo [1,2-a:5,4-b']dipyridin-8-yl)pyrimidin-2-yl)morpholine

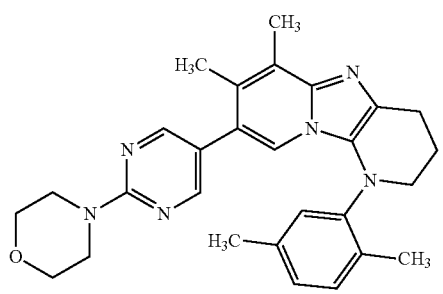

(41)

Intermediate 41A: tert-Butyl 8-bromo-6,7-dimethyl-3,4-dihydroimidazo[1,2-a:5,4-b']dipyridine-1(2H)-carboxylate

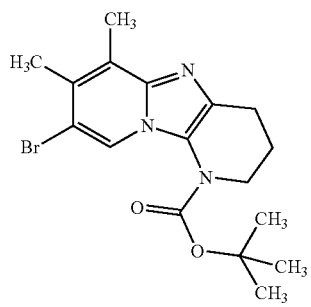

(41A)

A mixture of 5-bromo-3,4-dimethylpyridin-2-amine (1.0 g, 4.97 mmol), tert-butyl 3-oxopiperidine-1-carboxylate (0.991 g, 4.97 mmol), and acetic acid (0.028 mL, 0.497 mmol) in toluene (100 mL) was heated to reflux. Water was azeotroped using a Dean-Stark apparatus. The mixture was heated at reflux for 2 days. After cooling to room temperature, air was bubbled through the reaction mixture for 2 h to promote oxidative dehydrogenation. The resulting solution was concentrated under high vacuum to afford a viscous oil. The oil was diluted with ethyl acetate and washed with saturated aqueous sodium bicarbonate solution. The aqueous portion was back extracted with ethyl acetate. The combined organic portions were washed with brine, dried over magnesium sulfate, filtered and concentrated in vacuo. The crude product was purified twice using silica gel column chromatography (100% EtOAc) to afford butyl 8-bromo-6,7-dimethyl-3,4-dihydroimidazo[1,2-a:5,4-b']dipyridine-1(2H)-carboxylate (242 mg, 0.605 mmol, 12.16% yield). LC/MS (M+H) 380.1, 382.1. $^1$H NMR (500 MHz, chloroform-d) δ 8.06 (s, 1H), 3.76 (br. s., 2H), 2.96 (t, J=6.7 Hz, 2H), 2.63 (s, 3H), 2.45 (s, 3H), 2.15-2.07 (m, 2H), 1.52 (s, 9H).

Intermediate 41B: tert-Butyl 6,7-dimethyl-8-(2-morpholinopyrimidin-5-yl)-3,4-dihydroimidazo[1,2-a:5,4-b']dipyridine-1(2H)-carboxylate

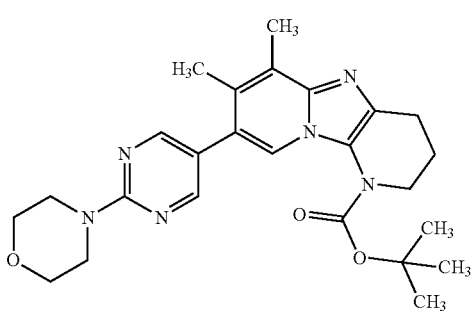

(41B)

Following the metal-mediated coupling procedure and purification method used in the preparation of Intermediate 1B, tert-butyl 8-bromo-6,7-dimethyl-3,4-dihydroimidazo[1,2-a:5,4-b']dipyridine-1(2H)-carboxylate (150 mg, 0.394 mmol) was reacted with 4-(5-(4,4,5,5-tetramethyl-1,3,2-dioxaborolan-2-yl)pyrimidin-2-yl)morpholine (115 mg, 0.394 mmol) to afford tert-butyl 6,7-dimethyl-8-(2-morpholinopyrimidin-5-yl)-3,4-dihydroimidazo[1,2-a:5,4-b']dipyridine-1(2H)-carboxylate (173 mg, 0.373 mmol, 95% yield). LC/MS (M+H) 465.3.

Intermediate 41C: 4-(5-(6,7-Dimethyl-1,2,3,4-tetrahydroimidazo[1,2-a:5,4-b']dipyridin-8-yl)pyrimidin-2-yl)morpholine, TFA

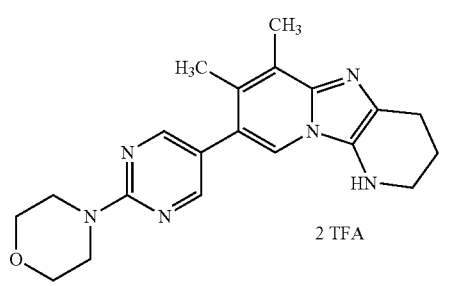

(41C)

2 TFA

Trifluoroacetic acid (1 mL) was added to a solution of tert-butyl 6,7-dimethyl-8-(2-morpholinopyrimidin-5-yl)-3,4-dihydroimidazo[1,2-a:5,4-b']dipyridine-1(2H)-carboxylate (187 mg, 0.403 mmol) in DCM (5 mL). The mixture was allowed to stir at room temperature for 2 h. The reaction mixture was concentrated in vacuo. Residual solvents were removed under high vacuum to afford 4-(5-(6,7-dimethyl-1,2,3,4-tetrahydroimidazo[1,2-a:5,4-b']dipyridin-8-yl)pyrimidin-2-yl)morpholine, TFA (145 mg, 0.303 mmol, 75% yield). LC/MS (M+H) 295.20.

Example 41

Following the N-arylation procedure and purification method used in the final step for the preparation of Example 1, 4-(5-(6,7-dimethyl-1,2,3,4-tetrahydroimidazo [1,2-a:5,4-b']dipyridin-8-yl)pyrimidin-2-yl)morpholine (30.3 mg, 0.083 mmol) was reacted with 2-bromo-1,4-dimethylbenzene (77 mg, 0.416 mmol) to afford 4-(5-(1-(2,5-dimethylphenyl)-6,7-dimethyl-1,2,3,4-tetrahydroimidazo[1,2-a:5,4-b']dipyridin-8-yl)pyrimidin-2-yl)morpholine (9.8 mg, 0.021 mmol, 25% yield). LC/MS (M+H) 469.1; $^1$H NMR (500 MHz, DMSO-$d_6$) δ 8.16 (s, 2H), 7.17 (d, J=8.1 Hz, 1H), 6.86 (d, J=7.0 Hz, 1H), 6.60 (s, 1H), 6.21 (s, 1H), 3.77-3.47 (m, 10H), 2.95-2.78 (m, 2H), 2.37 (s, 3H), 2.11 (s, 3H), 2.07 (s, 3H), 1.97-1.76 (m, 2H).

Biological Assays

The pharmacological properties of the compounds of this invention may be confirmed by a number of biological assays. The exemplified biological assays, which follow, have been carried out with compounds of the invention.
TNF or CD40L-Induced HEK-Blue Assay Test compounds serially diluted in DMSO were plated in an assay plate (Labcyte, Cat. #LP-0200) at final concentrations ranging from 0.004 μM to 25 μM. TNFα (final concentration 0.5 ng/ml) or CD40L (final concentration 30 ng/ml) in assay buffer [DMEM, 4.5 g/l glucose (Gibco, Cat. 21063-029), 10% FBS (Sigma, F4135), 1% Penicillin-Streptomycin (Gibco, Cat. 15140-122), 1% Anti-Anti (Gibco, Cat. 15240-112) and 2 mM L-glutamine (Gibco, Cat. 25030-081)] was then added to the assay plate. After a 30 minute pre-incubation at 37° C. and 5% $CO_2$, HEK-Blue-CD40L cells (InvivoGen, Cat. Code hkb-cd40) containing a NF-κB-driven secreted alkaline phosphatase reporter gene were seeded into the assay plate at a density of 20,000 cells per well. This plate was then incubated for 18 h at 37° C. and 5% $CO_2$. Secreted alkaline phosphatase expression was measured using QUANTI-Blue (InvivoGen, Cat. Code rep-qbl) according to manufacturer's specifications and the assay plate was read on a PerkinElmer Envision at 620 nm.

Inhibition data for the test compound over a range of concentrations was plotted as percentage inhibition of the test compound (100%=maximum inhibition). $IC_{50}$ values were determined after correcting for background [(sample read−mean of low control)/(mean of high control−mean of low control)] where by the low control is DMSO without stimulation and high control is DMSO with stimulation. The $IC_{50}$ is defined as the concentration of test compound which produces 50% inhibition and was quantified using the 4 parameter logistic equation to fit the data.

Table 2 lists the $IC_{50}$ values measured in the TNF induced HEK-Blue assay for Examples 1 to 21 of this invention. The results in Table 2 are reported as: "A" represents an $IC_{50}$ value of less than 1 μM; "B" represents an $IC_{50}$ value in the range of 1 μM to less than 10 μM; and "C" represents an $IC_{50}$ value in the range of 10 μM to 25 μM. The compounds of the present invention, as exemplified by Examples 1 to 41 showed $IC_{50}$ values measured in the TNF induced HEK-Blue assay of 25 μM or less.

TABLE 2

| Ex. No. | TNF induced HEK-Blue assay $IC_{50}$ value |
|---|---|
| 1 | B |
| 2 | A |

TABLE 2-continued

| Ex. No. | TNF induced HEK-Blue assay IC$_{50}$ value |
|---|---|
| 3 | A |
| 4 | B |
| 5 | A |
| 6 | A |
| 7 | A |
| 8 | B |
| 9 | A |
| 10 | A |
| 11 | B |
| 12 | A |
| 13 | A |
| 14 | A |
| 15 | A |
| 16 | A |
| 17 | A |
| 18 | A |
| 19 | A |
| 20 | A |
| 21 | A |
| 22 | B |
| 23 | B |
| 24 | B |
| 25 | A |
| 26 | A |
| 27 | A |
| 28 | A |
| 29 | A |
| 30 | B |
| 31 | A |
| 32 | A |
| 33 | A |
| 34 | A |
| 35 | A |
| 36 | B |
| 37 | A |
| 38 | A |
| 39 | A |
| 40 | A |
| 41 | B |

The invention claimed is:

1. A compound of Formula (I)

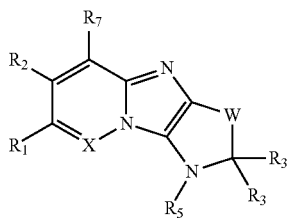

or a salt thereof, wherein:

X is CR$_6$ or N;

W is:
(i) —(CR$_3$R$_3$)$_{1-4}$—; or
(ii) —(CR$_3$R$_3$)$_x$—Y—(CR$_3$R$_3$)$_y$—;

each Y is independently O, NR$_4$, or S(O)$_p$;

x is zero, 1, or 2;

y is 1, 2, or 3, provided that (x+y) is 1, 2, or 3;

R$_1$ is C$_{2-6}$ alkenyl substituted with zero to 6 R$_{1a}$, C$_{2-6}$ alkynyl substituted with zero to 4 R$_{1a}$, —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-7 membered heterocyclyl substituted with zero to 3 R$_{1a}$), or —(CR$_g$R$_g$)$_r$(mono- or bicyclic heteroaryl substituted with zero to 3 R$_{1a}$);

R$_2$ is H, halo, —CN, —CF$_3$, —OCF$_3$, —NO$_2$, C$_{1-6}$ alkyl substituted with zero to 6 R$_{1a}$, —(CR$_g$R$_g$)$_r$OR$_e$, —(CR$_g$R$_g$)$_r$NR$_c$R$_c$, —(CR$_g$R$_g$)$_r$S(O)$_p$R$_b$, —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-7 membered heterocyclyl substituted with zero to 3 R$_{1a}$), or —(CR$_g$R$_g$)$_r$(monocyclic heteroaryl substituted with zero to 3 R$_{1a}$);

each R$_3$ is independently H, halo, —CN, —OH, —OCF$_3$, C$_{1-6}$ alkyl, C$_{1-6}$ haloalkyl, C$_{2-6}$ alkenyl, C$_{2-6}$ alkynyl, —(CR$_g$R$_g$)$_r$C(O)R$_b$, —(CR$_g$R$_g$)$_r$C(O)OR$_b$, —(CR$_g$R$_g$)$_r$C(O)NR$_c$R$_c$, —(CR$_g$R$_g$)$_r$OR$_e$, —(CR$_g$R$_g$)$_r$OC(O)R$_b$, —(CR$_g$R$_g$)$_r$OC(O)NR$_c$R$_c$, —(CR$_g$R$_g$)$_r$OC(O)OR$_d$, —(CR$_g$R$_g$)$_r$NR$_c$R$_c$, —(CR$_g$R$_g$)$_r$NR$_b$C(O)R$_d$, —(CR$_g$R$_g$)$_r$NR$_b$C(O)OR$_d$, —(CR$_g$R$_g$)$_r$NR$_b$C(O)NR$_c$R$_c$, —(CR$_g$R$_g$)$_r$NR$_b$S(O)$_p$R$_d$, —(CR$_g$R$_g$)$_r$S(O)$_p$R$_b$, —(CR$_g$R$_g$)$_r$S(O)$_p$NR$_c$R$_c$, —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-7 membered heterocyclyl substituted with zero to 3 R$_{1a}$), or —(CR$_g$R$_g$)$_r$(mono- or bicyclic heteroaryl substituted with zero to 3 R$_{1a}$); or two R$_3$ along with the carbon atom to which they are attached form C=O, C=NOR$_b$, a spirocarbocyclyl group, or a spiroheterocyclyl group;

each R$_4$ is independently H, C$_{1-6}$ alkyl substituted with zero to 6 R$_{1a}$, C$_{3-7}$ cycloalkyl substituted with zero to 6 R$_{1a}$, —C(O)R$_b$, —C(O)NR$_c$R$_c$, —C(O)OR$_b$, —S(O)$_2$R$_b$, —S(O)$_2$NR$_c$R$_c$, —S(O)$_2$OR$_b$, —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-7 membered heterocyclyl substituted with zero to 3 R$_{1a}$), or —(CR$_g$R$_g$)$_r$(monocyclic heteroaryl substituted with zero to 3 R$_{1a}$);

R$_5$ is —(CR$_g$R$_g$)$_r$(3-14 membered carbocyclyl substituted with zero to 3 R$_{1a}$), —(CR$_g$R$_g$)$_r$(aryl substituted with zero to 3 R$_{1a}$), —(CR$_g$R$_g$)$_r$(5-10 membered heterocyclyl substituted with zero to 3 R$_{1a}$), or —(CR$_g$R$_g$)$_r$(mono- or bicyclic heteroaryl substituted with zero to 3 R$_{1a}$);

R$_6$ is H, halo, or —CN;

R$_7$ is H, halo, —CN, C$_{1-6}$ alkyl, or C$_{1-3}$ alkoxy;

each R$_{1a}$ is independently F, Cl, —CN, C$_{1-6}$ alkyl substituted with zero to 6 R$_a$, C$_{3-6}$ cycloalkyl substituted with zero to 6 R$_a$, C$_{1-3}$ alkoxy substituted with zero to 6 R$_a$, C$_{1-3}$ haloalkoxy, heterocycloalkyl substituted with zero to 6 R$_a$, aryl substituted with zero to 6 R$_a$, mono- or bicyclic heteroaryl substituted with zero to 6 R$_a$, —C(O)R$_b$, —C(O)OR$_b$, —C(O)NR$_c$R$_c$, —OC(O)R$_b$, —OC(O)NR$_c$R$_c$, —OC(O)OR$_d$, —NR$_c$R$_c$, —NR$_b$C(O)R$_d$, —NR$_b$C(O)OR$_d$, —NR$_b$S(O)$_p$R$_d$, —NR$_b$C(O)NR$_c$R$_c$, —NR$_b$S(O)$_p$NR$_c$R$_c$, —S(O)$_p$R$_b$, —S(O)$_p$NR$_c$R$_c$, or —C(O)NR$_b$(CH$_2$)$_{1-3}$NR$_c$R$_c$;

each R$_a$ is independently halo, —CN, —OH, —NH$_2$, C$_{1-3}$ alkyl, C$_{1-3}$ fluoroalkyl, C$_{2-4}$ alkenyl, C$_{2-4}$ alkynyl, C$_{1-3}$ alkoxy, C$_{1-3}$ fluoroalkoxy, —C(O)OH, —C(O)(C$_{1-3}$ alkyl), —C(O)O(C$_{1-4}$ alkyl), —OC(O)(C$_{1-3}$ alkyl), —NH(C$_{1-3}$ alkyl), —N(C$_{1-3}$ alkyl)$_2$, —C(O)NH(C$_{1-3}$ alkyl), —OC(O)NH(C$_{1-3}$ alkyl), —NHC(O)NH(C$_{1-3}$ alkyl), —C(=NH)(NH$_2$), C$_{3-7}$ carbocyclyl, aryl, 5-7 membered heterocyclyl, mono- or bicyclic heteroaryl, —O(aryl), —O(benzyl), —O(heterocyclyl), —S(C$_{1-3}$ alkyl), —S(aryl), —S(heterocyclyl), —S(O)(aryl), —S(O)(heterocyclyl), —S(O)$_2$(aryl), —S(O)$_2$(heterocyclyl), —NHS(O)$_2$(aryl), —NHS(O)$_2$(heterocyclyl), —NHS(O)$_2$NH(aryl), —NHS(O)$_2$NH(heterocyclyl), —NH(aryl) —NH(heterocyclyl), —NHC(O)(aryl), —NHC(O)(C$_{1-3}$ alkyl), —NHC(O)(heterocyclyl), —OC(O)(aryl), —OC(O)(heterocyclyl), —NHC(O)NH(aryl), —NHC(O)NH(heterocyclyl), —OC(O)O(C$_{1-3}$ alkyl), —OC(O)O(aryl), —OC(O)O(heterocyclyl), —OC(O)NH(aryl), —OC(O)NH(heterocyclyl), —NHC(O)O(aryl), —NHC(O)O(heterocyclyl), —NHC(O)O(C$_{1-3}$ alkyl), —C(O)NH(aryl), —C(O)NH(heterocyclyl), —C(O)O(aryl), —C(O)O(heterocyclyl), —N(C$_{1-3}$ alkyl)S(O)$_2$(aryl), —N(C$_{1-3}$ alkyl)S(O)$_2$(heterocyclyl), —N(C$_{1-3}$ alkyl)S(O)$_2$NH(aryl), —N(C$_{1-3}$ alkyl)S(O)$_2$NH(heterocyclyl), —N(C$_{1-3}$ alkyl)(aryl), —N(C$_{1-3}$ alkyl)(heterocyclyl), —N(C$_{1-3}$ alkyl)C(O)(aryl), —N(C$_{1-3}$ alkyl)C(O)(heterocyclyl), —N(C$_{1-3}$ alkyl)C(O)NH(aryl), —(CH$_2$)$_{0-3}$C(O)NH(heterocyclyl), —OC(O)N(C$_{1-3}$ alkyl)(aryl), —OC(O)N(C$_{1-3}$ alkyl)(heterocyclyl), —N(C$_{1-3}$ alkyl)C(O)O(aryl), —N(C$_{1-3}$ alkyl)C(O)O(heterocyclyl), —C(O)N(C$_{1-3}$ alkyl)(aryl), —C(O)N(C$_{1-3}$ alkyl)(heterocyclyl), —NHS(O)$_2$N(C$_{1-3}$ alkyl)(aryl), —NHS(O)$_2$N(C$_{1-3}$ alkyl)(heterocyclyl), —NHP(O)$_2$N(C$_{1-3}$ alkyl)(aryl), —NHC(O)N(C$_{1-3}$ alkyl)(aryl), —NHC(O)N(C$_{1-3}$ alkyl)(heterocyclyl), —N(C$_{1-3}$ alkyl)S(O)$_2$N(C$_{1-3}$ alkyl)(aryl), —N(C$_{1-3}$ alkyl)S(O)$_2$N(C$_{1-3}$ alkyl)(heterocyclyl), —N(C$_{1-3}$ alkyl)C(O)N(C$_{1-3}$ alkyl)(aryl), —N(C$_{1-3}$ alkyl)C(O)N(C$_{1-3}$ alkyl)(heterocyclyl), or —Si(C$_{1-3}$ alkyl)$_3$;

each R$_b$ is independently H, C$_{1-6}$ alkyl substituted with zero to 6 R$_f$, C$_{3-7}$ cycloalkyl substituted with zero to 6 R$_f$, heterocycloalkyl substituted with zero to 6 R$_f$, aryl substituted with zero to 3 R$_f$, or mono- or bicyclic heteroaryl substituted with zero to 3 R$_f$;

each R$_c$ is independently H, C$_{1-6}$ alkyl substituted with zero to 6 R$_f$, C$_{3-7}$ cycloalkyl substituted with zero to 6 R$_f$, heterocycloalkyl substituted with zero to 6 R$_f$, aryl substituted with zero to 3 R$_f$, or mono- or bicyclic heteroaryl substituted with zero to 3 R$_f$; or when attached to the same nitrogen, two R$_c$ along with the nitrogen atom to which they are attached form 4-8 membered heterocyclic ring optionally substituted with R$_g$;

each R$_d$ is independently H, C$_{1-6}$ alkyl substituted with zero to 6 R$_f$, C$_{3-7}$ cycloalkyl substituted with zero to 6 R$_f$, heterocycloalkyl substituted with zero to 6 R$_f$, aryl substituted with zero to 3 R$_f$, or mono- or bicyclic heteroaryl substituted with zero to 3 R$_f$;

each R$_e$ is independently H, C$_{1-6}$ alkyl substituted with zero to 6 R$_f$, C$_{1-3}$ haloalkyl, C$_{3-7}$ cycloalkyl substituted with zero to 6 R$_f$, heterocycloalkyl substituted with zero to 6 R$_f$, aryl substituted with zero to 3 R$_f$, or mono- or bicyclic heteroaryl substituted with zero to 3 R$_f$;

each R$_f$ is independently H, halo, —OH, —CN, C$_{1-6}$ alkyl substituted with zero to 6 R$_a$, C$_{1-3}$ alkoxy, C$_{3-7}$ cycloalkyl substituted with zero to 6 R$_a$, heterocycloalkyl substituted with zero to 6 R$_a$, aryl substituted with zero to 3 R$_a$, or mono- or bicyclic heteroaryl substituted with zero to 3 R$_a$;

each R$_g$ is independently H, F, —OH, —CN, C$_{1-3}$ alkyl, —CF$_3$, or phenyl;

each p is independently zero, 1, or 2; and each r is independently zero, 1, 2, 3, or 4.

2. The compound according to claim 1 or a salt thereof, wherein X is CR$_6$.

3. The compound according to claim 1 or a salt thereof, wherein X is N.

4. The compound according to claim 1 or a salt thereof, wherein:
W is —(CR$_3$R$_3$)$_{1-4}$—.

5. The compound according to claim 1 or a salt thereof, wherein:
W is —(CR$_3$R$_3$)$_2$—.

6. The compound according to claim 1 or a salt thereof, wherein:
W is —(CR$_3$R$_3$)$_x$—Y—(CR$_3$R$_3$)$_y$—.

7. The compound according to claim 1 or a salt thereof, wherein:
X is CR$_6$;
W is —(CR$_3$R$_3$)$_{1-2}$—;
R$_1$ is aryl substituted with zero to 3 R$_{1a}$ or mono- or bicyclic heteroaryl substituted with zero to 3 R$_{1a}$;
R$_2$ is H, F, Cl, or C$_{1-3}$ alkyl;
each R$_3$ is independently H, —OH, or —CH$_3$;
R$_5$ is phenyl, pyridinyl, pyrimidinyl, isoquinolinyl, indolyl, isoindolinonyl, benzoimidazolyl, or benzothiazolyl, each substituted with 0 to 3 substituents independently selected from F, Cl, —CN, C$_{1-3}$ alkyl, C$_{1-3}$ fluoroalkyl, C$_{1-3}$ alkoxy, and C$_{1-3}$ fluoroalkoxy;
R$_6$ is H or —CH$_3$;
each R$_{1a}$ is independently F, Cl, —CN, C$_{1-3}$ alkyl substituted with zero to 6 R$_a$, C$_{1-3}$ alkoxy, C$_{1-3}$ fluoroalkoxy, morpholinyl, or methyloxadiazolyl; and
each R$_a$ is independently F, —OH, —CN, or —NH$_2$.

8. The compound according to claim 1 or a salt thereof, wherein:
X is CR$_6$;
W is —(CR$_3$R$_3$)$_2$—;
R$_1$ is phenyl, pyrazolyl, pyridinyl, or pyrimidinyl, each substituted with —CH$_3$, —OCH$_3$, —C(CH$_3$)$_2$OH, morpholinyl, or methyloxadiazolyl;
R$_2$ is H, Cl, or —CH$_3$;
each R$_3$ is H or —CH$_3$;
R$_5$ is phenyl substituted with 0 to 2 substituents independently selected from F, Cl, —CH$_3$, —CH$_2$CH$_3$, —CF$_3$, —OCH$_3$, —OCHF$_2$, and —OCF$_3$; or isoquinolinyl; and
R$_6$ is H.

9. The compound according to claim 1 or a salt thereof, wherein said compound is: 1-(2,5-dimethylphenyl)-8-(6-methoxypyridin-3-yl)-7-methyl-1,2,3,4-tetrahydroimidazo[1,2-a:5,4-b']dipyridine (1); 1-(2-(difluoromethoxy)phenyl)-8-(6-methoxypyridin-3-yl)-7-methyl-1,2,3,4-tetrahydroimidazo[1,2-a:5,4-b']dipyridine (2); 1-(2,5-dimethylphenyl)-7-methyl-8-(1-methyl-1H-pyrazol-4-yl)-1,2,3,4-tetrahydroimidazo[1,2-a:5,4-b']dipyridine (3); 1-(2-(difluoromethoxy)phenyl)-7-methyl-8-(1-methyl-1H-pyrazol-4-yl)-1,2,3,4-tetrahydroimidazo[1,2-a:5,4-b']dipyridine (4); 1-(2,5-dimethylphenyl)-8-(6-methoxypyridin-3-yl)-1,2,3,4-tetrahydroimidazo[1,2-a:5,4-b']dipyridine (5); 1-(2-(difluoromethoxy)phenyl)-8-(6-methoxypyridin-3-yl)-1,2,3,4-tetrahydroimidazo[1,2-a:5,4-b']dipyridine (6); 1-(2-methoxy-5-methylphenyl)-8-(6-methoxypyridin-3-yl)-1,2,3,4-tetrahydroimidazo [1,2-a:5,4-b']dipyridine (7); 1-(isoquinolin-1-yl)-8-(6-methoxypyridin-3-yl)-1,2,3,4-tetrahydroimidazo[1,2-a:5,4-b']dipyridine (8); 8-(6-methoxypyridin-3-yl)-1-(o-tolyl)-1,2,3,4-tetrahydroimidazo[1,2-a:5,4-b']dipyridine (9); 8-(6-methoxypyridin-3-yl)-1-(2-(trifluoromethoxy)phenyl)-1,2,3,4-tetrahydroimidazo[1,2-a:5,4-b']dipyridine (10); 8-(6-methoxypyridin-3-yl)-1-(2-methyl-5-(trifluoromethyl)phenyl)-1,2,3,4-tetrahydroimidazo [1,2-a:5,4-b']dipyridine (11); 1-(2,5-dimethylphenyl)-8-(1-methyl-1H-pyrazol-4-yl)-1,2,3,4-tetrahydroimidazo[1,2-a:5,4-b']dipyridine (12); 1-(2-(difluoromethoxy)phenyl)-8-(1-methyl-1H-pyrazol-4-yl)-1,2,3,4-tetrahydroimidazo[1,2-a:5,4-b']dipyridine (13); 4-(5-(1-(2,5-dimethylphenyl)-1,2,3,4-tetrahydroimidazo[1, 2-a:5,4-b']dipyridin-8-yl)pyrimidin-2-yl) morpholine (14); 4-(5-(1-(2-(difluoromethoxy)phenyl)-1,2,3,4-tetrahydroimidazo [1,2-a:5,4-b']dipyridin-8-yl)pyrimidin-2-yl)morpholine (15); 2-(4-(1-(2,5-dimethylphenyl)-1,2,3,4-tetrahydroimidazo[1,2-a:5,4-b']dipyridin-8-yl)phenyl)-5-methyl-1,3,4-oxadiazole (16); 2-(4-(1-(2-(difluoromethoxy)phenyl)-1,2,3,4-tetrahydroimidazo[1,2-a:5,4-b']dipyridin-8-yl)phenyl)-5-methyl-1,3,4-oxadiazole (17); 2-(5-(1-(2,5-dimethylphenyl)-1,2,3,4-tetrahydroimidazo[1,2-a:5,4-b']dipyridin-8-yl)pyrimidin-2-yl)propan-2-ol (18); 4-(5-(1-(2-(difluoromethoxy)-5-methylphenyl)-1,2,3,4-tetrahydroimidazo[1,2-a:5,4-b']dipyridin-8-yl) pyrimidin-2-yl)morpholine (19); 1-(2-(difluoromethoxy)-5-methylphenyl)-8-(6-methoxypyridin-3-yl)-1,2,3,4-tetrahydroimidazo[1,2-a:5,4-b']dipyridine (20); 2-(5-(7-chloro-1-phenyl-1,2,3,4-tetrahydroimidazo[1,2-a:5,4-b'] dipyridin-8-yl)pyrimidin-2-yl)propan-2-ol (21); 7-chloro-1-(2-(difluoromethoxy)phenyl)-8-(6-methoxypyridin-3-yl)-1,2,3,4-tetrahydroimidazo[1,2-a:5,4-b']dipyridine (22); 7-chloro-1-(2,5-dimethylphenyl)-8-(6-methoxypyridin-3-yl)-1,2,3,4-tetrahydroimidazo[1,2-a:5,4-b']dipyridine (23); 1-(2,3-dimethylphenyl)-8-(6-methoxypyridin-3-yl)-1,2,3,4-tetrahydroimidazo[1,2-a:5,4-b']dipyridine (24); 1-(5-fluoro-2-methylphenyl)-8-(6-methoxypyridin-3-yl)-1,2,3,4-tetrahydroimidazo[1,2-a:5,4-b']dipyridine (25); 1-(4-fluoro-2-methylphenyl)-8-(6-methoxypyridin-3-yl)-1,2,3,4-tetrahydroimidazo[1,2-a:5,4-b']dipyridine (26); 1-(2-methoxy-5-methylphenyl)-8-(6-methoxypyridin-3-yl)-1,2,3,4-tetrahydroimidazo[1,2-a:5,4-b']dipyridine (27); 1-(2-ethylphenyl)-8-(6-methoxypyridin-3-yl)-1,2,3,4-tetrahydroimidazo [1,2-a:5,4-b']dipyridine (28); 8-(6-methoxypyridin-3-yl)-1-(2-(trifluoromethoxy)phenyl)-1,2,3,4-tetrahydroimidazo[1,2-a:5,4-b']dipyridine (29); 1-(2,4-dimethylphenyl)-8-(6-methoxypyridin-3-yl)-1,2,3,4-tetrahydroimidazo[1,2-a:5,4-b']dipyridine (30); 1-(2-chlorophenyl)-8-(6-methoxypyridin-3-yl)-1,2,3,4-tetrahydroimidazo[1,2-a:5,4-b']dipyridine (31); 1-(5-chloro-2-methylphenyl)-8-(6-methoxypyridin-3-yl)-1,2,3,4-tetrahydroimidazo [1,2-a:5,4-b']dipyridine (32); 4-(5-(1-(2,5-dimethylphenyl)-1,2,3,4-tetrahydroimidazo [1,2-a:5,4-b']dipyridin-8-yl)pyrimidin-2-yl)morpholine (33); 2-(5-(1-(2-(difluoromethoxy) phenyl)-1,2,3,4-tetrahydroimidazo[1,2-a:5,4-b']dipyridin-8-yl)pyrimidin-2-yl)propan-2-ol (34); 2-(4-(1-(2-(difluoromethoxy)phenyl)-1,2,3,4-tetrahydroimidazo [1,2-a:5,4-b']dipyridin-8-yl)phenyl)propan-2-ol (35); 2-(4-(1-(2,5-dimethylphenyl)-1,2,3,4-tetrahydroimidazo [1,2-a:5,4-b']dipyridin-8-yl)phenyl)propan-2-ol (36); 1-(2,5-dimethylphenyl)-8-(6-methoxypyridin-3-yl)-4-methyl-1,2,3,4-tetrahydroimidazo[1,2-a:5,4-b']dipyridine (37); 1-(2-(difluoromethoxy)phenyl)-8-(6-methoxypyridin-3-yl)-4-methyl-1,2,3,4-tetrahydroimidazo [1,2-a:5,4-b']dipyridine (38); 1-(2,5-dimethylphenyl)-4-methyl-8-(1-methyl-1H-pyrazol-4-yl)-1,2,3,4-tetrahydroimidazo[1,2-a:5,4-b']dipyridine (39); 1-(2-(difluoromethoxy)phenyl)-4-methyl-8-(1-methyl-1H-pyrazol-4-yl)-1,2,3,4-tetrahydroimidazo[1,2-a:5,4-b']dipyridine (40); or 4-(5-(1-(2,5-dimethylphenyl)-6,7-dimethyl-1,2,3,4-tetrahydroimidazo[1,2-a:5,4-b']dipyridin-8-yl)pyrimidin-2-yl)morpholine (41).

10. A pharmaceutical composition comprising one or more compounds according to claim 1 or a salt thereof; and a pharmaceutically acceptable carrier or diluent.

11. A method for treating a disease comprising the administration to a subject in need thereof a therapeutically-effective amount of at least one compound according to claim 1, wherein said disease is an inflammatory or autoimmune disease.

12. The method according to claim 11, wherein the disease is selected from Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes, TNF receptor associated periodic syndrome, familial Mediterranean fever, adult onset stills, systemic onset juvenile idiopathic arthritis, multiple sclerosis, neuropathic pain, gout, and gouty arthritis.

\* \* \* \* \*

UNITED STATES PATENT AND TRADEMARK OFFICE
CERTIFICATE OF CORRECTION

PATENT NO. : 10,112,944 B2
APPLICATION NO. : 15/558724
DATED : October 30, 2018
INVENTOR(S) : Lawrence R. Marcin et al.

Page 1 of 1

It is certified that error appears in the above-identified patent and that said Letters Patent is hereby corrected as shown below:

In the Claims

Claim 1, Column 66, Line 12, delete "$R_g)_r$ C(O)" and insert -- $R_g)_rC(O)$ --, therefor.

Claim 1, Column 66, Line 17, delete "$R_g$ $R_g$" and insert -- $R_gR_g$ --, therefor.

Claim 1, Column 66, Line 29, delete "-$S(O)_2$ $R_b$," and insert -- -$S(O)_2R_b$, --, therefor.

Claim 1, Column 66, Line 67, delete "-NH(aryl)" and insert -- -NH(aryl), --, therefor.

Claim 1, Column 67, Line 10, delete "$(O)_2$ (" and insert -- $(O)_2($ --, therefor.

Claim 1, Column 69, Line 1, delete "-yl) morpholine" and insert -- -yl)morpholine --, therefor.

Claim 9, Column 69, Line 12, delete "yl) pyrimidin" and insert -- yl)pyrimidin --, therefor.

Claim 9, Column 70, Line 3, delete ") phenyl)-" and insert -- )phenyl)- --, therefor.

Signed and Sealed this
Tenth Day of September, 2019

Andrei Iancu
*Director of the United States Patent and Trademark Office*